(12) United States Patent
Baik et al.

(10) Patent No.: US 11,208,458 B2
(45) Date of Patent: Dec. 28, 2021

(54) COMPOSITIONS AND METHODS FOR INTERNALIZING ENZYMES

(71) Applicant: Regeneron Pharmaceuticals, Inc., Tarrytown, NY (US)

(72) Inventors: Andrew Baik, Bronx, NY (US); Katherine Cygnar, New York, NY (US); Christopher Schoenherr, Piermont, NY (US); Christos Kyratsous, Irvington, NY (US); Cheng Wang, Beijing (CN)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 388 days.

(21) Appl. No.: 16/001,717

(22) Filed: Jun. 6, 2018

(65) Prior Publication Data

US 2018/0355017 A1 Dec. 13, 2018

Related U.S. Application Data

(60) Provisional application No. 62/516,656, filed on Jun. 7, 2017, provisional application No. 62/574,719, filed on Oct. 19, 2017, provisional application No. 62/673,098, filed on May 17, 2018.

(51) Int. Cl.

| | | |
|---|---|---|
| *C07K 14/705* | (2006.01) | |
| *C12N 9/14* | (2006.01) | |
| *C12N 9/24* | (2006.01) | |
| *C07K 16/28* | (2006.01) | |
| *C12N 9/34* | (2006.01) | |
| *A61P 43/00* | (2006.01) | |
| *A61K 38/47* | (2006.01) | |
| *A61K 48/00* | (2006.01) | |

(52) U.S. Cl.
CPC ........ *C07K 14/70596* (2013.01); *A61K 38/47* (2013.01); *A61P 43/00* (2018.01); *C07K 16/2896* (2013.01); *C12N 9/14* (2013.01); *C12N 9/24* (2013.01); *C12N 9/2402* (2013.01); *C12N 9/2428* (2013.01); *A61K 48/00* (2013.01); *C07K 2317/24* (2013.01); *C07K 2317/31* (2013.01); *C07K 2317/622* (2013.01); *C07K 2317/77* (2013.01); *C07K 2317/92* (2013.01); *C07K 2319/00* (2013.01); *C07K 2319/33* (2013.01); *C12N 2710/10043* (2013.01); *C12N 2750/14143* (2013.01)

(58) Field of Classification Search
CPC .... A61K 38/47; A61K 48/00; C07K 2317/24; C07K 2317/31; C07K 2319/00; C07K 2319/31; C07K 2319/33; C12N 9/14; C12N 2710/10043; C12N 2710/14143
USPC .................. 435/6.1, 91.1, 91.31, 455, 458; 514/44 A, 44 R; 536/23.1, 24.5
See application file for complete search history.

(56) References Cited

U.S. PATENT DOCUMENTS

| | | |
|---|---|---|
| 4,444,878 A | 4/1984 | Paulus |
| 5,030,717 A | 7/1991 | Tramontano et al. |
| 5,126,258 A | 6/1992 | Lerner et al. |
| 5,156,965 A | 10/1992 | Schochetman et al. |
| 5,229,272 A | 7/1993 | Paul et al. |
| 5,585,108 A | 12/1996 | Ruddy et al. |
| 5,602,021 A | 2/1997 | Davis et al. |
| 5,731,168 A | 3/1998 | Carter et al. |
| 5,858,351 A | 1/1999 | Podsakoff et al. |
| 5,962,313 A | 10/1999 | Podsakoff et al. |
| 6,265,389 B1 | 7/2001 | Burke |
| 6,335,011 B1 | 1/2002 | Podsakoff et al. |
| 6,372,205 B1 | 4/2002 | Duncan et al. |
| 6,387,674 B1 | 5/2002 | Trasciatti et al. |
| 6,479,265 B1 | 11/2002 | Napper et al. |
| 6,555,525 B2 | 4/2003 | Burke |
| 6,610,290 B2 | 8/2003 | Podsakoff et al. |
| 6,703,488 B1 | 3/2004 | Burton et al. |
| 6,855,804 B2 | 2/2005 | Paul et al. |
| 7,041,298 B2 | 5/2006 | Deshaies et al. |
| 7,105,348 B2 | 9/2006 | Murphy et al. |
| 7,223,556 B1 | 5/2007 | Zhou et al. |
| 7,335,504 B2 | 2/2008 | Haupts et al. |
| 7,371,539 B2 | 5/2008 | Church et al. |
| 7,431,923 B2 | 10/2008 | Young et al. |
| 7,442,777 B2 | 10/2008 | Young et al. |
| 7,704,492 B2 | 4/2010 | Podsakoff et al. |

(Continued)

FOREIGN PATENT DOCUMENTS

| | | | |
|---|---|---|---|
| EP | 1716232 B1 | 4/2010 | |
| EP | 1587923 B1 | 8/2011 | |

(Continued)

OTHER PUBLICATIONS

Ahmad et al., "scFv Antibody: Principles and Clinical Application," Clinical and Developmental Immunology, vol. 2012, article ID 980250, 15 pages.
Al-Lazikani et al., "Standard Conformations for the Canonical Structures of Immunoglobulins," J. Mol. Biol., 1997, 273:927-948.
Anonymous: "UNIPROT—Integrin alpha-7 precursor—Itga7—*Mus musculus* (Mouse)," Nov. 2015, https://www.uniprot.org/uniprot/Q61738.txt?version=137.

(Continued)

*Primary Examiner* — Jane J Zara
(74) *Attorney, Agent, or Firm* — FisherBroyles, LLP; Rita S. Wu; Todd R. Samelman

(57) ABSTRACT

Compositions and methods for treating enzyme-deficiency diseases are disclosed. Multidomain therapeutic proteins containing an internalization effector binding domain and a lysosomal replacement enzyme activity are disclosed. The multidomain therapeutic proteins are capable of entering cells, segregating to the lysosome, and delivering the replacement enzyme activity to the lysosome.

20 Claims, 18 Drawing Sheets

Figure 1A:
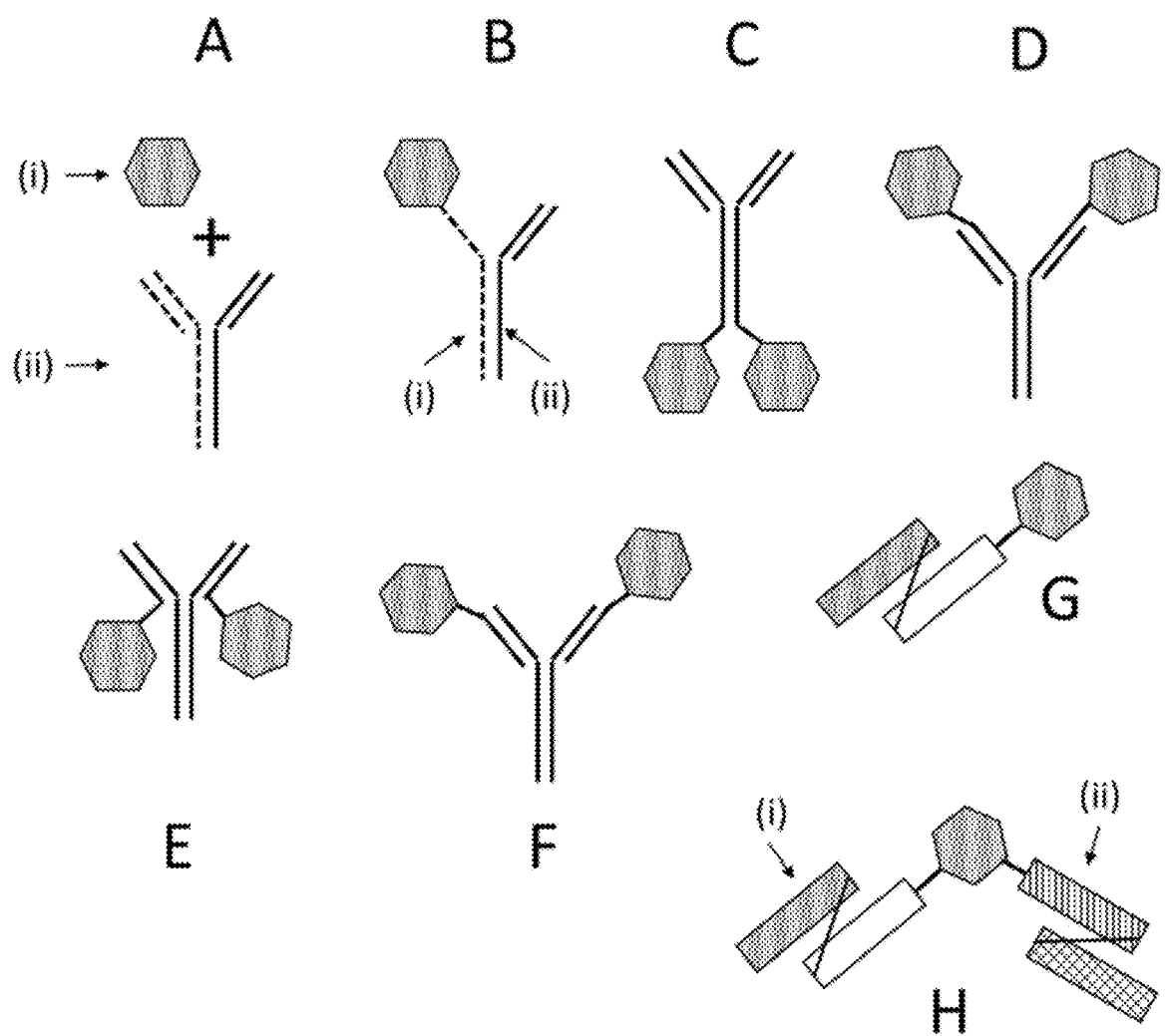

Specification includes a Sequence Listing.

(56) References Cited

U.S. PATENT DOCUMENTS

| | | |
|---|---|---|
| 7,785,856 B2 | 8/2010 | LeBowitz et al. |
| 7,858,367 B2 | 12/2010 | Amalfitano et al. |
| 8,048,991 B2 | 11/2011 | Lundgren-Åkerlund |
| 8,257,745 B2 | 9/2012 | Ketelson et al. |
| 8,278,036 B2 | 10/2012 | Kariko et al. |
| 8,563,255 B2 | 10/2013 | Lundgren-Åkerlund |
| 8,642,835 B2 | 2/2014 | Macdonald et al. |
| 8,679,478 B2 | 3/2014 | Koeberl |
| 8,785,168 B2 | 7/2014 | LeBowitz et al. |
| 9,186,420 B2 | 11/2015 | Koeberl |
| 9,453,241 B2 * | 9/2016 | Pan ................. C07K 14/705 |
| 9,545,450 B2 | 1/2017 | Do |
| 9,622,459 B2 | 4/2017 | Macdonald et al. |
| 9,738,717 B2 | 8/2017 | Azorsa |
| 9,849,195 B2 | 12/2017 | Davidson |
| 9,873,868 B2 | 1/2018 | Koeberl et al. |
| 10,017,581 B2 * | 7/2018 | Armstrong ............ A61K 9/0019 |
| 10,087,253 B2 | 10/2018 | Lundgren-Åkerlund |
| 10,098,905 B2 | 10/2018 | Koeberl |
| 10,293,000 B2 | 5/2019 | Rebar |
| 10,512,676 B2 | 12/2019 | Char et al. |
| 10,556,015 B2 | 2/2020 | Zhang et al. |
| 10,759,864 B2 | 9/2020 | Sonoda et al. |
| 10,857,212 B2 | 12/2020 | Do et al. |
| 10,869,906 B2 | 12/2020 | Kishnani et al. |
| 10,912,804 B2 | 2/2021 | Byrne et al. |
| 2003/0219415 A1 | 11/2003 | Podsakoff et al. |
| 2004/0204379 A1 | 10/2004 | Cheng et al. |
| 2004/0248262 A1 | 12/2004 | Koeberl et al. |
| 2004/0258666 A1 | 12/2004 | Passini et al. |
| 2005/0220766 A1 | 10/2005 | Amalfitano et al. |
| 2005/0244400 A1 | 11/2005 | LeBowitz et al. |
| 2006/0078542 A1 | 4/2006 | Mah et al. |
| 2006/0099184 A1 | 5/2006 | Podsakoff et al. |
| 2006/0171926 A1 | 8/2006 | Passini et al. |
| 2006/0210474 A1 | 9/2006 | Young et al. |
| 2007/0280945 A1 | 12/2007 | Stevens et al. |
| 2008/0044408 A1 | 2/2008 | Young et al. |
| 2008/0069803 A1 | 3/2008 | Podsakoff et al. |
| 2008/0089891 A1 | 4/2008 | Hahn et al. |
| 2008/0269149 A1 | 10/2008 | Bowles et al. |
| 2008/0279945 A1 | 11/2008 | Mah et al. |
| 2009/0117091 A1 | 5/2009 | LeBowitz et al. |
| 2009/0155262 A1 | 6/2009 | Young et al. |
| 2009/0191178 A1 | 7/2009 | Zankel et al. |
| 2010/0221225 A1 | 9/2010 | Byrne et al. |
| 2010/0331527 A1 | 12/2010 | Davis et al. |
| 2011/0184049 A1 * | 7/2011 | Chuah ................ C07K 14/8121 |
| | | 514/44 R |
| 2011/0223147 A1 | 9/2011 | Lebowitz et al. |
| 2012/0034625 A1 | 2/2012 | Lundgren-Åkerlund |
| 2012/0093794 A1 | 4/2012 | LeBowitz et al. |
| 2012/0183502 A1 | 7/2012 | Meeker et al. |
| 2012/0228565 A1 | 9/2012 | Adams et al. |
| 2012/0265001 A1 | 10/2012 | Asmatulu et al. |
| 2012/0283503 A1 | 11/2012 | Ostrovska et al. |
| 2012/0322861 A1 | 12/2012 | Byrne et al. |
| 2013/0243775 A1 | 9/2013 | Papadopoulos et al. |
| 2013/0267473 A1 | 10/2013 | Piens et al. |
| 2014/0099716 A1 | 4/2014 | Lundgren-Åkerlund |
| 2014/0186326 A1 | 7/2014 | Canfield et al. |
| 2014/0356366 A1 | 12/2014 | Cheong et al. |
| 2015/0196671 A1 | 7/2015 | Byrne et al. |
| 2016/0089451 A1 | 3/2016 | Armstrong |
| 2016/0115229 A1 | 4/2016 | Azorsa |
| 2016/0319023 A1 | 11/2016 | Lundgren-Åkerlund |
| 2016/0369297 A1 | 12/2016 | Byrne et al. |
| 2017/0028002 A1 | 2/2017 | Byrne et al. |
| 2017/0189497 A1 | 7/2017 | Do et al. |
| 2018/0028676 A1 | 2/2018 | Armstrong |
| 2018/0036388 A1 | 2/2018 | McIvor et al. |
| 2018/0125949 A1 | 5/2018 | LeBowitz et al. |
| 2018/0236105 A1 | 8/2018 | Davidson et al. |
| 2018/0251571 A1 | 9/2018 | Armstrong et al. |
| 2018/0264090 A1 | 9/2018 | McIvor et al. |
| 2018/0271956 A1 | 9/2018 | McIvor et al. |
| 2018/0371440 A1 | 12/2018 | Koeberl et al. |
| 2019/0030059 A1 | 1/2019 | Koeberl |
| 2019/0112588 A1 | 4/2019 | Baik et al. |
| 2019/0224246 A1 | 7/2019 | Rebar |
| 2019/0241633 A1 | 8/2019 | Fotin-Mleczek et al. |
| 2019/0269797 A1 | 9/2019 | Davidson et al. |
| 2019/0390184 A1 | 12/2019 | Mingozzi et al. |
| 2019/0390225 A1 | 12/2019 | Mingozzi et al. |
| 2020/0009267 A1 | 1/2020 | Davidson et al. |
| 2020/0248205 A1 | 8/2020 | Kirn et al. |
| 2020/0317798 A1 | 10/2020 | Sonoda et al. |
| 2020/0407746 A1 | 12/2020 | Vandendriessche et al. |
| 2021/0038739 A1 | 2/2021 | Takahashi et al. |
| 2021/0040503 A1 | 2/2021 | Mingozzi et al. |

FOREIGN PATENT DOCUMENTS

| | | |
|---|---|---|
| EP | 1879624 B1 | 9/2011 |
| EP | 2420256 B1 | 2/2012 |
| EP | 1620133 B1 | 12/2015 |
| EP | 2475376 B1 | 3/2016 |
| EP | 2279210 B1 | 4/2017 |
| EP | 2861263 B1 | 12/2017 |
| EP | 2269658 B1 | 12/2018 |
| EP | 2687597 B1 | 12/2018 |
| EP | 3075386 B1 | 10/2019 |
| EP | 3292875 B1 | 5/2020 |
| EP | 2981551 B1 | 6/2020 |
| EP | 3272773 B1 | 7/2020 |
| EP | 3461905 B1 | 8/2020 |
| WO | 1997/005266 A1 | 2/1997 |
| WO | 1998/016254 A1 | 4/1998 |
| WO | 2004/023973 A2 | 3/2004 |
| WO | 2005/077333 A2 | 8/2005 |
| WO | 2006/108052 A2 | 10/2006 |
| WO | 2007/024323 A2 | 3/2007 |
| WO | 2009/094561 A1 | 7/2009 |
| WO | 2011/012316 A2 | 2/2011 |
| WO | 2011/029823 A1 | 3/2011 |
| WO | 2012/125987 A2 | 9/2012 |
| WO | 2003/057179 A2 | 7/2013 |
| WO | 2014/185908 A2 | 11/2014 |
| WO | 2015/026907 A1 | 2/2015 |
| WO | 2016/044947 A1 | 3/2016 |
| WO | 2016/065319 A1 | 4/2016 |
| WO | 2016/085820 A1 | 6/2016 |
| WO | 2017/100467 A2 | 6/2017 |
| WO | 2017/134197 A1 | 8/2017 |
| WO | 2018/138322 A1 | 8/2018 |
| WO | 2018/213340 A1 | 11/2018 |
| WO | 2019/153009 A1 | 8/2019 |
| WO | 2019/157224 A1 | 8/2019 |
| WO | 2019/222411 A1 | 11/2019 |
| WO | 2020/028841 A1 | 2/2020 |
| WO | 2020/102645 A1 | 5/2020 |
| WO | 2020/117898 A1 | 6/2020 |

OTHER PUBLICATIONS

Anzai et al., "c-kit associated with the transmembrane 4 superfamily proteins constitutes a functionally distinct subunit in human hematopoietic progenitors," Blood, 2002, 99(12):4413-4421, doi:10.1182/blood.V99.12.4413.

Arnold et al. "Metabolic Biotinylation Provides a Unique Platform for the Purification and Targeting of Multiple AAV Vector Serotypes," Molecular Therapy, 14(1):97-106.

Arribas and Cutler, "Weibel-Palade Body Membrane Proteins Exhibit Differential Trafficking After Exocytosis in Endothelial Cells," Traffic, 2000, 1:783-793.

Aurnhammer et al., "Universal Real-Time PCR for the Detection and Quantification of Adeno-Associated Virus Serotype 2-Derived Inverted Terminal Repeat Sequences," Hum. Gene Ther. Methods, Part B, 2012, 23:18-28.

Baik et al., "Next-generation antibody-guided enzyme replacement therapy in Pompe disease mice," Molecular Genetics and Metabolism, 2018, 123(2):S21 Abstract Only.

(56) References Cited

OTHER PUBLICATIONS

Banerjee et al., "Targeted and armed oncolytic adenovirus via chemoselective modification," Bioorganic and Medicinal Chemistry Letters, 2011, 21(17):4985-4988.
Bareford and Swaan, "Endocytic mechanisms for targeted drug delivery," Advanced Drug Delivery Reviews, Elsevier, Amsterdam, NL, 2007, 59(8):748-758.
Bartlett et al., "Infectious Entry Pathway of Adeno-Associated Virus and Adeno-Associated Virus Vectors," Journal of Virology, 2000, 74(6):2777-2785.
Barzel et al., "Promoterless gene targeting without nucleases ameliorates haemophilia B in mice," Nature, 2015, 517(7534):360-364.
Battig et al., "Programmable Release of Multiple Protein Drugs from Aptamer-Functionalized Hydrogels via Nucleic Acid Hybridization," J. Am. Chem. Society., 2012, 134:12410-12413.
Beatty et al., "Trafficking from CD63-positive late endocytic multivesicular bodies is essential for intracellular development of *Chlamydia trachomatis*," Journal of Cell Science, 2006, 119(2):350-359.
Berditchevski et al., "Specific Association of CD63 with the VLA-3 and VLA-6 Integrins," Journal of Biological Chemistry, 1995, 270(30):17784-17790.
Berditchevski et al., "Characterization of Novel Complexes on the Cell Surface between Integrins and Proteins with 4 Transmembrane Domains (TM4 proteins)," Molecular Biology of the Cell, 1996, 7:193-207.
Berditchevski et al., "A Novel Link between Integrins, Transmembrane-4 Superfamily Proteins (CD63 and CD81), and Phosphatidylinositol 4-Kinase*," Journal of Biological Chemistry, Jan. 1997, 272(5):2595-2598.
Berditchevski et al., "Generation of Monoclonal Antibodies to Integrin-associated Proteins," Journal of Biological Chemistry, Nov. 1997, 272(46):29174-29180.
Berditchevski et al., "Expression of the Palmitoylation-deficient CD151 Weakens the Association of $\alpha 3\beta 1$ Integrin with the Tetraspanin-enriched Microdomains and Affects Integrin-dependent Signaling*," Journal of Biological Chemistry, 2002, 277(40):36991-37000.
Berger et al., "Fusion protein technologies for biopharmaceuticals: Applications and challenges," mAbs, 2015, 7(3):456-460.
Bian et al., "Selective gene transfer in vitro to tumor cells via recombinant Newcastle disease virus," Cancer Gene Ther., 2005, 12:295-303.
Bian et al., "In vivo efficacy of systemic tumor targeting of a viral RNA vector with oncolytic properties using a bispecific adapter protein," Int. J. Oncol., 2005, 29:1359-1369.
Blechacz and Russell, "Measles Virus as an Oncolytic Vector Platform," Current Gene Therapy, 2008, 8:162-175.
Boado et al., "IgG-Enzyme Fusion Protein: Pharmacokinetics and Anti-Drug Antibody Response in Rhesus Monkeys," Bioconjugate Chemistry, 2013, 24(1):97-104.
Bode et al., "Antibody-Directed Fibrinolysis: An Antibody Specific for Both Fibrin and Tissue Plasminogen Activator," Journal of Biological Chemistry, Jan. 1989, 264(2):944-948.
Bonardi et al., "Delivery of Saporin to Human B-Cell Lymphoma Using Bispecific Antibody: Targeting via CD22 but not CD19, CD37, or Immunoglobulin Results in Efficient Killing," Cancer Research, Jul. 1993, 53(13):3015-3021.
Boustany, "Lysosomal storage diseases—the horizon expands," Nat. Rev. Neurol., Oct. 2013, 9(10):583-598.
Burkin and Kaufman, "The $\alpha 7\beta 1$ integrin in muscle development and disease," Cell Tissue Res., 1999, 296:183-190.
Campadelli-Fiume et al., "Rethinking herpes simplex virus: the way to oncolytic agents," Reviews in Medical Virology, 2011, 21:213-226.
Catelas et al., "Controlled Release of Bioactive Transforming Growth Factor Beta-1 from Fibrin Gels In Vitro," Tissue Engineering: Part C, 2008, 14(2):119-128.
Chadwick et al., "Modification of Retroviral Tropism by Display of IGF-I," Journal of Molecular Biology, 1999, 285:485-494.

Chen et al., "Fusion Protein Linkers: Property, Design and Functionality," Adv Drug Deliv Rev., 2013, 65(10):1357-1369.
Chiba, "Molecular Mechanism in $\alpha$-Glucosidase and Glucoamylase," Biosci. Biotechnol. Biochem., 1997, 61(8):1233-1239.
Chuah et al., "Liver-Specific Transcriptional Modules Identified by Genome-Wide In Silico Analysis Enable Efficient Gene Therapy in Mice and Non-Human Primates," Mol. Ther., 2014, 22(9):1605-1613.
Clevenger and Kline, "Prolactin receptor signal transduction," 10(10) Lupus, (2001) 10:706-718.
Dalba et al., "Beyond Oncolytic Virotherapy: Replication-Competent Retrovirus Vectors for Selective and Stable Transduction of Tumors," Current Gene Therapy, 2005, 5:655-667.
Darvish-Damavandi et al., "Towards the development of an enzyme replacement therapy for the metabolic disorder propionic acidemia," Molecular Genetics and Metabolism Reports, 2016, 8(1):51-60.
De Goeij et al., "Efficient Payload Delivery by a Bispecific Antibody-Drug Conjugate Targeting HER2 and CD63," Mol. Cancer Ther., 2016, 15(11):2688-2697.
De Franceschi et al., "Integrin traffic—the update," Journal of Cell Science, 2015, 128(5):839-852.
Derosa et al., "Therapeutic efficacy in a hemophilia B model using a biosynthetic mRNA liver depot system," Gene Therapy, 2016, 23:699-707.
Desnick and Schuchman, "Enzyme replacement therapy for lysosomal diseases: lessons from 20 years of experience and remaining challenges," 13 Annu. Rev. Genomics Hum. Genet., 2012, 13:307-335.
Dhital et al., "Mammalian Mucosal $\alpha$-Glucosidases Coordinate with $\alpha$-Amylase in the Initial Starch Hydrolysis Stage to Have a Role in Starch Digestion Beyond Glucogenesis," PLoS One, 2013, 8(4):e62546, 13 pages.
Dimauro and Spiegel, "Progress and problems in muscle glycogenosis," Acta Myologica, Oct. 2011, 30(2):96-102.
Doyle et al., "CD63 is an essential cofactor to leukocyte recruitment by endothelial P-selectin," Blood, 2011, 118(15):4265-427.
Duffield et al., "The tetraspanin CD63 enhances the internalization of the H,K-ATPase $\beta$-subunit," Proc. Nail. Acad. Sci. USA, Dec. 2003, 100(26):15560-15565.
Egea et al., "Tissue inhibitor of metalloproteinase-1 (TIMP-1) regulates mesenchymal stem cells through let-7f microRNA and Wnt/$\beta$-catenin signaling," PNAS, 2012, 109(6):E309-E316.
Einfeld, et al., "Reducing the Native Tropism of Adenovirus Vectors Requires Removal of both CAR and Integrin Interactions," J. Virol., 2001, 75(23):11284-11291.
Engering and Pieters, "Association of distinct tetraspanins with MHC class II molecules at different subcellular locations in human immature dendritic cells," International Immunology, 2001, 13(2):127-134.
Erlwein et al., "Chimeric Ecotropic MLV Envelope Proteins that Carry EGF Receptor-Specific Ligands and the Pseudomonas Exotoxin A Translocation Domain to Target Gene Transfer to Human Cancer Cells," Virology, 2002, 302:333-341.
Ferland et al., "The effect of chloroquine on lysosomal prolactin receptors in rat liver," Endocrinology, 1984, 115(5):1842-1849.
Flannery et al., "Palmitoylation-dependent association with CD63 targets the CA2+ sensor synaptotagmin VII to lysosomes," J. Cell Biol., Nov. 2010, 191(3):599-613.
Fuller et al., "Isolation and characterisation of a recombinant, precursor form of lysosomal acid alpha-glucosidase," European Journal of Biochemistry, 1995, 234(3):903-909.
Galanis, "Therapeutic Potential of Oncolytic Measles Virus: Promises and Challenges," Clinical Pharmacology and Therapeutics, 2010, 88(5):620-625.
Galmiche et al., "Expression of a functional single chain antibody on the surface of extracellular enveloped vaccinia virus as a step towards selective tumour cell targeting," Journal of General Virology, 1997, 78:3019-3027.
Gao et al., "Novel adeno-associated viruses from rhesus monkeys as vectors for human gene therapy," PNAS, 2002, 99(18):11854-11859.

(56) References Cited

OTHER PUBLICATIONS

Genty et al., "Endocytosis and degradation of prolactin and its receptor in Chinese hamster ovary cells stably transfected with prolactin receptor cDNA," Mol. Cell Endocrinol., 1994, 99(2):221-228.
Ghaderi et al., "Production platforms for biotherapeutic glycoproteins. Occurrence, impact, and challenges of non-human sialylation," Biotechnol. Genet. Eng. Rev., 2012, 28:147-175.
Ghosh et al., "An Endocytosed TGN38 Chimeric Protein is Delivered to the TGN after Trafficking Through the Endocytic Recycling Compartment in CHO Cells," J. Cell Bioi., Aug. 1998, 142(4):923-936.
Gigout et al., "Altering AAV Tropism with Mosaic Viral Capsids," Molecular Therapy, 2005, 11(6):856-865.
Girod et al., "Genetic capsid modifications allow efficient re-targeting of adeno-associated virus type 2," Nature Medicine, 1999, 5(9):1052-1056.
Glasgow et al., "A Strategy for Adenovirus Vector Targeting with a Secreted Single Chain Antibody," PLOS One, 2009, 4(12):e8355, 12 pages.
Gray et al., "Production of recombinant adeno-associated viral vectors and use in vitro and in vivo administration", Current Protocols in Neuroscience, 2011, Chapter: Unit 4.17, 36 pages, doi:10.1002/0471142301.ns0417s57.
Grifman et al., "Incorporation of Tumor-Targeting Peptides into Recombinant Adeno-associated Virus Capsids," Molecular Therapy, 2001, 3(6):964-975.
Guse et al., "Oncolytic vaccinia virus for the treatment of cancer," Expert Opinion on Biological Therapy, 2011, 11(5):595-608.
Haijema et al., "Switching Species Tropism: an Effective Way to Manipulate the Feline Coronavirus Genome," J. Virol., 2003, 77(8):4528-4538.
Haijema et al., "Live, Attenuated Coronavirus Vaccines through the Directed Deletion of Group-Specific Genes Provide Protection against Feline Infectious Peritonitis," J. Virology, 2004, 78(8):3863-3871.
Hakomori, "Glycosphingolipids in Cellular Interaction, Differentiation, and Oncogenesis," Annual Review of Biochemistry, Jul. 1981, 50:733-764.
Hammond et al., "Single-Chain Antibody Displayed on a Recombinant Measles Virus Confers Entry through the Tumor-Associated Carcinoembryonic Antigen," Journal of Virology, 2001, 75(5):2087-2096.
Hemler et al., (2008) "Targeting of tetraspanin proteins—potential benefits and strategies," Nat. Rev. Drug. Discov. 7(9):747-758, doi:10.1038/nrd2659.
Hemminki et al., "Targeting Oncolytic Adenoviral Agents to the Epidermal Growth Factor Pathway with a Secretory Fusion Molecule," Cancer Res., 2001, 61: 6377-6381.
Henning et al., "Genetic Modification of Adenovirus 5 Tropism by a Novel Class of Ligands Based on a Three-Helix Bundle Scaffold Derived from Staphylococcal Protein A," Human Gene Therapy, 2002, 13:1427-1439.
Hesselink et al., "Lysosomal dysfunction in muscle with special reference to glycogen storage disease type II," Biochim. Biophys. Acta., 2003, 1637(2):164-170.
Hirst et al., "Characterization of a Fourth Adaptor-related Protein Complex," Molecular Biology of the Cell, 1999, 10:2787-2802.
Holliger et al., ""Diabodies": Small bivalent and bispecific antibody fragments," PNAS USA, 1993, 90:6444-6448.
Huie et al., "Increased Occurrence of Cleft Lip in Glycogen Storage Disease Type II (GSDII): Exclusion of a Contiguous Gene Syndrome in Two Patients by Presence of Intragenic Mutations Including a Novel Nonsense Mutation Gln58Stop," Am. J. Med. Genet., 1999, 85(1):5-8.
Huie et al., "Glycogen Storage Disease Type II: Identification of Four Novel Missense Mutations (D645N, G648S, R672W, R672Q) and Two Insertions/Deletions in the Acid α-Glucosidase Locus of Patients of Differing Phenotype," Biochem. Biophys. Res. Commun., 1998, 244(3):921-927.
Kabat et al., (1991) "Tabulation and Analysis of Amino Acid and Nucleic Acid Sequences of Precursors, V-Regions, C-Regions, J-Chain, T-Cell Receptors for Antigen, T-Cell Surface Antigens, alpha2-Microglobulins, Major Histocompatibility Antigens, Thy-1, Complement, C-Reactive Protein, Thymopoietin, Integrins, Post-gamma Globulin, a 2-Macroglobulins, and Other Related Proteins", Sequences of Proteins of Immunological Interest, Fifth Edition; NIH Publication No. 91-3242, National Institutes of Health, Bethesda, Md. (37 pages).
Kidd et al., "Fibrin hydrogels for lentiviral gene delivery in vitro and in vivo," Journal of Controlled Release, 2012, 157(1):80-85.
Kitani et al., "A Cell Surface Glycoprotein of Rat Basophilic Leukemia Cells Close to the High Affinity IgE Receptor (FcεRI)," Journal of Biological Chemistry, 1991, 266(3):1903-1909.
Klimstra et al., "Targeting Sindbis virus-based vectors to Fc receptor-positive cell types," Virology, 2005, 338:9-21.
Kobayashi et al., "The Tetraspanin CD63/lamp3 Cycles between Endocytic and Secretory Compartments in Human Endothelial Cells," Molecular Biology, May 2000, 11:1829-1843.
Koeberl et al., "Enhanced efficacy of enzyme replacement therapy in Pompe disease through mannose-6-phosphate receptor expression in skeletal muscle," Mol. Genet. Metab., 2011, 103(2):107-112.
Kraft et al., "The tetraspanin CD63 is required for efficient IgE-mediated mast cell degranulation and anaphylaxis," J. Immunol, 2013, 191(6):2871-2878.
Latysheva et al., "Syntenin-1 Is a New Component of Tetraspanin-Enriched Microdomains: Mechanisms and Consequences of the Interaction of Syntenin-1 with CD63," Molecular and Cellular Biology, Oct. 2006, 26(20):7707-7718.
Lee et al., "Impaired Retrograde Membrane Traffic Through Endosomes in a Mutant CHO Cell Defective in Phosphalidyl Serine Synthesis," Genes to Cells, 2012, 17:728-736.
Lekishvili et al., "The tumour-associated antigen L6 (L6-Ag) is recruited to the tetraspanin-enriched microdomains: implication for tumour cell motility," Journal of Cell Science, 2008, 121(5):685-694, doi:10.1242/jcs.020347.
Lieu et al., "The Golgin GCC88 Is Required for Efficient Retrograde Transport of Cargo from the Early Endosomes to the Trans-Golgi Network," Mol. Bioi. Cell, Dec. 2007, 18:4979-4991.
Maecker et al., "The tetraspanin superfamily: molecular facilitators," FASEB J., May 1997, 11(6)428-442.
Maesner et al., "Established cell surface markers efficiently isolate highly overlapping populations of skeletal muscle satellite cells by fluorescence-activated cell sorting," Skeletal Muscle, 2016, 6:35 (10 pages).
Maga et al., "Glycosylation-independent Lysosomal Targeting of Acid α-Glucosidase Enhances Muscle Glycogen Clearance in Pompe Mice," J. Biol. Chem., 2013, 288(3):1428-1438.
Mantegazza et al., "CD63 Tetraspanin Slows Down Cell Migration and Translocates to the Endosomal-Lysosomal- MIICs Route after Extracellular Stimuli in Human Immature Dendritic Cells," Blood, Aug. 2004, 104(4):1183-1190.
Martin et al., "Modeling antibody hypervariable loops: A combined algorithm," Proc. Natl. Acad. Sci. USA, 1989, 86:9268-9272.
Metzelaar et al., "CD63 antigen. A novel lysosomal membrane glycoprotein, cloned by a screening procedure for intracellular antigens in eukaryotic cells," J. Biol. Chem., 1991, 266(5):3239-3245.
Muenzer, "Early initiation of enzyme replacement therapy for the mucopolysaccharidoses," Mol. Genet. Metab., Feb. 2014, 111(2):63-72.
Nakamura and Russell "Oncolytic measles viruses for cancer therapy," Expert Opinion on Biological Therapy, 2004, 4(10):1685-1692.
Nakano et al., "Herpes Simplex Virus Targeting to the EGF Receptor by a gD-Specific Soluble Bridging Molecule," Mol. Ther., Apr. 2005, 11(4):617-624.
Nicklin and Baker, "Tropism-Modified Adenoviral and Adeno-Associated Viral Vectors for Gene Therapy," Curr. Gene Ther., 2002, 2:273-293.
Nishibori et al., "The Protein CD63 Is in Platelet Dense Granules, Is Deficient in a Patient with Hermansky-Pudlak Syndrome, and Appears Identical to Granulophysin," J. Clin. Invest., 1993, 91(4):1775-1782.

(56) References Cited

OTHER PUBLICATIONS

Nishida-Aoki et al., "Disruption of Circulating Extracellular Vesicles as a Novel Therapeutic Strategy against Cancer Metastasis," Molecular Therapy, 2017, 25(1):181-191.
Nishiyama et al., "Akt inactivation induces endoplasmic reticulum stress-independent autophagy in fibroblasts from patients with Pompe disease," Molecular Genetics and Metabolism, 2012, 107:490-495.
Ohno et al., "Cell-specific targeting of Sindbis virus vectors displaying IgG-binding domains of protein A," Nature Biotechnology, 1997, 15:763-767.
Oka and Bulleid, "Forming disulfides in the endoplasmic reticulum," Biochim Biophys Acta, 2013, 1833(11):2425-2429.
Pacak et al. "Tissue specific promoters improve specificity of AAV9 mediated transgene expression following intra-vascular gene delivery in neonatal mice," Genetic Vaccines and Therapy, 2008 6:13 (5 pages).
Papapetrou and Schambach, "Gene Insertion Into Genomic Safe Harbors for Human Gene Therapy," J. Molecular Therapy, Apr. 2016, 24(4):678-684.
Park et al., "Cancer gene therapy using adeno-associated virus vectors," Frontiers in Bioscience, Jan. 2008, 13:2653-2659.
Park et al., "Epidermal growth factor (EGF) receptor targeted delivery of PEGylated adenovirus," Biochemical and Biophysical Research Communications, 2008, 366:769-774.
Paul et al., "Specific Tumor Cell Targeting by a Recombinant MVA Expressing a Functional Single Chain Antibody on the Surface of Intracellular Mature Virus (IMV) Particles," Viral Immunology, 2007, 20(4):664-671.
Pereboeva et al., "Targeting EGFR with metabolically biotinylated fiber-mosaic adenovirus," Gene Therapy, 2007, 14(8):627-637.
Pizzato et al., "Evidence for nonspecific adsorption of targeted retrovirus vector particles to cells," Gene Therapy, 2001, 8:1088-1096
Poljak et al., "Production and structure of diabodies," Structure, 1994, 2:1121-1123.
Pols and Klumperman, "Trafficking and Function of the Tetraspanin CD63," Exp. Cell Res., Oct. 2009, 315:1584-1592.
Ponnazhagan et al., "Conjugate-Based Targeting of Recombinant Adeno-Associated Virus Type 2 Vectors by Using Avidin-Linked Ligands," J. Virol., 2002, 76(24):12900-12907.
Prabakaran et al., "Mannose 6-Phosphate Receptor and Sortilin Mediated Endocytosis of α-Galactosidase A in Kidney Endothelial Cells," PLoS One, 2012, 7(6):e39975, 9 pages.
Quetglas et al., "Alphavirus vectors for cancer therapy," Virus Research, 2010, 153:179-196.
Quezada-Calvillo et al., "Luminal Starch Substrate "Brake" on Maltase-Glucoamylase Activity is Located within the Glucoamylase Subunit," Journal of Nutrition, 2008, 138(4):685-692.
Raben et al., "Enzyme replacement therapy in the mouse model of Pompe disease," Molecular Genetics and Metabolism, 2003, 80:159-169.
Rous et al., "Role of Adaptor Complex AP-3 in Targeting Wild-Type and Mutated CD63 to Lysosomes," Molecular Biology of the Cell, Mar. 2002, 13:1071-1082.
Rubinstein et al., "CD9, CD63, CD81, and CD82 are components of a surface tetraspan network connected to HLA-DR and VLA integrins," Eur. J. Immunol., 1996, 26:2657-2665.
Russell and Cosset, "Modifying the Host Range Properties of Retroviral Vectors," Journal of Gene Medicine, 1999, 1:300-311.
Russell and Peng, "Measles virus for cancer therapy," Current Topics in Microbiology and Immunology, 2009, 330:213-241.
Sasisekharan et al., "Glycomics Approach to Structure-Function Relationships of Glycosaminoglycans," Ann. Rev. Biomed. Eng., Dec. 2014, 8(1):181-231.
Schänzer et al., "Quantification of muscle pathology in infantile Pompe disease," Neuromuscular Disorders, 2017, 27:141-152.
Schröoder et al., "Deficiency of the Tetraspanin CD63 Associated with Kidney Pathology but Normal Lysosomal Function," Mol. Cell. Biol., 2009, 29(4):1083-1094.
Shah and Breakefield, "HSV Amplicon Vectors for Cancer Therapy," Current Gene Therapy, 2006, 6:361-370.
Shen et al., "A map of the cis-regulatory sequences in the mouse genome," Nature, 2012, 488(7409):116-120, doi:10.1038/nature11243.
Shi et al., "Insertional Mutagenesis of the Adeno-Associated Virus Type 2 (AAV2) Capsid Gene and Generation of AAV2 Vectors Targeted to Alternative Cell-Surface Receptors," Human Gene Therapy, 2001, 12:1697-1711.
Shi and Bartlett, "RGD Inclusion in VP3 Provides Adeno-Associated Virus Type 2 (AAV2)-Based Vectors with a Heparan Sulfate-Independent Cell Entry Mechanism," Molecular Therapy, Apr. 2003, 7(4):515-525.
Shields et al., "Lack of Fucose on Human IgG1 N-Linked Oligosaccharide Improves Binding to Human Fc RIII and Antibody-dependent Cellular Toxicity," Journal of Biological Chemistry, 2002, 277(30):26733-26740.
Shimamoto et al., "Peptibodies: A flexible alternative format to antibodies," Mabs, 2012, 4(5):586-591.
Sim et al., "Human Intestinal Maltase-Glucoamylase: Crystal Structure of the N-Terminal Catalytic Subunit and Basis of Inhibition and Substrate Specificity," J. Mol. Biol., 2008, 375:782-792.
Skubitz et al., "CD63 associates with tyrosine kinase activity and CD11/CD18, and transmits an activation signal in neutrophils," Journal of Immunology, 1996, 157:3617-3626.
Spicer and Mikos, "Fibrin Glue as a Drug Delivery System," Journal of Controlled Release, 2010, 148(1):49-55.
Stachler and Bartlett, "Mosaic vectors comprised of modified AAV1 capsid proteins for efficient vector purification and targeting to vascular endothelial cells," Gene Ther., 2006, 13:926-931.
Stachler et al., "Site-specific Modification of AAV Vector Particles With Biophysical Probes and Targeting Ligands Using Biotin Ligase," Molecular Therapy, 2008, 16(8):1467-1473.
Tai and Kasahara, "Replication-competent retrovirus vectors for cancer gene therapy," Frontiers in Bioscience, 2008., 13:3083 3095.
Tajima et al., "Use of a Modified α-N-Acetylgalactosaminidase in the Development of Enzyme Replacement Therapy for Fabry Disease," Am. J. Hum. Genet., 2009, 85(5):569-580.
Takino et al., "Tetraspanin CD63 promotes targeting and lysosomal proteolysis of membrane-type 1 matrix metalloproteinase," Biochem. Biophys. Res. Commun., 2003, 304:160-166.
Tuli et al., "Mechanism for amyloid precursor-like protein 2 enhancement of major histocompatibility complex class I molecule degradation," J Biol Chem. 2009, 284(49):34296-34307, doi: 10.1074/jbc.M109.039727. Epub Oct. 6, 2009.
Tuma and Hubbard, "Transcytosis: Crossing Cellular Barriers," Physiological Reviews, 2003, 83(3):871-935.
Umapathysivam et al., "Correlation of acid alpha-glucosidase and glycogen content in skin fibroblasts with age of onset in Pompe disease," Clin. Chim. Acta., 2005, 361:191-198.
Van Beusechem et al., "Conditionally replicative adenovirus expressing a targeting adapter molecule exhibits enhanced oncolytic potency on CAR-deficient tumors," Gene Therapy, 2003, 10:1982-1991.
Verheije and Rottier, (2012) "Retargeting of Viruses to Generate Oncolytic Agents," Advances in Virology, 2012, 2012:1-15.
Vincent and Zurini, "Current strategies in antibody engineering: Fc engineering and pH-dependent antigen binding, bispecific antibodies and antibody drug conjugates," Biotechnol. J., 2012, 7:1444-1450.
Ward et al., "Binding activities of a repertoire of single immunoglobulin variable domains secreted from *Escherichia coli*," Nature, 1989, 341:544-546.
Wurdinger et al., "Targeting non-human coronaviruses to human cancer cells using a bispecific single-chain antibody," Gene Therapy, 2005, 12:1394-1404.
Yauch and Hemler, "Specific interactions among transmembrane 4 superfamily (TM4SF) proteins and phosphoinositide 4-kinase," Biochem. J., 2000, 351:629-637.
Yi et al., "Antibody-mediated enzyme replacement therapy targeting both lysosomal and cytoplasmic glycogen in Pompe disease," J. Mol. Med., 2017, 95(5):513-521.

(56) References Cited

OTHER PUBLICATIONS

Yoshida et al., "A CD63 Mutant Inhibits T-cell Tropic Human Immunodeficiency Virus Type 1 Entry by Disrupting CXCR4 Trafficking to the Plasma Membrane," Traffic, Feb. 2008, 9:540-558.
Zhu et al., "Conjugation of Mannose-6-Phosphate-containing Oligosaccharides to Acid α-Glucosidase Improves the Clearance of Glycogen in Pompe Mice," J. Biol. Chem., 2004, 279(48):50336-50341.
Zolotukhin et al., "Recombinant adeno-associated virus purification using novel methods improves infectious titer and yield," Gene Ther., 1999, 6:973-985.
Invitation to Pay Additional Fees with Respect to PCT/US2018/036306 dated Sep. 19, 2018.
International Search Report and Written Opinion Received for PCT/US2018/036306 dated Oct. 31, 2018.
Statement of Relatedness under MPEP 2001.06 with Respect to U.S. Appl. No. 16/001,717 dated Oct. 7, 2019.
Boado et al., "Genetic Engineering of a Lysosomal Enzyme Fusion Protein for Targeted Delivery Across the Human Blood-Brain Barrier," Biotechnology and Bioengineering, Feb. 1, 2008, 99(2):475-484.
Geel et al., "Pompe disease: Current state of treatment modalities and animal models," Molecular Genetics and Metabolism, 2007, 92:299-307.
Statement of Relatedness under MPEP 2001.06 with Respect to U.S. Appl. No. 16/001,717 dated Jan. 10, 2020.
Fuentealba et al., "Low-Density Lipoprotein Receptor-Related Protein 1 (LRP1) Mediates Neuronal Aβ42 Uptake and Lysomal Trafficking," PLoS One 5(7):e11884, pp. 1-10, Jul. 2010.
Parenti et al., "Lysomal Storage Diseases: From Pathophysiology to Therapy," Ann. Rev. Med., 66:471-486, Jan. 2015.
Statement of Relatedness under MPEP 2001.06 with Respect to U.S. Appl. No. 16/001,717 dated Jan. 19, 2021.
Baik, et al., "Targeted delivery of acid alpha-glucosidase corrects skeletal muscle phenotypes in Pompe disease mice," Biorxiv, Apr. 23, 2020; retrieved from the internet 2020-11-03 https://www.biorxiv.org/content/10.1101/2020.04.22.Q51672v1.full.pdf.
Corti et al., "Safety of Intradiaphragmatic Delivery of Adeno-Associated Virus-Mediated Alpha-Glucosidase (rAAV1-CMV-hGAA) Gene Therapy in Children Affected by Pompe Disease," Human Gene Therapy Clinical Development, 2017, 28(4):208-218.
Elmallah et al., "Sustained Correction of Motoneuron Histopathology Following Intramuscular Delivery of AAV in Pompe Mice," The American Society of Gene & Cell Therapy, Apr. 2014, 22(4):702-712.
Falk et al., "Peripheral nerve and neuromuscular junction pathology in Pompe disease," Human Molecular Genetics, 2015, 24(3):625-636.
Hordeaux et al., "Long-term neurologic and cardiac correction by intrathecal gene therapy in Pompe disease," Acta Neuropathologica Communications, 2017, 5:66 (19 pages).
Kraft et al., "Anti-CD63 antibodies suppress IgE-dependent allergic reactions in vitro and in vivo," JEM, 2005, 201(3):385-396.
Pardridge et al., "Plasma Pharmacokinetics of Valanafusp Alpha, a Human Insulin Receptor Antibody-Iduronidase Fusion Protein, in Patients with Mucopolysaccharidosis Type I," BioDrugs, 2018, 32(2):169-176.
Puzzo et al., "Rescue of Pompe disease in mice by AAV-mediated liver delivery of secretable acid α-glucosidase," Science Translational Medicine, Nov. 29, 2017, 9(418):eaam6375 (12 pages).
Sidman et al., "Temporal Neuropathological and Behavioral Phenotype of 6Neo/6Neo Pompe Disease Mice," Author Manuscript, J. Neuropathol. Exp. Neurol., Aug. 2008, 67(8):803-818.
White et al., "Targeted Gene Delivery to Vascular Tissue In Vivo by Tropism-Modified Adeno-Associated Virus Vectors," Circulation, 2004,109:513-519.
Statement of Relatedness under MPEP 2001.06 with Respect to U.S. Appl. No. 16/001,717 dated Jul. 8, 2021.

\* cited by examiner

COMPOSITIONS AND METHODS FOR INTERNALIZING ENZYMES

CROSS-REFERENCE TO RELATED APPLICATIONS

This application claims the benefit under 35 U.S.C. § 119(e) of U.S. Provisional Nos. 62/673,098, filed May 17, 2018; 62/574,719 filed Oct. 19, 2017; and 62/516,656 filed Jun. 7, 2017, each of which is hereby incorporated in their entireties by reference.

FIELD OF THE INVENTION

This application is generally directed to compositions and methods for treating lysosomal storage diseases. This application is directed specifically to targeted protein complexes that contain replacement enzymes and their use in treating lysosomal storage diseases.

BACKGROUND

Lysosomal storage diseases are a class of rare diseases that affect the degradation of myriad substrates in the lysosome. Those substrates include sphingolipids, mucopolysaccharides, glycoproteins, glycogen, and oligosaccharides, which can accumulate in the cells of those with disease leading to cell death. Organs affected by lysosomal storage diseases include the central nervous system (CNS), the peripheral nervous system (PNS), lungs, liver, bone, skeletal and cardiac muscle, and the reticuloendothelial system.

Options for the treatment of lysosomal storage diseases include enzyme replacement therapy (ERT), substrate reduction therapy, pharmacological chaperone-mediated therapy, hematopoietic stem cell transplant therapy, and gene therapy. An example of substrate reduction therapy includes the use of Miglustat or Eliglustat to treat Gaucher Type 1. These drugs act by blocking synthase activity, which reduces subsequent substrate production. Hematopoietic stem cell therapy (HSCT), for example, is used to ameliorate and slow-down the negative central nervous system phenotype in patients with some forms of MPS. See R. M. Boustany, "Lysosomal storage diseases—the horizon expands," 9(10) Nat. Rev. Neurol. 583-98, October 2013. Table 1 lists some lysosomal storage diseases and their associated enzymes or other proteins.

TABLE 1

| Lysosomal Storage Diseases | | |
| --- | --- | --- |
| Class | Disease | Involved Enzyme/Protein |
| Sphingolipidoses | Fabry disease | α-Galactosidase A |
| | Farber lipogranulomatosis | Ceramidase |
| | Gaucher disease type I | β-Glucosidase |
| | Gaucher disease types II and III | Saposin-C activator |
| | Niemann-Pick diseases types A and B | Sphingomyelinase |
| | GM1-gangliosidosis | β-Galactosidase |
| | GM2-gangliosidosis (Sandhoff) | β-Hexosaminidase A and B |
| | GM2-gangliosidosis (Tay-Sachs) | β-Hexosaminidase A |
| | GM2-gangliosidosis (GM2-activator deficiency) | GM2-activator protein |
| | GM3-gangliosidosis | GM3 synthase |
| | Metachromatic leukodystrophy | Arylsulfatase A |
| | Sphingolipid-activator deficiency | Sphingolipid activator |
| Mucopolysaccharidoses | MPS I (Scheie, Hurler-Scheie, and Hurler disease) | α-Iduronidase |
| | MPS II (Hunter) | Iduronidase-2-sulphatase |
| | MPS IIIA (Sanfilippo A) | Heparan N-sulphatase |
| | MPS IIIB (Sanfilippo B) | N-acetyl-α-glucosaminidase |
| | MPS IIIC (Sanfilippo C) | Acetyl-CoA; α-glucosamide N-acetyltransferase |
| | MPS IIID (Sanfilippo D) | N-acetylglucosamine-6-sulphatase |
| | MPS IVA (Morquio syndrome A) | N-acetylgalactosamine-6-sulphate sulphatase |
| | MPS IVB (Morquio syndrome B) | β-Galactosidase |
| | MPS VI (Maroteaux-Lamy) | N-acetylgalactosamine-4-sulphatase (arylsulphatase B) |
| | MPS VII (Sly disease) | β-Glucuronidase |
| | MPS IX | Hylauronidase |
| Glycogen storage disease | Pompe (glycogen storage disease type II) | α-Glucosidase 2 |
| Lipid metabolism | Lysosomal acid lipase deficiency (LAL-D; Wolman disease) | Lysosomal acid lipase |

Two of the most common LSDs are Pompe disease and Fabry disease. Pompe disease, which has an estimated incidence of 1 in 10,000, is caused by defective lysosomal enzyme alpha-glucosidase (GAA), which results in the deficient processing of lysosomal glycogen. Accumulation of lysosomal glycogen occurs predominantly in skeletal, cardiac, and hepatic tissues. Infantile onset Pompe causes cardiomegaly, hypotonia, hepatomegaly, and death due to cardiorespiratory failure, usually before 2 years of age. Adult onset Pompe occurs as late as the second to sixth decade and usually involves only skeletal muscle. Treatments currently available include Genzyme's MYOZYME®/LUMIZYME® (alglucosidase alfa), which is a recombinant human alpha-glucosidase produced in CHO cells and administered by intravenous infusion.

Fabry disease, which has including mild late onset cases an overall estimated incidence of 1 in 3,000, is caused by defective lysosomal enzyme alpha-galactosidase A (GLA), which results in the accumulation of globotriaosylceramide within the blood vessels and other tissues and organs. Symptoms associated with Fabry disease include pain from nerve damage and/or small vascular obstruction, renal insufficiency and eventual failure, cardiac complications such as high blood pressure and cardiomyopathy, dermatological symptoms such as formation of angiokeratomas, anhidrosis or hyperhidrosis, and ocular problems such as cornea *verticillata*, spoke-like cataract, and conjunctival and retinal vascular abnormalities. Treatments currently available include Genzyme's FABRAZYME® (agalsidase beta), which is a recombinant human alpha-galactosidase A produced in CHO cells and administered by intravenous infusion; Shire's REPLAGAL™ (agalsidase alfa), which is a recombinant human alpha-galactosidase A produced in human fibroblast cells and administered by intravenous infusion; and Amicus's GALAFOLD™ (migalastat or 1-deoxygalactonojirimycin) an orally administered small molecule chaperone that shifts the folding of abnormal alpha-galactosidase A to a functional conformation.

Current treatments for lysosomal storage diseases are less than optimal. For example, ERT generally must be administered at a high frequency and a high dose, such as biweekly and up to 40 mg/kg. Also, some replaced enzymes can be immunologically cross-reactive (CRIM), stimulating production of IgG in the subject and thus hindering delivery of the enzyme to the lysosome via the mannose-6-phosphate (M6P) receptor. The IgGs might shield the M6P residues of the replacement enzyme, and the antigen-IgG-antibody complex may be taken up into cellular lysosomes via the Fc receptor, thereby shunting the replacement enzyme preferentially to macrophages.

Delivery of replacement enzymes to the appropriate affected tissues is also inefficient (see Table 2 and Desnick & Schuchman, "Enzyme replacement therapy for lysosomal diseases: lessons from 20 years of experience and remaining challenges," 13 Annu. Rev. Genomics Hum. Genet. 307-35, 2012). For example, patients undergoing long-term enzyme replacement therapy for Infantile Pompe can still suffer from hypernasal speech, residual muscle weakness, ptosis, osteopenia, hearing loss, risk for aspiration, dysphagia, cardiac arrhythmia, and difficulty swallowing. Doses of replacement enzyme oftentimes must be increased over time to 40 mg/kg weekly or biweekly.

TABLE 2

Inefficient tissue targeting of ERT

| Disease | Subtype(s) | Easy to reach tissue | Hard to reach tissue |
|---|---|---|---|
| Gaucher disease | Type 1 | Spleen, liver, bone marrow | Bone |
|  | Types 2 and 3 | Spleen, liver, bone marrow | Bone, brain |
| Fabry disease | Classic and late onset | Vascular endothelium | Kidney, heart |
| Mucopolysaccharidoses | All | Spleen, liver, bone marrow | Bone, brain, cartilage |
| α-Mannosidosis | — | Spleen, liver, bone marrow | Bone, brain |
| Niemann-Pick disease | Type B | Spleen, liver, bone marrow | Alveolar macrophages |
| Pompe disease | Infantile | — | Heart, smooth and skeletal muscle |
|  | Later onset | — | Smooth muscle and respiratory skeletal muscle |

Endogenous mannose-6 phosphate receptor (MPR) mediates the transport of most recombinant enzymes to the lysosome. Two complementary forms of MPR exist: cation-independent (CI-MPR), and cation dependent (CD-MPR). Knock-outs of either form have missorted lysosomal enzymes. Lysosomal hydrolases are synthesized in the endoplasmic reticulum and move to the cis-Golgi network, where they are covalently modified by the addition of mannose-6-phosphate (M6P) groups. The formation of this marker depends on the sequential effect of two lysosomal enzymes: UDP-N-acetylglucosamine-1-phosphotransferase (GlcNac-phosphotransferase) and N-acetylglucosamine-1-phosphodiester-α-N-acetyl-glucosaminidase (uncovering enzyme). GlcNac-phosphotransferase catalyzes the transfer of a GlcNAc-1-phosphate residue from UDP-GlcNAc to C6 positions of selected mannoses in high-mannose type oligosaccharides of the hydrolases. Then, the uncovering enzyme removes the terminal GlcNAc, exposing the M6P recognition signal. At the trans-Golgi network, the M6P signal allows the segregation of lysosomal hydrolases from all other types of proteins through selective binding to the M6P receptors. The clathrin-coated vesicles produced bud off from the trans-Golgi network and fuse with late endosomes. At the low pH of the late endosome, the hydrolases dissociate from the M6P receptors and the empty receptors are recycled to the Golgi apparatus for further rounds of transport.

With the exception of β-glucocerebrosidase, which is delivered via the mannose receptor, recombinant lysosomal enzymes comprise M6P glycosylation and are delivered to the lysosome primarily via CI-MPR/IGF2R. Glycosylation/CI-MPR-mediated enzyme replacement delivery however does not reach all clinically relevant tissues (Table 2). Improvement to enzyme replacement therapy have centered on improving CI-MPR delivery by (i) increasing surface expression of CI-MPR using the β2-agonist clenbuterol (Koeberl et al., "Enhanced efficacy of enzyme replacement therapy in Pompe disease through mannose-6-phosphate receptor expression in skeletal muscle," 103(2) Mol. Genet. Metab. 107-12, 2011), (ii) increasing the amount of M6P residues on enzyme (Zhu et al., "Conjugation of mannose-6-phosphate-containing oligosaccharides to acid alpha-glucosidase improves the clearance of glycogen in Pompe mice," 279(48) J. Biol. Chem. 50336-41, 2004), or (iii) fusing an IGF-II domain to the enzyme (Maga et al., "Glycosylation-independent lysosomal targeting of acid alpha-glucosidase enhances muscle glycogen clearance in Pompe mice," 288(3) J. Biol. Chem. 1428-38, 2013).

A large number of lysosomal storage diseases are inadequately treated by enzyme replacement therapy or gene therapy mainly due to poor targeting of the replacement enzyme to the relevant tissue or organ, negative immunological reactions in the recipient host, and low serum half-life. A need exists for improved enzyme replacement therapies that enhance and promote better tissue biodistribution and lysosomal uptake of the enzyme. Applicant has developed an improved enzyme replacement therapy using antibody-guided delivery of enzymes to the lysosome of target affected tissues, which occurs independent of CI-MPR.

SUMMARY

Applicants have discovered that replacement enzymes can be effectively delivered into a target cell when associated with a delivery domain as part of a multidomain therapeutic protein. The multidomain therapeutic protein can be delivered to the cell, which can be ex vivo or in vivo, via a gene therapy vector, e.g., a viral vector, naked polynucleotide, polynucleotide complex, etc, comprising the coding sequence of the multidomain therapeutic protein.

In one aspect, the invention provides a polynucleotide containing a nucleic acid sequence encoding a multidomain therapeutic protein. In one embodiment, the multidomain therapeutic protein contains an enzyme domain and a delivery domain. In one embodiment, the polynucleotide also contains a viral vector nucleic acid sequence. In a specific embodiment, the polynucleotide also contains an adeno-associated virus (AAV) nucleic acid sequence.

In one embodiment, the enzyme domain has hydrolase activity, such as a glycosylase, such as a glycosidase, such as an alpha-glucosidase (GAA) or alpha-galacosidase A (GLA). In some embodiments, the enzyme domain comprises the amino acid sequence set forth as SEQ ID NO:1 or a biologically active portion thereof. In some embodiments, the enzyme domain comprises the amino acid sequence set forth as SEQ ID NO:78. In some embodiments, the enzyme domain consists essentially of the amino acid sequence set forth as SEQ ID NO:78. In some embodiments, the enzyme domain consists of the amino acid sequence set forth as SEQ ID NO:78. In one embodiment, the delivery domain is an antigen-binding protein that binds to an internalization effector. In one embodiment, the internalization effector is a cell-surface molecule that is endocytosed and trafficked to the lysosome. In a specific embodiment, the internalization effector is a CD63 molecule. In one embodiment, the internalization effector is a ITGA7 molecule. In a specific embodiment, the delivery domain is an antibody, an antibody fragment, or a single-chain variable fragment (scFv), such as an scFv that binds CD63 or ITGA7 (e.g., FIG. 1A, panel G).

In one embodiment, the multidomain therapeutic protein contains two delivery domains (e.g., FIG. 1A, panel H). In one embodiment, the first delivery domain binds an internalization effector to facilitate delivery of the enzyme to the proper target cell or target subcellular compartment; and the second delivery domain binds a transcytosis effector to facilitate the transport of the multidomain therapeutic protein across a physiological barrier such as the alveolar membrane, the liver endothelium, the blood-brain barrier, or the like. In a specific embodiment, the second delivery domain is an anti-transferrin receptor (TfR) scFv domain. In a specific embodiment, the multidomain therapeutic protein comprises a GAA enzyme domain, an anti-CD63 scFv first delivery domain, and an anti-TfR scFv second delivery domain. In another embodiment, the multidomain therapeutic protein comprises a GAA enzyme domain, an anti-ITGA7 scFv first delivery domain, and an anti-CD63 scFv second delivery domain.

In one aspect, the invention provides a gene therapy vector, such as an AAV vector, naked polynucleotide, polynucleotide complex, etc., that comprises a nucleic acid sequence encoding a multidomain therapeutic protein containing an enzyme domain and a delivery domain.

In one embodiment, the enzyme domain has hydrolase activity, such as a glycosylase, such as a glycosidase, such as an alpha-glucosidase or alpha-galacosidase A. In one embodiment, the delivery domain is an antigen-binding protein that binds to an internalization effector. In one embodiment, the internalization effector is a cell-surface molecule that is endocytosed and trafficked to the lysosome. In a specific embodiment, the internalization effector is a CD63 molecule. In one embodiment, the internalization effector is an ITGA7 molecule. In a specific embodiment, the delivery domain is an antibody, an antibody fragment, or a single-chain variable fragment (scFv), such as an scFv that binds CD63 or ITGA7.

In one aspect, the invention provides a multidomain therapeutic protein containing an enzyme domain and a delivery domain. In one embodiment, the enzyme domain has hydrolase activity, such as a glycosylase, such as a glycosidase, such as an alpha-glucosidase or alpha-galacosidase A. In one embodiment, the delivery domain is an antigen-binding protein that binds to an internalization effector. In one embodiment, the internalization effector is a cell-surface molecule that is endocytosed and trafficked to the lysosome. In a specific embodiment, the internalization effector is a CD63 molecule. In another embodiment, the internalization effector is a ITGA7 molecule. In a specific embodiment, the delivery domain is an antibody, an antibody fragment, or a single-chain variable fragment (scFv), such as an scFv that binds CD63 or ITGA7.

In one embodiment, the multidomain therapeutic protein is used to treat a patient in need of enzyme replacement therapy.

In one aspect, the invention provides a method of producing a multidomain therapeutic protein containing an enzyme domain and a delivery domain in a cell. In one embodiment, the multidomain therapeutic protein is produced by contacting the cell with a gene therapy vector comprising a nucleic acid sequence encoding the multidomain therapeutic protein. The nucleic acid sequence subsequently integrates into a genomic locus of the cell, from which the nucleic acid sequence is transcribed and translated in the case that the nucleic acid sequence is DNA, or translated in the case that the nucleic acid is RNA, and the multidomain therapeutic protein is produced. In one embodiment, the gene therapy vector is one that is commonly used in cell transfection, such as an adeno-associated virus (AAV) vector. In one embodiment, the gene therapy vector is a naked polynucleotide. In one embodiment, the gene therapy vector is a polynucleotide complex, e.g., a lipid nanoparticle. In one embodiment, the genomic locus is a safe harbor locus, which enables high expression of the multidomain therapeutic protein, while not interfering with the expression of essential genes or promoting the expression of oncogenes or other deleterious genes. In one embodiment, the genomic locus is an adeno-associated virus site.

In one embodiment, the cell is a mammalian cell, such as a human cell or a mouse cell. In one embodiment, the cell is ex vivo, such as a HEK293 cell line. In another embodiment, the cell is in vivo and the gene therapy vector containing the multidomain therapeutic protein-coding nucleic acid sequence is administered to a human or non-human subject.

In one embodiment, the enzyme domain has hydrolase activity, such as a glycosylase, such as a glycosidase, such as an alpha-glucosidase (GAA) or alpha-galacosidase A (GLA). In one embodiment, the delivery domain is an antigen-binding protein that binds to an internalization effector. In one embodiment, the internalization effector is a cell-surface molecule that is endocytosed and trafficked to the lysosome. In a specific embodiment, the internalization effector is a CD63 molecule. In a specific embodiment, the delivery domain is an antibody, an antibody fragment, or a single-chain variable fragment (scFv), such as an scFv that binds CD63 (e.g., SEQ ID NO:2). In some embodiments the multidomain therapeutic polypeptide comprises an scFv that binds CD63 (e.g., an scFv comprising the amino acid sequence set forth as SEQ ID NO:2) operably linked to GAA (set forth as SEQ ID NO:1) or a biologically active portion thereof (set forth as SEQ ID NO:78). In some embodiments, the multidomain therapeutic polypeptide comprises the sequence set forth as SEQ ID NO:10 or SEQ ID NO:79.

In a specific embodiment, an AAV vector containing a polynucleotide encoding an scFv-hydrolase fusion protein is administered to a human or non-human subject. The polynucleotide subsequently integrates at a genomic locus and the encoded fusion protein is produced. In a specific embodiment, the fusion protein is an anti-CD63scFv-GAA fusion protein (e.g., as set forth in SEQ ID NO:10 or SEQ ID NO:79) or an anti-ITGA7scFv-GAA fusion protein, the human or non-human subject lacks endogenous GAA activity, and the GAA activity is effectively restored in the subject.

In one aspect, the invention provides a method of treating a patient (human or non-human) with an enzyme deficiency by administering to the patient a gene therapy vector containing a nucleic acid sequence encoding a multidomain therapeutic protein comprising a delivery domain and an enzyme domain. In one embodiment, the enzyme domain comprises a glycosidase, such as GAA (e.g., SEQ ID NO:1) or a biologically active portion thereof (e.g., SEQ ID NO:78) or GLA (e.g., UniProtKB No. P06280, aa32-429, SEQ ID NO:13), and the patient has Pompe disease or Fabry disease. In one embodiment, the delivery domain of the multidomain therapeutic protein is an antigen-binding protein that binds to an internalization effector, such as CD63 or ITGA7. In one embodiment, the delivery domain is an scFv molecule that binds CD63. In one embodiment, the delivery domain is an scFv molecule that binds ITGA7. In another embodiment, the gene therapy vector comprises an AAV vector containing a nucleic acid sequence that encodes an anti-CD63-GAA fusion multidomain therapeutic protein (e.g., SEQ ID NO:10 or SEQ ID NO:79). In another embodiment, the gene therapy vector is an AAV vector comprising a nucleic acid sequence that encodes an anti-ITGA7-GAA fusion multidomain therapeutic protein. In another embodiment, the gene therapy vector comprises a naked polynucleotide comprising a nucleic acid sequence that encodes an anti-CD63-GAA fusion multidomain therapeutic protein (e.g., SEQ ID NO:10 or SEQ ID NO:79). In another embodiment, the gene therapy vector comprises a naked polynucleotide comprising a nucleic acid sequence that encodes an anti-ITGA7-GAA fusion multidomain therapeutic protein. In another embodiment, the gene therapy vector comprises a polynucleotide complex comprising a nucleic acid sequence that encodes an anti-CD63-GAA fusion multidomain therapeutic protein (e.g., SEQ ID NO:10 or SEQ ID NO:79). In another embodiment, the gene therapy vector comprises a polynucleotide complex comprising a nucleic acid sequence that encodes an anti-ITGA7-GAA fusion multidomain therapeutic protein.

In one aspect, the present invention relates to a composition according to the invention for use in medicine. In one embodiment the composition, e.g., a pharmaceutical composition, may comprise a gene therapy vector comprising a nucleic acid sequence encoding a multidomain therapeutic protein comprising a delivery domain and an enzyme domain. In one embodiment, the delivery domain of the multidomain therapeutic protein is an antigen-binding protein that binds to an internalization effector, such as CD63 or ITGA7. In one embodiment, the delivery domain is an scFv molecule that binds CD63. In one embodiment, the delivery domain is an scFv molecule that binds ITGA7. In another embodiment, the gene therapy vector is an AAV vector containing a polynucleotide that encodes an anti-CD63-GAA fusion multidomain therapeutic protein. In another embodiment, the gene therapy vector is an AAV vector containing a polynucleotide that encodes an anti-ITGA7-GAA fusion multidomain therapeutic protein. In some embodiments, the polynucleotide, e.g., a gene therapy vector, comprises a tissue specific regulatory element. In some embodiments, the tissue specific regulatory element comprises the sequence set forth as SEQ ID NO:8, SEQ ID NO:9, or both. In some embodiments, the polynucleotide, e.g., gene therapy vector comprises the nucleic acid sequence of SEQ ID NO:11.

In one aspect, described is a composition comprising a gene therapy vector containing a gene encoding a multidomain therapeutic protein comprising a delivery domain and an enzyme domain for use in treatment of a patient (human or non-human) with an enzyme deficiency, and/or for use in reducing glycogen accumulation in a tissue in a human or non-human subject. In one embodiment, the delivery domain of the multidomain therapeutic protein is an antigen-binding protein that binds to an internalization effector, such as CD63 or ITGA7. In one embodiment, the delivery domain is an scFv molecule that binds CD63. In one embodiment, the delivery domain is an scFv molecule that binds ITGA7. In another embodiment, the gene therapy vector is an AAV vectors containing a polynucleotide that encodes an anti-CD63-GAA fusion multidomain therapeutic protein. In another embodiment, the gene therapy vector is an AAV vectors containing a polynucleotide that encodes an anti-ITGA7-GAA fusion multidomain therapeutic protein. The clinical indications entailing an enzyme deficiency may be, but not limited to, e.g. Pompe's Disease or Fabry's disease. In some embodiments, the polynucleotide, e.g., a gene therapy vector, comprises a tissue specific regulatory element. In some embodiments, the tissue specific regulatory element comprises the sequence set forth as SEQ ID NO:8, SEQ ID NO:9, or both. In some embodiments, the polynucleotide, e.g., gene therapy vector comprises the nucleic acid sequence of SEQ ID NO:11.

In one aspect, described is use of a pharmaceutical composition according to the invention for the manufacture of a medicament for therapeutic application such as e.g. treatment of a patient (human or non-human) with an enzyme deficiency and/or reducing glycogen accumulation in a tissue in a human or non-human subject. The composition may comprise e.g. a gene therapy vector containing a gene encoding a multidomain therapeutic protein comprising a delivery domain and an enzyme domain. In one embodiment, the delivery domain of the multidomain therapeutic protein is an antigen-binding protein that binds to an internalization effector, such as CD63 or ITGA7. In one embodiment, the delivery domain is an scFv molecule that binds CD63. In one embodiment, the delivery domain is an scFv molecule that binds ITGA7. In another embodiment, the gene therapy vector is an AAV vectors containing a polynucleotide that encodes an anti-CD63-GAA fusion multidomain therapeutic protein. In another embodiment, the gene therapy vector is an AAV vectors containing a polynucleotide that encodes an anti-ITGA7-GAA fusion multidomain therapeutic protein. The clinical indications entailing an enzyme deficiency may be, but not limited to, e.g. Pompe's Disease or Fabry's disease.

In one embodiment, the multidomain therapeutic protein comprises a GAA enzyme domain, and high serum levels of GAA are maintained in the serum of the patient for at least 12 weeks after administering the gene therapy vector. In one embodiment, the multidomain therapeutic protein comprises a GAA enzyme domain, and glycogen levels in heart, skeletal muscle, and liver tissue in the patient are maintained at wildtype levels 3 months after administration of the gene therapy vector. In one embodiment, the multidomain therapeutic protein comprises a GAA enzyme domain, and the muscle strength of the patient after treatment is restored to wildtype levels.

In one aspect, the invention provides a method of reducing glycogen accumulation in a tissue in a human or non-human subject by administering a gene therapy vector containing a polynucleotide that encodes a multidomain therapeutic protein. In one embodiment, the tissue is liver, heart, or skeletal muscle. In one embodiment, the human or non-human subject has Pompe disease. In one embodiment, the multidomain therapeutic protein comprises an anti-CD63 scFv-GAA fusion protein. In another embodiment, the multidomain therapeutic protein comprises an anti-ITGA7 scFv-GAA fusion protein.

In one aspect, described herein is a method of reducing cross-reactive immunological material against an enzyme in a patient (human or non-human) with a deficiency in the enzyme, the method comprising administering to the patient a gene therapy vector containing a gene encoding the replacement enzyme only or a multidomain therapeutic protein comprises a delivery domain and an enzyme domain. In some embodiments, the gene therapy vector is an AAV vector, which may be a chimeric AAV vector (e.g., an AAV2/8). In some embodiments, the enzyme domain comprises a glycosidase, such as GAA (e.g., SEQ ID NO:1) or GLA (e.g., UniProtKB No. P06280, aa32-429, SEQ ID NO:13), and the patient has Pompe disease or Fabry disease, and the delivery domain is an antigen-binding protein that binds to an internalization effector. In some embodiments, the gene therapy vector is administered in sufficient amounts to increase serum levels of GAA such that cross-reactive immunological material is reduced or no cross-reactive immunological material is generated in detectable amounts. In some embodiments, the gene therapy vector is administered in sufficient amounts to increase serum levels of GAA over a period of time. In some embodiments, the patient is infected with a virus (e.g., an AAV) comprising the gene therapy vector, optionally wherein the virus is pseudotyped to specifically target a tissue or cell selected from the group consisting of the GALT, liver, hematopoietic stem cell, red blood cell or a combination thereof and/or wherein the gene therapy vector comprises a cell or tissue specific enhancer and/or promoter, e.g., a liver specific enhancer (e.g., serpina 1) and/or a liver specific promoter (e.g., TTR). In one embodiment, the internalization effector is a cell-surface molecule that is endocytosed and trafficked to the lysosome. In a specific embodiment, the internalization effector is a CD63 molecule. In a specific embodiment, the delivery domain is an antibody, an antibody fragment, or a single-chain variable fragment (scFv), such as an scFv that binds CD63 (e.g., SEQ ID NO:2). In some embodiments, the method comprises administering to the patient a gene therapy vector as described herein in combination with at least one immunosuppressive agent, wherein the gene therapy vector and immunosuppressive agent are administered simultaneously and/or sequentially. In some embodiments, the patient maintains a constant level of the immunosuppressive agent.

In one aspect, described herein is a method of inducing tolerance to an enzyme in a patient (human or non-human) with a deficiency in the enzyme (i.e., tolerizing the patient to the enzyme, the method comprising reducing cross-reactive immunological material in the patient, e.g., administering to the patient a gene therapy vector containing a gene encoding the replacement enzyme only or a multidomain therapeutic protein comprising a delivery domain and an enzyme domain. In some embodiments, disclosed is a method of inducing tolerance to an enzyme in a patient with a deficiency in the enzyme, the method comprising administering to the patient a gene therapy vector containing a gene encoding the replacement enzyme only, or a multidomain therapeutic protein comprising a delivery domain and an enzyme domain, over a period of time such that no increase in detectable cross-reactive immunological material in the patient is generated. In some embodiments, the multidomain therapeutic protein comprises a delivery domain and an enzyme domain. In some embodiments, the gene therapy vector is an AAV vector, which may be a chimeric AAV vector (e.g., an AAV2/8) and/or an engineered AAV vector (e.g., a tropism modified recombinant viral vector useful for targeting, e.g., a receptor or marker preferentially or exclusively expressed by a cell or tissue, e.g., hepatocyte or liver, mucosal tissue, red blood cells, hematopoietic stem cells, etc.), and optionally wherein the gene is expressed under the control of an enhancer and/or promoter specific for the cell or tissue, e.g., a liver specific promoter, etc. In some embodiments, the enzyme domain comprises a glycosidase, such as GAA (e.g., SEQ ID NO:1) or GLA (e.g., UniProtKB No. P06280, aa32-429, SEQ ID NO:13), and the patient has Pompe disease or Fabry disease, and the delivery domain is an antigen-binding protein that binds to an internalization effector. In one embodiment, the internalization effector is a cell-surface molecule that is endocytosed and trafficked to the lysosome. In a specific embodiment, the internalization effector is a CD63 molecule. In a specific embodiment, the delivery domain is an antibody, an antibody fragment, or a single-chain variable fragment (scFv), such as an scFv that binds CD63 (e.g., SEQ ID NO:2). In some embodiments, a method of treating a patient with an enzyme deficiency comprises administering to the patient a recombinant form and/or isozyme of the enzyme (e.g., GAA in a patient with Pompe, e.g., an scFv63::GAA, GAA, optimized GAA, or combination thereof), wherein the patient is tolerant to the enzyme, e.g., wherein the patient has been tolerized to the enzyme according to a method disclosed herein. Accordingly, in some embodiments, a method of administering an enzyme to a patient deficient thereof comprises tolerizing the patient to the enzyme, e.g., by administering a gene therapy vector encoding the enzyme or multidomain therapeutic protein comprising the enzyme, preferably in sufficient amounts to increase serum levels of the enzyme such that cross-reactive immunological material is at a level comparable to that found in a patient not deficient of the enzyme, optionally wherein the gene therapy vector is specifically targeted to the liver and/or comprises a liver specific enhancer and/or promoter. In some embodiments, the method further comprises, after administration of the gene targeting vector, further administering the enzyme and/or a recombinant variant thereof, including a multidomain therapeutic protein comprising the enzyme.

In another aspect, the present invention provides antibodies and antigen-binding fragments thereof that bind to human CD63. The antibodies according to this aspect of the invention are useful, inter alia, for specifically directing the internalization and/or lysosomal trafficking of an enzyme, e.g., GAA or GLA. As such, this aspect of the invention also provides bispecific antibodies, antigen-binding fragments thereof that bind human CD63, and antibody-protein fusion constructs (see, e.g., FIG. 1A).

Exemplary anti-CD63 antibodies of the present invention are listed in Table 11. Table 11 sets forth the amino acid and nucleic acid sequence identifiers of the heavy chain variable regions (HCVRs) and light chain variable regions (LCVRs), as well as heavy chain complementarity determining regions (HCDR1, HCDR2 and HCDR3), and light chain complementarity determining regions (LCDR1, LCDR2 and LCDR3) of the exemplary anti-CD63 antibodies.

The present invention provides antibodies, or antigen-binding fragments thereof, comprising an HCVR comprising an amino acid sequence selected from any of the HCVR amino acid sequences listed in Table 11, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 11, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 11 paired with any of the LCVR amino acid sequences listed in Table 11. According to certain embodiments, the present invention provides antibodies, or antigen-binding fragments thereof, comprising an HCVR/LCVR amino acid sequence pair contained within any of the exemplary anti-CD63 antibodies listed in Table 11. In certain embodiments, the HCVR/LCVR amino acid sequence pair is selected from the group consisting of SEQ ID NOs: 14/22, SEQ ID NOs: 30/38, SEQ ID NOs: 46/54, and SEQ ID NOs: 62/70.

The present invention also provides antibodies, or antigen-binding fragments thereof, comprising a heavy chain CDR1 (HCDR1) comprising an amino acid sequence selected from any of the HCDR1 amino acid sequences listed in Table 11 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 11 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 11 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 11 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 11 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 11 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 11 paired with any of the LCDR3 amino acid sequences listed in Table 11. According to certain embodiments, the present invention provides antibodies, or antigen-binding fragments thereof, comprising an HCDR3/LCDR3 amino acid sequence pair contained within any of the exemplary anti-CD63 antibodies listed in Table 11. In certain embodiments, the HCDR3/LCDR3 amino acid sequence pair is selected from the group consisting of SEQ ID NOs: SEQ ID NOs: 20/28, SEQ ID NOs: 36/44, SEQ ID NOs: 52/60, and SEQ ID NOs: 68/76.

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-CD63 antibodies listed in Table 11. In certain embodiments, the HCDR1-HCDR2-HCDR3-LCDR1-LCDR2-LCDR3 amino acid sequences set is selected from the group consisting of SEQ ID NOs:16-18-20-24-26-28, SEQ ID NOs: 32-34-36-40-42-44, SEQ ID NOs:48-50-52-56-58-60, and SEQ ID NOs: 64-66-68-72-74-76.

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-CD63 antibodies listed in Table 11. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs:14/22, SEQ ID NOs: 30/38, SEQ ID NOs: 46/54, and SEQ ID NOs: 62/70. Methods and techniques for identifying CDRs within HCVR and LCVR amino acid sequences are well known in the art and can be used to identify CDRs within the specified HCVR and/or LCVR amino acid sequences disclosed herein.

Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-CD63 antibodies or portions thereof. For example, the present invention provides nucleic acid molecules encoding any of the HCVR amino acid sequences listed in Table 11; in certain embodiments the nucleic acid molecule comprises a polynucleotide sequence selected from any of the HCVR nucleic acid sequences listed in Table 11, or a substantially similar sequence thereof having at least 90%, at least 95%, at least 98% or at least 99% sequence identity thereto.

The present invention also provides nucleic acid molecules encoding any of the LCVR amino acid sequences listed in Table 11; in certain embodiments the nucleic acid molecule comprises a polynucleotide sequence selected from any of the LCVR nucleic acid sequences listed in Table 11, or a substantially similar sequence thereof having at least 90%, at least 95%, at least 98% or at least 99% sequence identity thereto.

The present invention also provides nucleic acid molecules encoding any of the HCDR1 amino acid sequences listed in Table 11; in certain embodiments the nucleic acid molecule comprises a polynucleotide sequence selected from any of the HCDR1 nucleic acid sequences listed in Table 11, or a substantially similar sequence thereof having at least 90%, at least 95%, at least 98% or at least 99% sequence identity thereto.

The present invention also provides nucleic acid molecules encoding any of the HCDR2 amino acid sequences listed in Table 11; in certain embodiments the nucleic acid molecule comprises a polynucleotide sequence selected from any of the HCDR2 nucleic acid sequences listed in Table 11, or a substantially similar sequence thereof having at least 90%, at least 95%, at least 98% or at least 99% sequence identity thereto.

The present invention also provides nucleic acid molecules encoding any of the HCDR3 amino acid sequences listed in Table 11; in certain embodiments the nucleic acid molecule comprises a polynucleotide sequence selected from any of the HCDR3 nucleic acid sequences listed in Table 11, or a substantially similar sequence thereof having at least 90%, at least 95%, at least 98% or at least 99% sequence identity thereto.

The present invention also provides nucleic acid molecules encoding any of the LCDR1 amino acid sequences listed in Table 11; in certain embodiments the nucleic acid molecule comprises a polynucleotide sequence selected from any of the LCDR1 nucleic acid sequences listed in Table 11, or a substantially similar sequence thereof having at least 90%, at least 95%, at least 98% or at least 99% sequence identity thereto.

The present invention also provides nucleic acid molecules encoding any of the LCDR2 amino acid sequences listed in Table 11; in certain embodiments the nucleic acid molecule comprises a polynucleotide sequence selected from any of the LCDR2 nucleic acid sequences listed in Table 11, or a substantially similar sequence thereof having at least 90%, at least 95%, at least 98% or at least 99% sequence identity thereto.

The present invention also provides nucleic acid molecules encoding any of the LCDR3 amino acid sequences listed in Table 11; in certain embodiments the nucleic acid molecule comprises a polynucleotide sequence selected from any of the LCDR3 nucleic acid sequences listed in Table 11, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-CD63 antibodies listed in Table 11.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-CD63 antibodies listed in Table 11.

The present invention also provides nucleic acid molecules encoding both an HCVR and an LCVR, wherein the HCVR comprises an amino acid sequence of any of the HCVR amino acid sequences listed in Table 11, and wherein the LCVR comprises an amino acid sequence of any of the LCVR amino acid sequences listed in Table 11. In certain embodiments, the nucleic acid molecule comprises a polynucleotide sequence selected from any of the HCVR nucleic acid sequences listed in Table 11, or a substantially similar sequence thereof having at least 90%, at least 95%, at least 98% or at least 99% sequence identity thereto, and a polynucleotide sequence selected from any of the LCVR nucleic acid sequences listed in Table 11, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-CD63 antibody listed in Table 11.

The present invention also provides recombinant expression vectors capable of expressing a polypeptide comprising a heavy or light chain variable region of an anti-CD63 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 11. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In some aspects, the present invention includes antibodies or antigen-binding fragments thereof, such as anti-CD63 antibodies, having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shields et al. (2002) JBC 277:26733), where cytotoxicity is desireable. In other applications, modification of galactosylation can be made in order to modify complement dependent cytotoxicity (CDC).

In another aspect, the invention provides a pharmaceutical composition comprising a recombinant human antibody or fragment thereof which specifically binds CD63 and a pharmaceutically acceptable carrier. In a related aspect, the invention features a composition which is a combination of an anti-CD63 antibody and a second therapeutic agent. In one embodiment, the second therapeutic agent is any agent that is advantageously combined with an anti-CD63 antibody. Additional combination therapies and co-formulations involving the anti-CD63 antibodies of the present invention are disclosed elsewhere herein.

DRAWINGS

FIG. 1A schematically represents multidomain therapeutic proteins. Panel A depicts a multidomain therapeutic protein comprising a bispecific antibody (ii) and a replacement enzyme (i). Panel B depicts an enzyme-Fc fusion polypeptide (i) associating with an internalization effector-specific half-body (ii) to form the multidomain therapeutic protein. Panel C depicts a replacement enzyme (hexagon) covalently linked to the C-terminus of the heavy chain of an anti-internalization effector antibody. Panel D depicts a replacement enzyme (hexagon) covalently linked to the N-terminus of the heavy chain of an anti-internalization effector antibody. Panel E depicts a replacement enzyme (hexagon) covalently linked to the C-terminus of the light chain of an anti-internalization effector antibody. Panel F depicts a replacement enzyme (hexagon) covalently linked to the N-terminus of the light chain of an anti-internalization effector antibody. Panel G depicts a replacement enzyme (hexagon) covalently linked to the C-terminus of a single-chain variable fragment (scFv) containing a VH region (shaded bar) and a VL region (open bar). Panel H depicts a replacement enzyme (hexagon) covalently linked to two scFv domains, the first scFv (i) which serves as a first delivery domain, and the second scFv (ii) which serves as a second delivery domain.

Figure 1B:
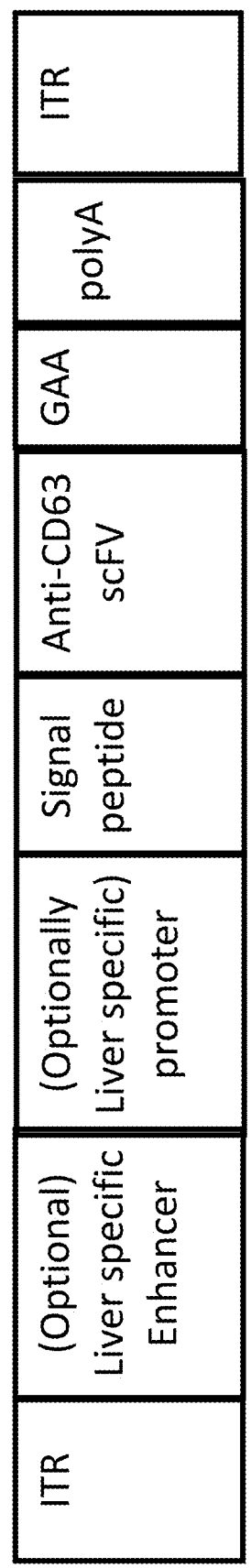

FIG. 1B is a non-limiting exemplary illustration of an AAV gene therapy vector that encodes a multidomain therapeutic protein represented in panel, wherein the scFv is an anti-human CD63 scFv and the replacement enzyme is GAA (e.g., anti-hCD63scFv::hGAA; see, e.g., the amino acid sequence set forth as SEQ ID NO:10). Amino acids 1-119 of SEQ ID NO:10 provide the amino acid sequence of the heavy chain variable domain ($V_H$) of the H5C6 antibody; amino acids 120-134 of SEQ ID NO:10 provide an amino acid linker sequence between the heavy and light chain variable domains of H5C6; amino acids 135-245 of SEQ ID NO:10 provide the amino acid sequence of the light chain variable domain ($V_L$) of the H5C6 antibody; amino acids 136-250 of SEQ ID NO:10 provides an amino acid linker sequence between the anti-hCD63scFv and GAA; and amino acids 251-1133 of SEQ ID NO:10 provides the amino acid sequence of GAA. Exemplary 5'ITR and 3' ITR sequences are respectively set forth as SEQ ID NO:6 and SEQ ID NO:7. An exemplary liver specific enhancer (serpina 1) is set forth as SEQ ID NO:9. An exemplary liver specific promoter (TTR) is set forth as SEQ ID NO:8. Additional exemplary anti-CD63 $V_H$ and $V_L$ amino acid sequences (and nucleotide sequences encoding same) that may be used to construct a multidomain therapeutic protein comprising an anti-CD63 antibody or antigen binding portion thereof are provided in Table 11.

Figure 2:
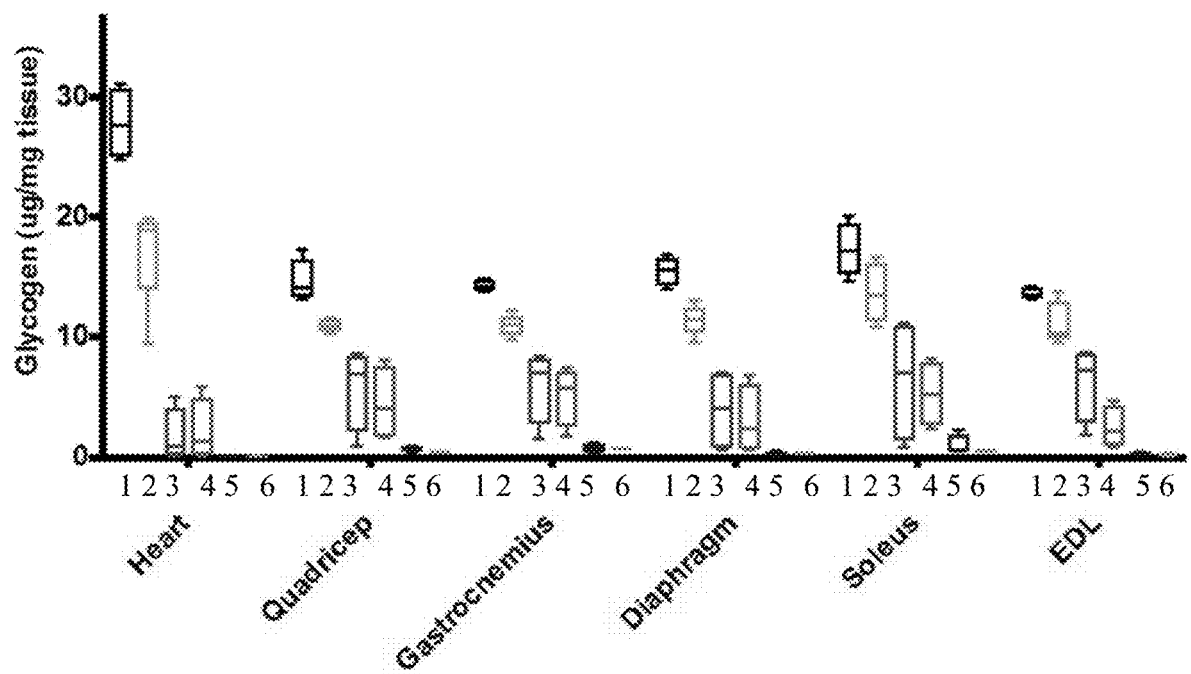

FIG. 2 is a bar graph depicting the amount of stored glycogen in micrograms per milligram of tissue as a function of delivered enzyme. The X-axis depicts tissues from a $CD63^{hu/hu}$; $GAA^{-/-}$ mouse from left to right: heart, quadriceps, gastrocnemius, diaphragm, soleus, and extensor digitorum longus (EDL) muscle. Black boxes ("1") depict the amount of stored glycogen in an untreated mouse Pompe disease model. Orange boxes ("2") depict the amount of stored glycogen in an untreated wildtype mouse model. Lime green boxes ("3") depict the amount of stored glycogen in a mouse Pompe disease model treated with AAV-hGAA (adeno-associated virus vector containing gene encoding human GAA) at a dose of $10^{10}$ vg. Forest green boxes ("4") depict the amount of stored glycogen in a mouse Pompe disease model treated with AAV-hGAA at a dose of $10^{11}$ vg. Light blue boxes ("5") depict the amount of stored glycogen in a mouse Pompe disease model treated with AAV-anti-hCD63scFv::hGAA (adeno-associated virus vector containing gene encoding an anti-human CD63 scFv domain linked to human GAA) at a dose of $10^{10}$ vg. Dark blue boxes ("6") depict the amount of stored glycogen in a mouse Pompe disease model treated with AAV-anti-hCD63scFv::hGAA at a dose of $10^{11}$ vg.

Figure 3:
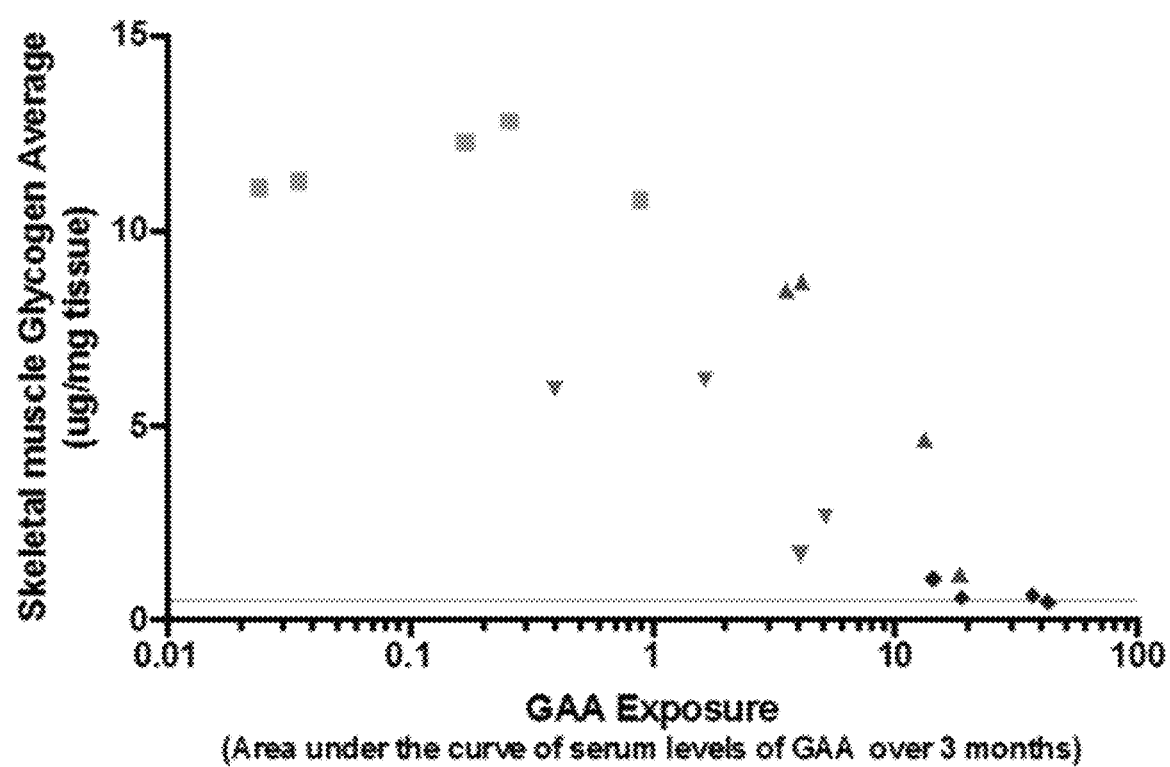

FIG. 3 is a bar graph depicting the average glycogen measured (µg/mg) in skeletal muscle tissue in each mouse at 3 months post-AAV injection. Each measurement is plotted as a function of GAA exposure (i.e., serum levels) per mouse treated with a particular enzyme construct at a particular dosage. Filled squares represent AAV-hGAA at a dose of $10^{10}$ vg. Filled pyramids represent AAV-hGAA at a dose of $10^{11}$ vg. Filled inverse pyramids represent AAV-anti-hCD63scFv::hGAA at a dose of $10^{10}$ vg. Filled diamonds represent AAV-anti-hCD63scFv::hGAA at a dose of $10^{11}$ vg.

Figure 4:
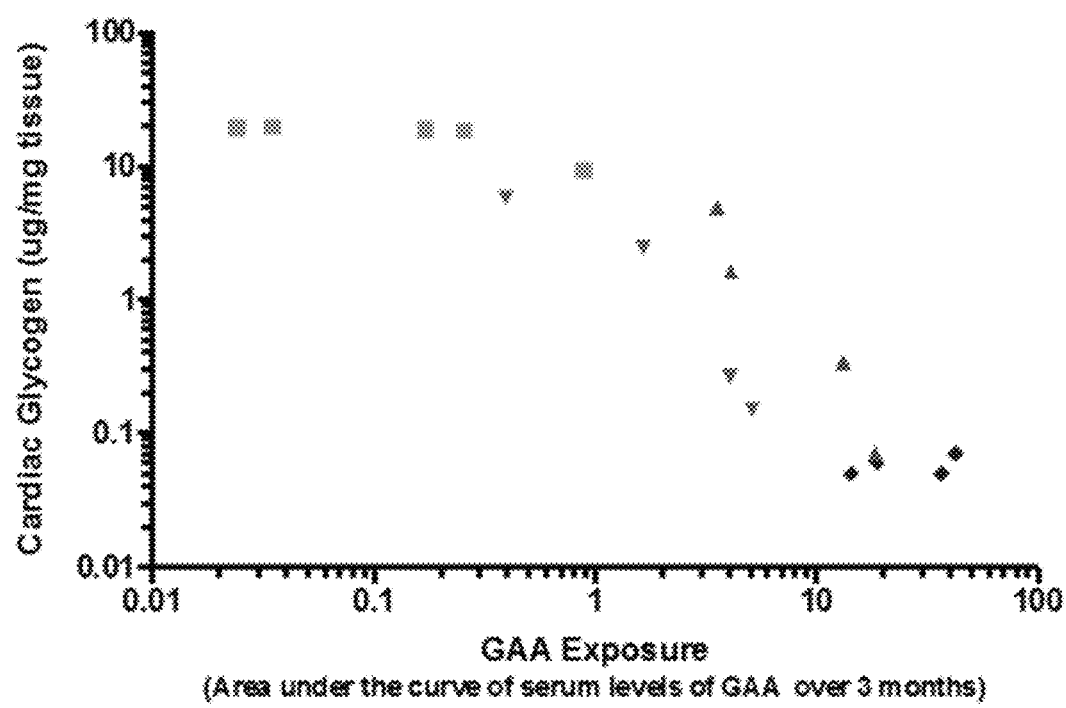

FIG. 4 is a dot plot depicting the average cardiac muscle glycogen measured (µg/mg) in heart tissue at 3 months post-AAV injection as a function of GAA exposure (i.e., serum levels), per mouse treated with a particular enzyme construct at a particular dosage. Filled squares represent AAV-hGAA at a dose of $10^{10}$ vg. Filled pyramids represent AAV-hGAA at a dose of $10^{11}$ vg. Filled inverse pyramids represent AAV-anti-hCD63scFv::hGAA at a dose of $10^{10}$ vg. Filled diamonds represent AAV-anti-hCD63scFv::hGAA at a dose of $10^{11}$ vg.

Figure 5:
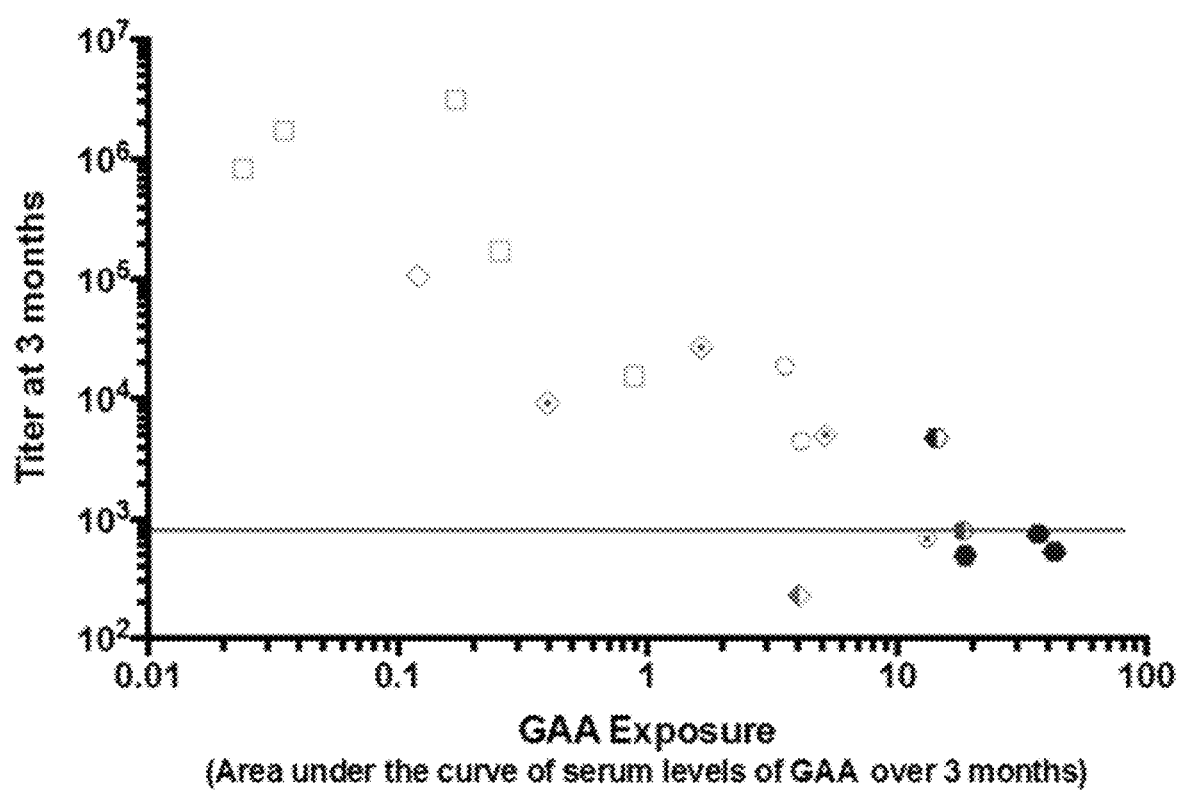

FIG. 5 is a dot plot depicting anti-GAA antibody titers at 3 months post-AAV injection as a function of GAA exposure (i.e. serum levels), per mouse treated with a particular enzyme construct at a particular dosage. Open squares represent AAV-hGAA at a dose of $10^{10}$ vg. Open circles represent AAV-hGAA at a dose of $10^{11}$ vg. Open diamonds represent AAV-anti-hCD63scFv::hGAA at a dose of $10^{10}$ vg. Hexagons represent AAV-anti-hCD63scFv::hGAA at a dose of $10^{11}$ vg.

Figure 6:
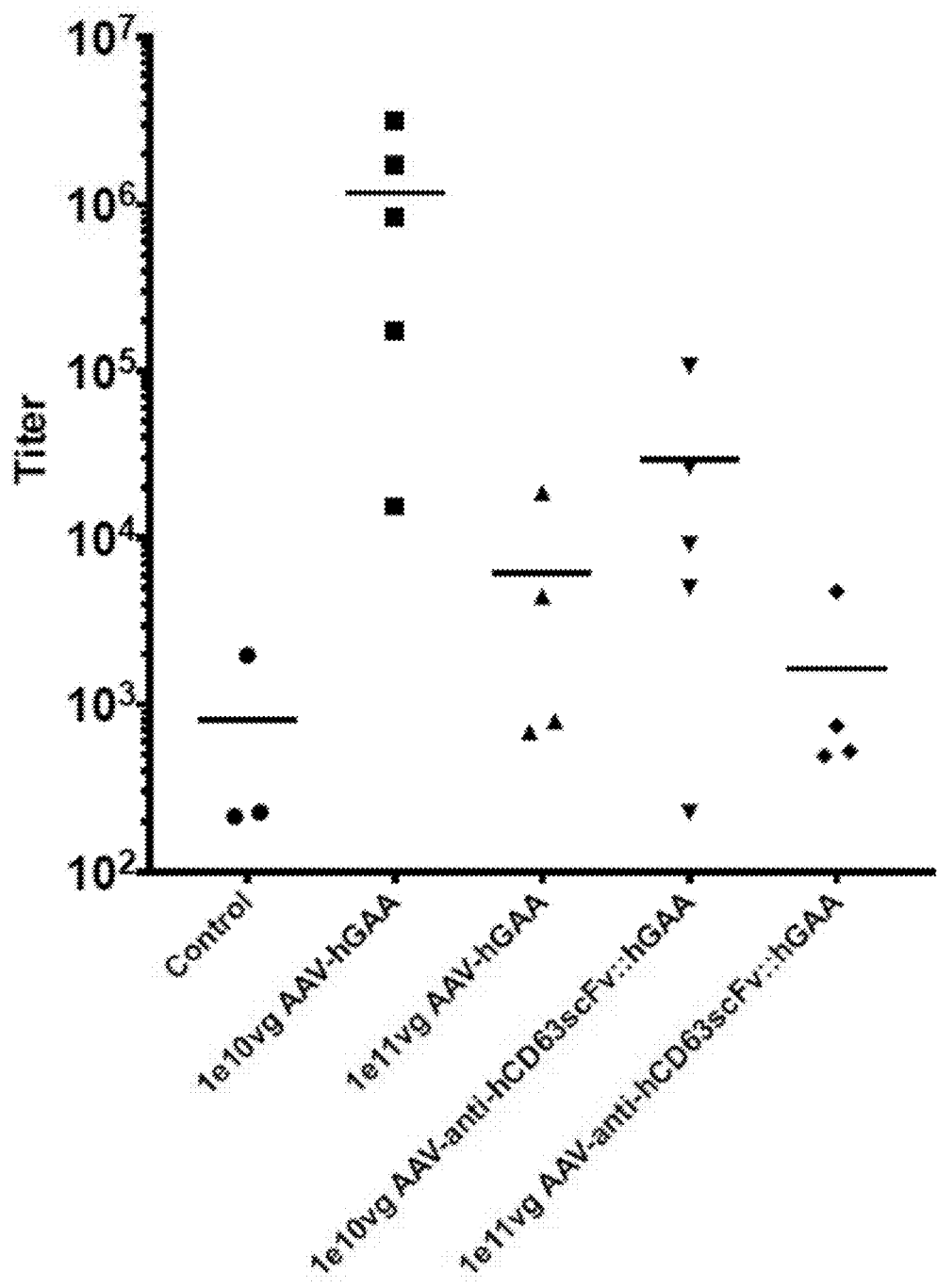

FIG. 6 is a dot plot depicting anti-GAA antibody titers at 3 months post-AAV injection as a function of enzyme construct and dose. Circles represent control mice receiving empty AAV vector. Squares represent AAV-hGAA at a dose of $10^{10}$ vg. Pyramids represent AAV-hGAA at a dose of $10^{11}$ vg. Inverse pyramids represent AAV-anti-hCD63scFv::hGAA at a dose of $10^{10}$ vg. Diamonds represent AAV-anti-hCD63scFv::hGAA at a dose of $10^{11}$ vg.

Figure 7A:
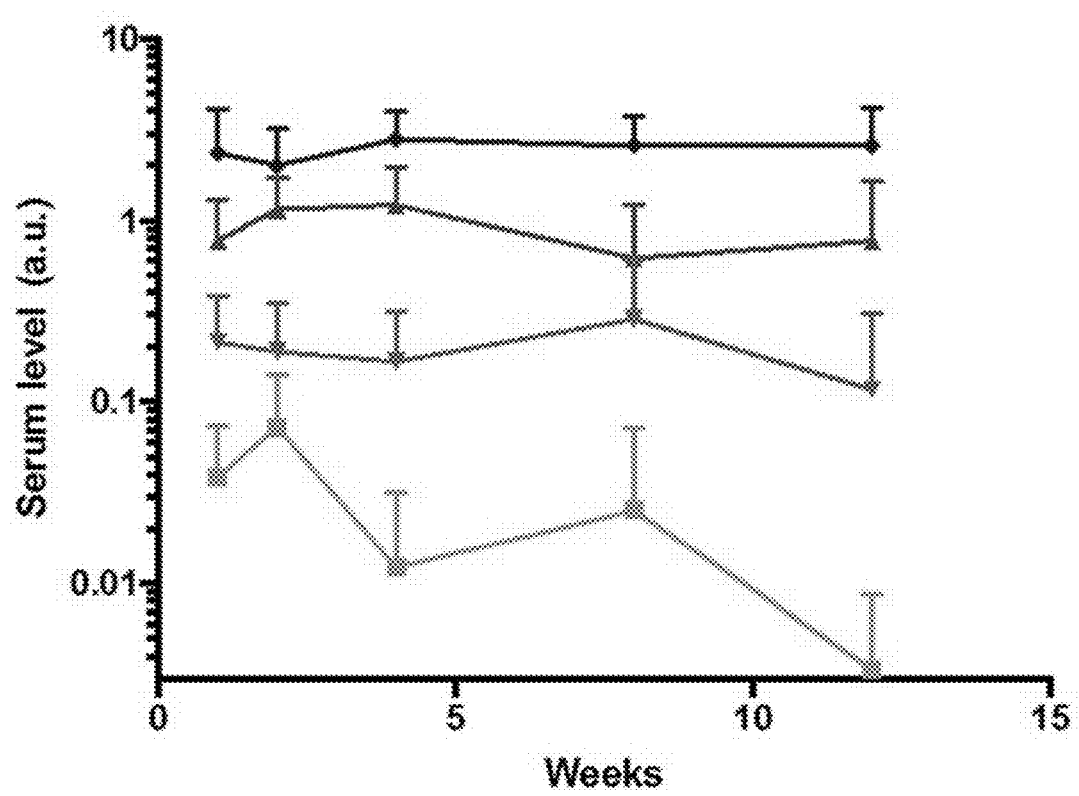

FIG. 7A is a line graph depicting serum levels of GAA (arbitrary units "a.u."; y-axis) as a function of time in weeks after gene therapy vector injection. Squares represent AAV-hGAA at a dose of $10^{10}$ vg. Pyramids represent AAV-hGAA at a dose of $10^{11}$ vg. Inverse pyramids represent AAV-antihCD63scFv::hGAA at a dose of $10^{10}$ vg. Diamonds represent AAV-anti-hCD63scFv::hGAA at a dose of $10^{11}$ vg.

Figure 7B:
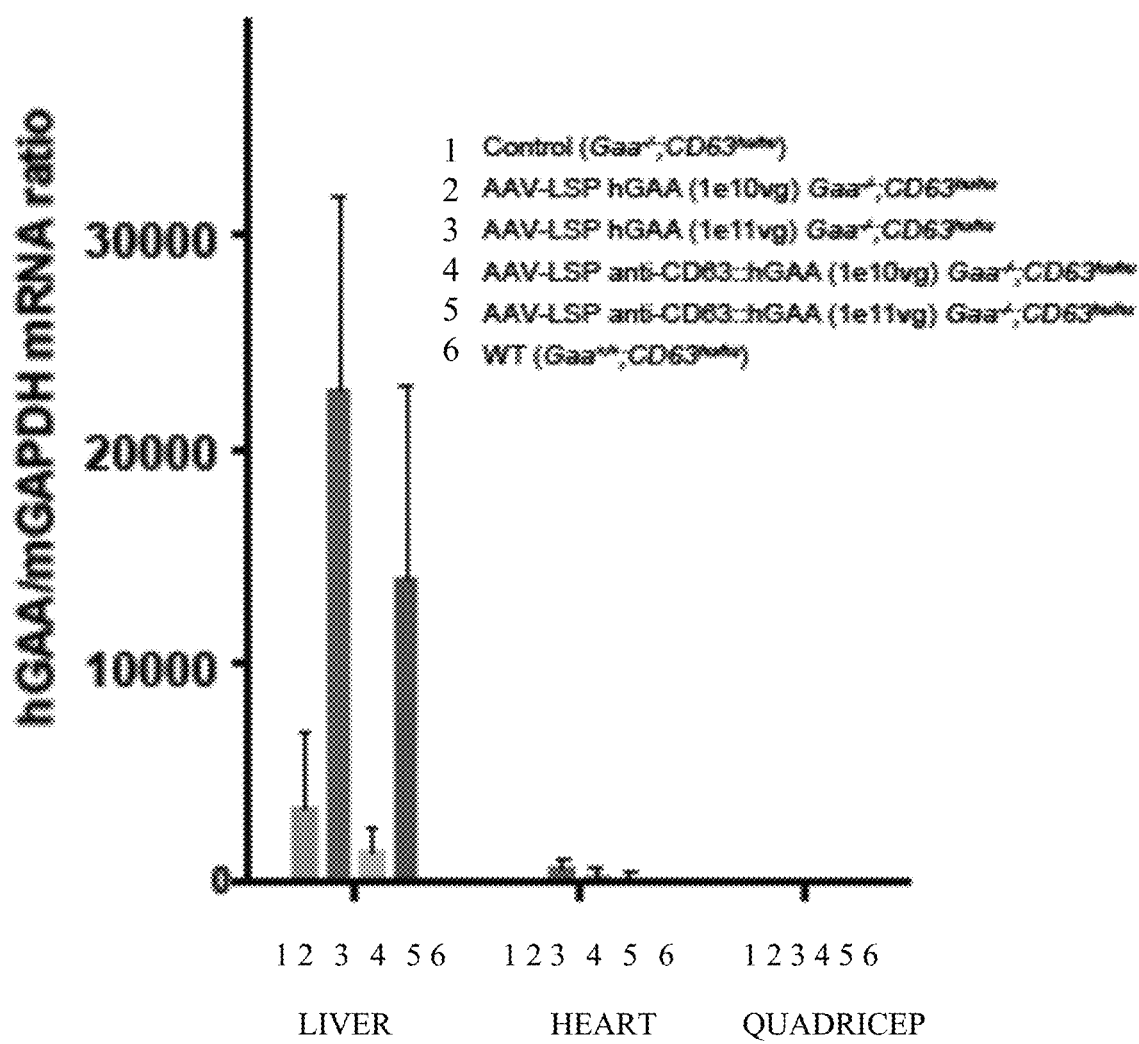

FIG. 7B is a bar graph depicting mRNA ratios (hGAA mRNA relative to mGADPH mRNA) following administration of AAV constructs in CD63 HumIn GAA KO mice (GAA−/−, CD63hu/hu mice) or GAA+/+, CD63hu/hu mice, as such: (1) untreated control, (2) AAV-liver-specific promoter-hGAA (1e10 vg), (3) AAV-liver-specific promoter-hGAA (1e11 vg), (4) AAV-liver-specific promoter-anti-hCD63::hGAA (1e10 vg), (5) AAV-liver-specific promoter-anti-hCD63::hGAA (1e11 vg), or (6) untreated control (GAA+/+, CD63hu/hu). Liver expression of GAA was detected for all injections of AAV construct.

Figure 7C:
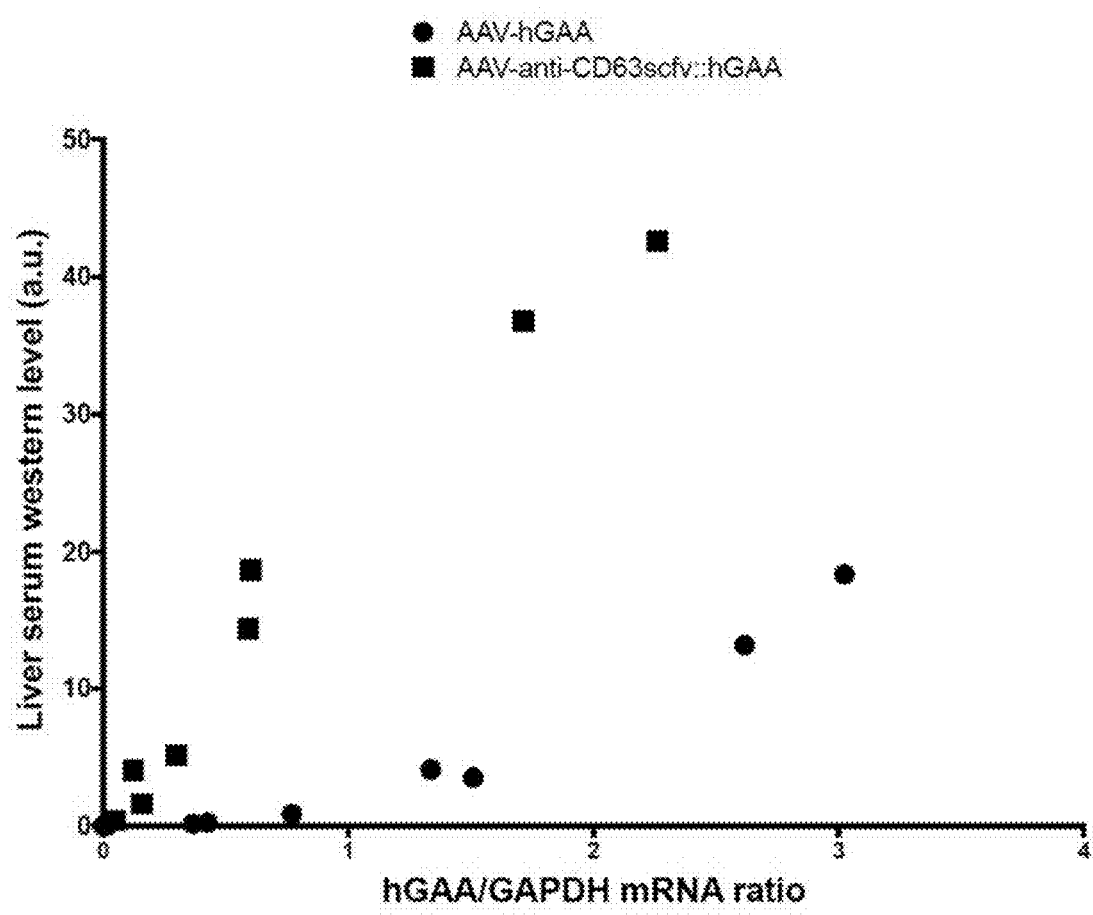

FIG. 7C is a plot graph comparing serum GAA level to RNA expression level of GAA for mice receiving the AAV encoding the fusion protein (squares) and mice receiving the AAV encoding GAA (both constructs provided a liver-specific promoter (LSP) to drive expression).

Figure 7D:
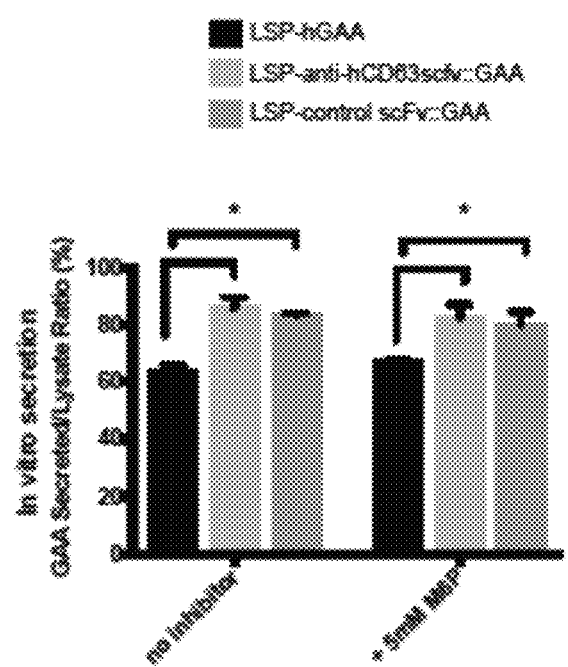

FIG. 7D is a bar graph showing Huh-7 human hepatocytes transiently transfected with liver-specific promoter driven constructs encoding for hGAA, anti-hCD63 scFv::GAA (fusion construct), or a non-binding fusion construct scFv::GAA control. Both scFv::GAA fusion constructs had a higher ratio of protein in the secreted supernatant than hGAA alone 3 days after transfection. Addition of M6P into the supernatant during the experimental period to mitigate CI-MPR-mediated uptake did not affect the ratio. (*=p<0.05, n=3).

Figure 8:
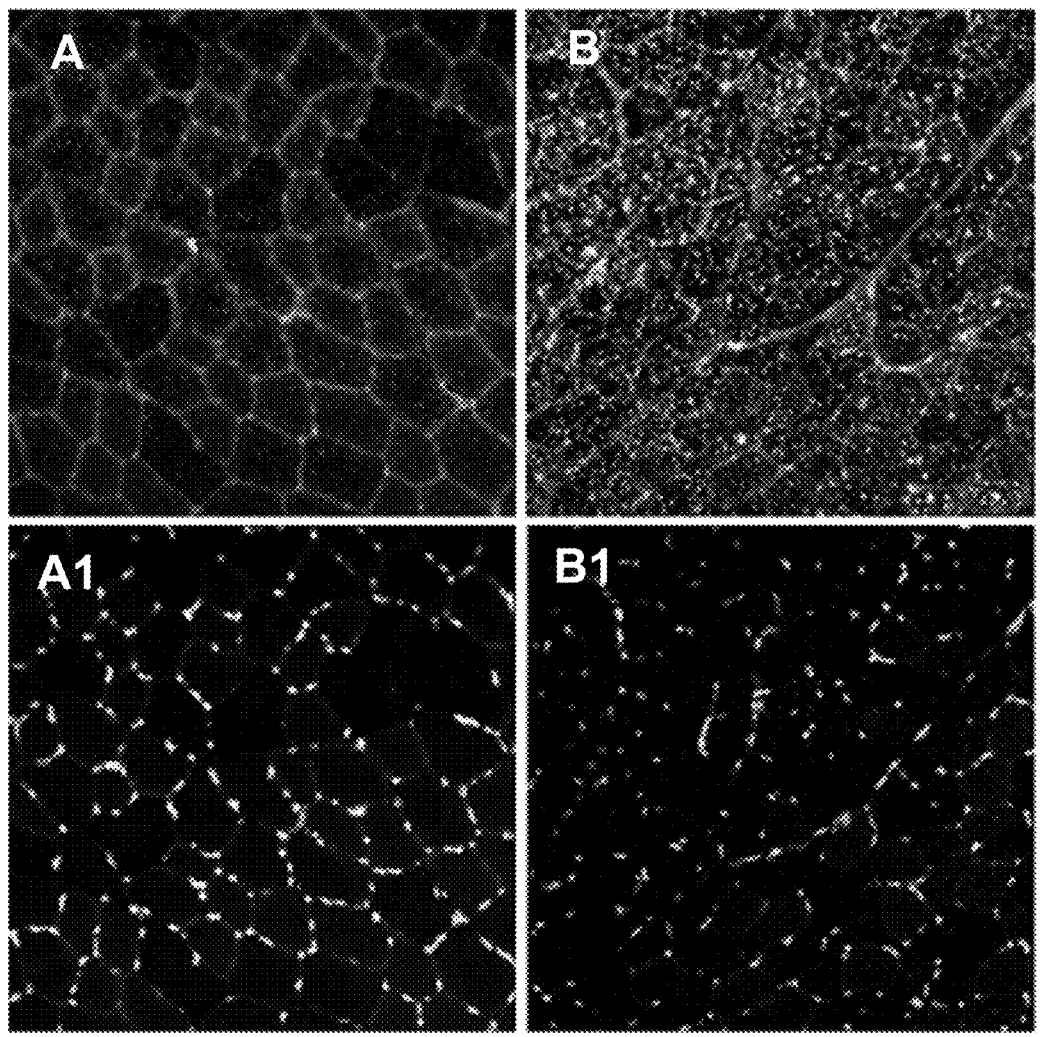
Figure 8:
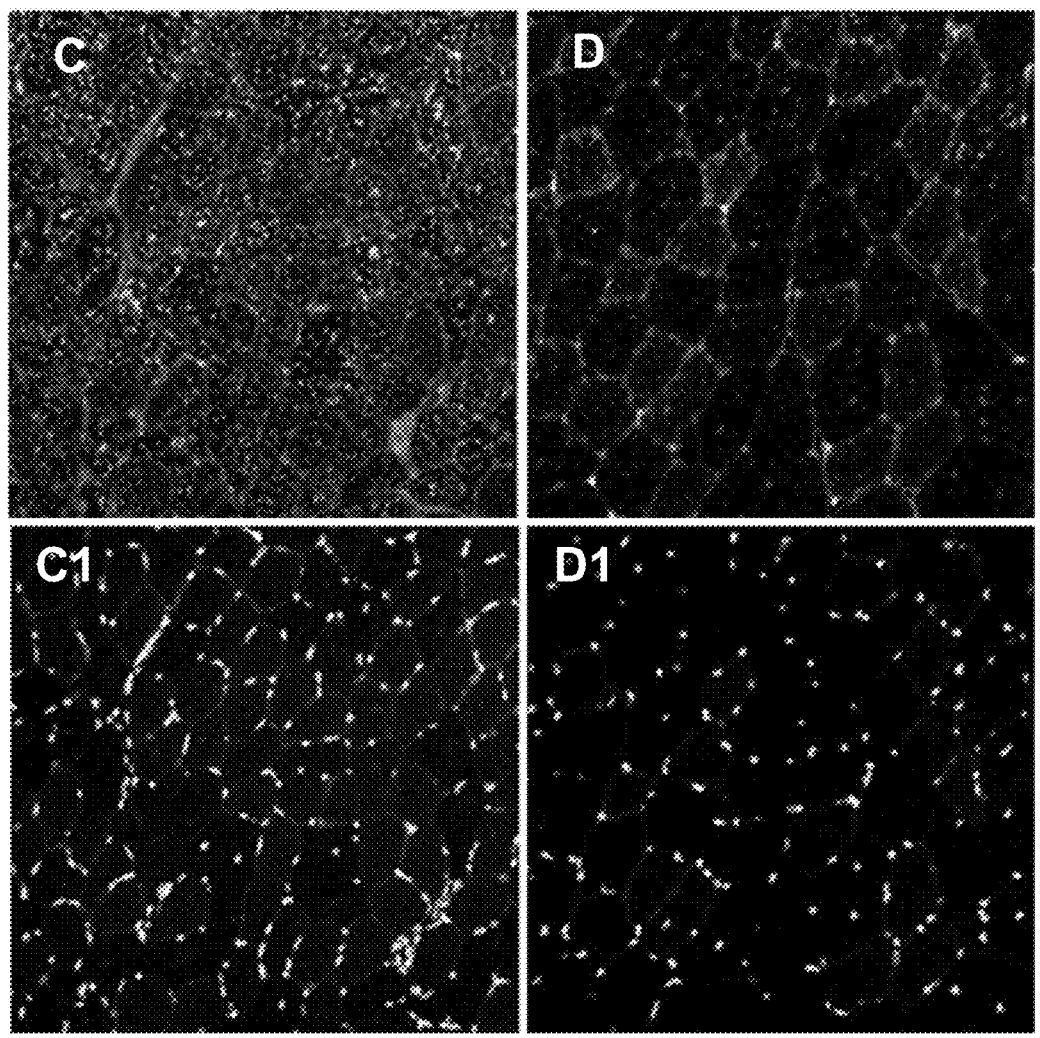

FIG. 8 are fluorescent micrographs depicting the lamp1-stained lysosomes in mouse muscle fibers counter-stained with DAPI to reveal nuclei. Panels A and A1 depict quadriceps cells derived from an untreated wildtype (GAA$^{+/+}$) mouse and stained for lamp1 (panel A), and nuclei (panel A1). Panels B and B1 depict quadriceps cells derived from an untreated GAA null (GAA$^{-/-}$) mouse and stained for lamp1 (panel B), and nuclei (panel B1). Panels C and C1 depict quadriceps cells derived from a GAA$^{-/-}$ mouse treated with an AAV-hGAA construct and stained for lamp1 (panel C), and nuclei (panel C1). Panels D and D1 depict quadriceps cells derived from a GAA$^{-/-}$ mouse treated with an AAV-hCD63scFv::hGAA construct and stained for lamp1 (panel D), and nuclei (panel D1).

Figure 9:
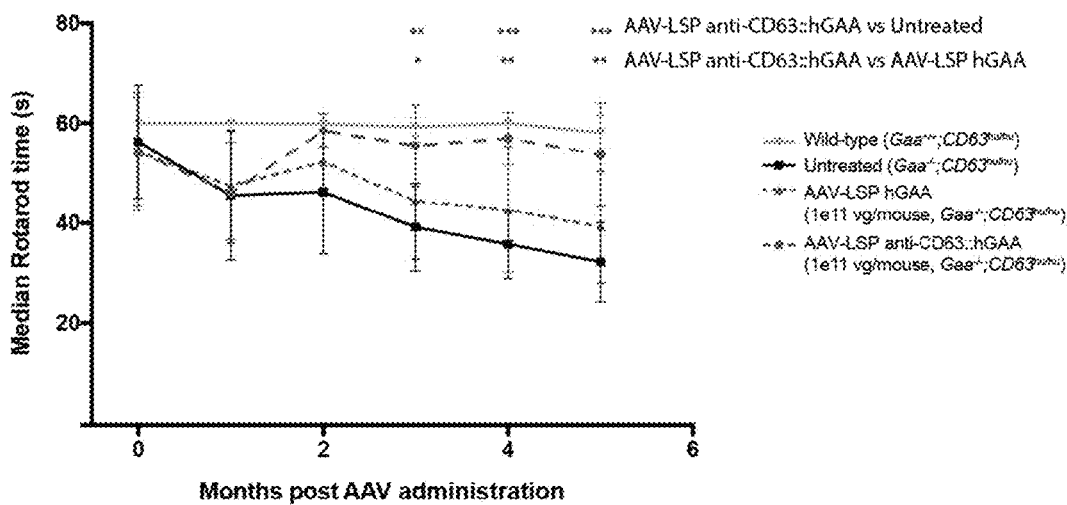
Figure 9:
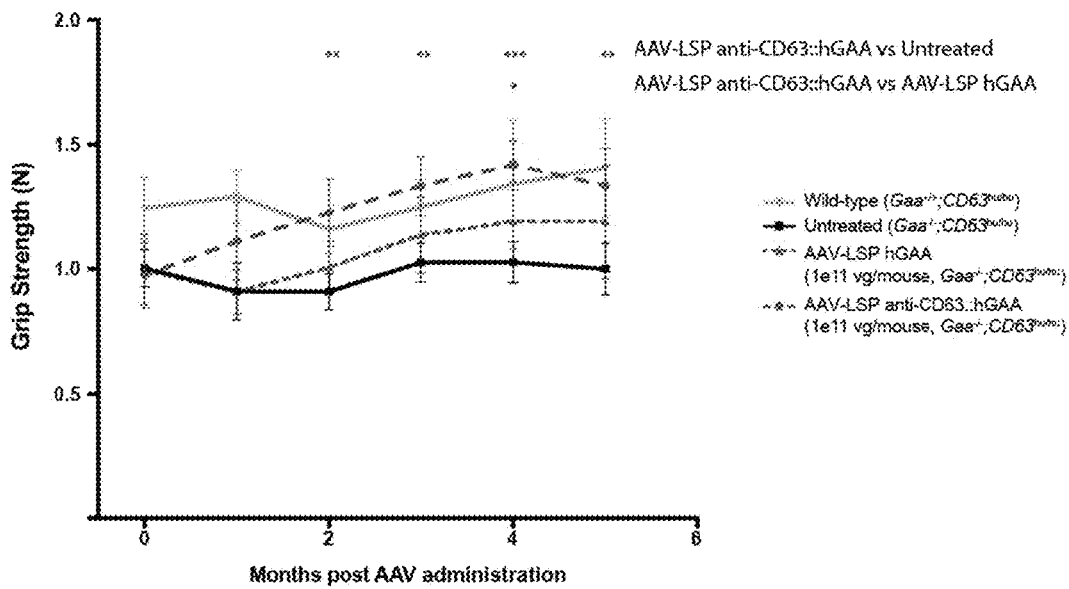

FIG. 9 depicts line graphs showing grip strength and Rotarod test performance of mice treated with either AAV-LSP hGAA or AAV-LSP anti-hCD63::hGAA. Accelerating Rotarod measurements (A) and forelimb grip strength measurements (B) of wild-type GAA mice (inverted triangle), untreated control (square), AAV-LSP-hGAA treatment (1e11 vg/mouse) (triangle) or AAV-LSP-anti-hCD63::hGAA treatment (1e11 vg/mouse) (circle) were taken at monthly intervals for 6 months. Error bars are +/−SD. N=8-10 for all groups.

Figure 10A:
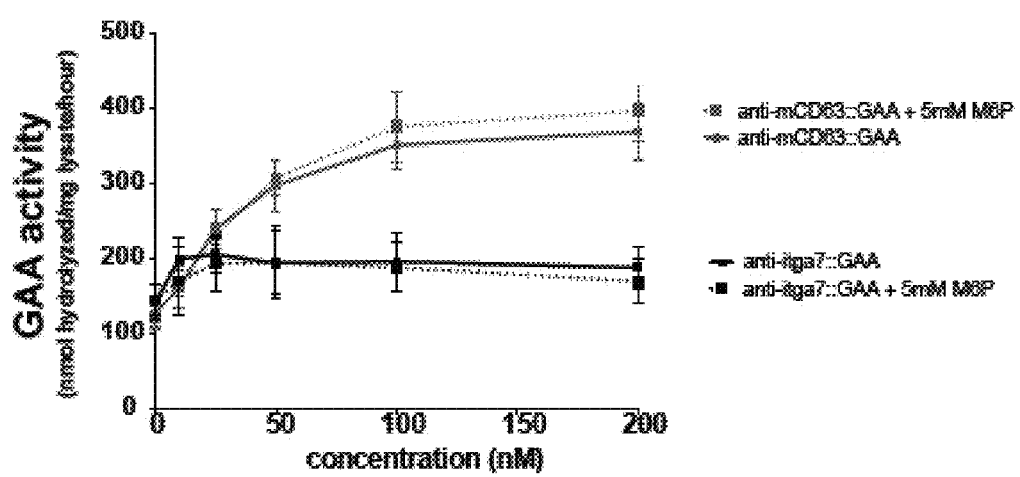
Figure 10B:
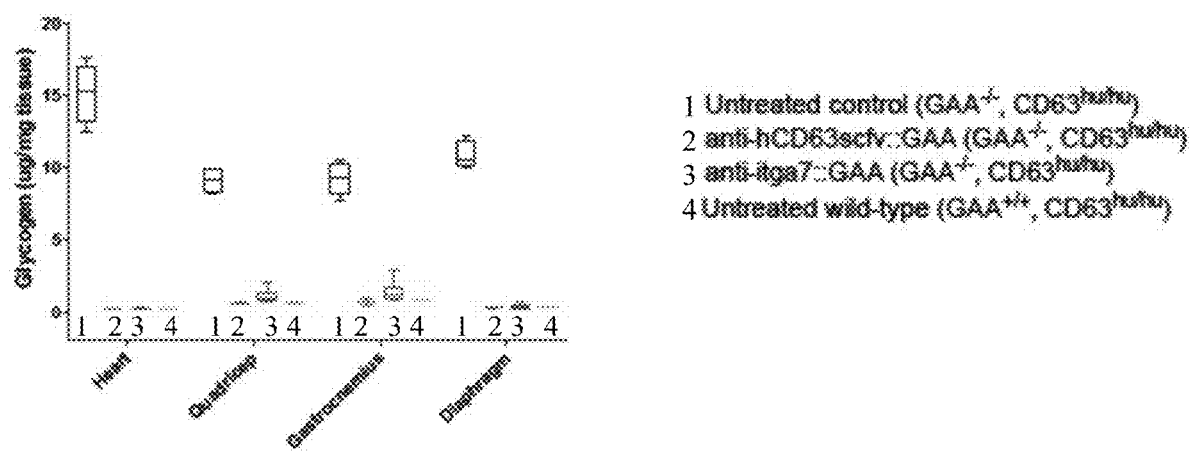

FIG. 10A and FIG. 10B depict the use of other membrane proteins as guides, such as anti-ITGA7 (Integrin alpha-7) scFv fusion proteins to guide GAA. FIG. 10A shows GAA activity (y-axis) of of C2C12 mouse myoblasts incubated overnight with anti-mouse CD63-GAA or anti-moue ITGA7-GAA with or without the presence of 5 mM M6P. FIG. 10B shows GAA KO mice humanized for CD63 (GAA−/−; CD63hu/hu) that were given plasmids encoding an scFv::GAA format of anti-hCD63::GAA (2) or a full-length IgG4::GAA format of anti-mouse integrin alpha-7 (3) by hydrodynamic delivery (HDD), then tissue glycogen levels were measured 3 weeks post-HDD. Untreated control mice, GAA−/−; CD63hu/hu (1) and untreated wild-type GAA control mice, GAA+/+; CD63hu/hu (4) were also tested for glycogen levels in the same tissues.

Figure 11:
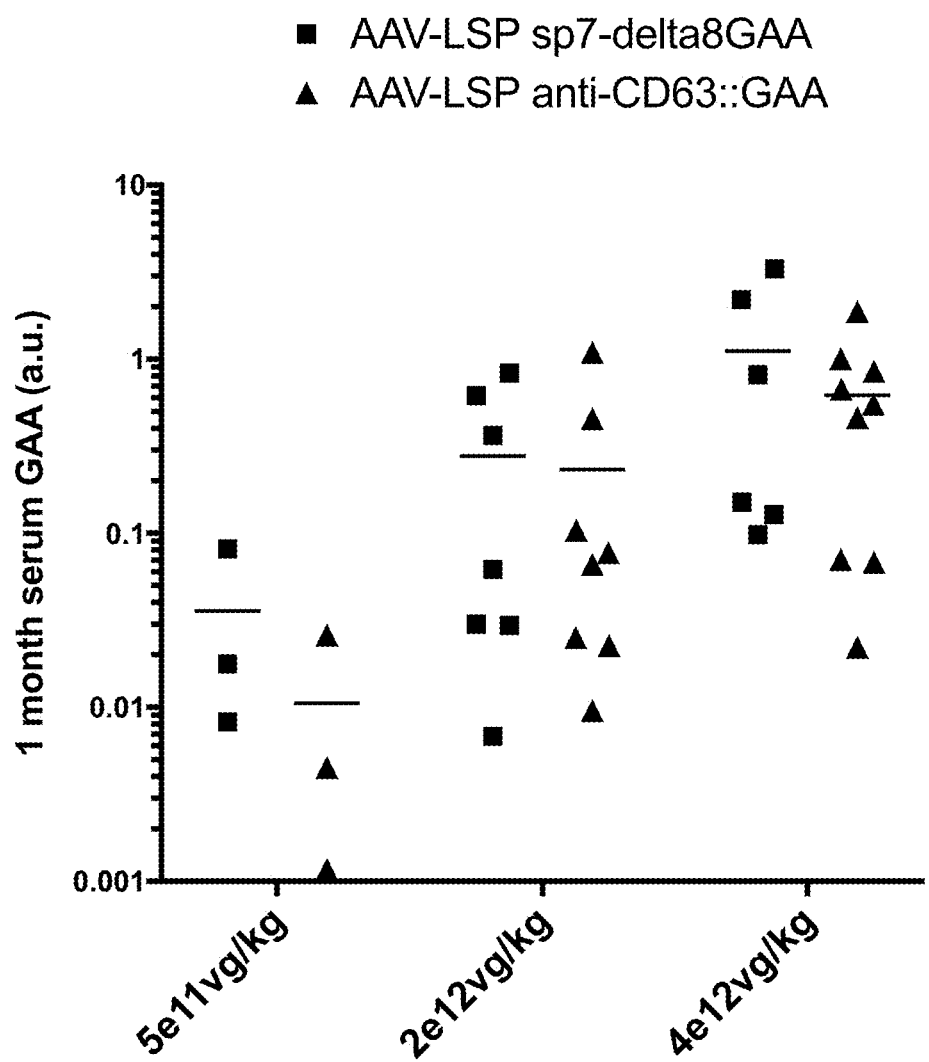

FIG. 11 is a dot plot depicting serum levels of GAA (arbitrary units "a.u."; y-axis) at one-month post-AAV injection as a function of as a function of enzyme construct and dose. Squares represent AAV-LSP-48GAA. Pyramids represent AAV-anti-hCD63scFv::GAA. Both constructs provided a liver-specific promoter (LSP) to drive expression). Dose is provided as viral genome (vg) per kilogram (kg) of the mouse.

Figure 12:
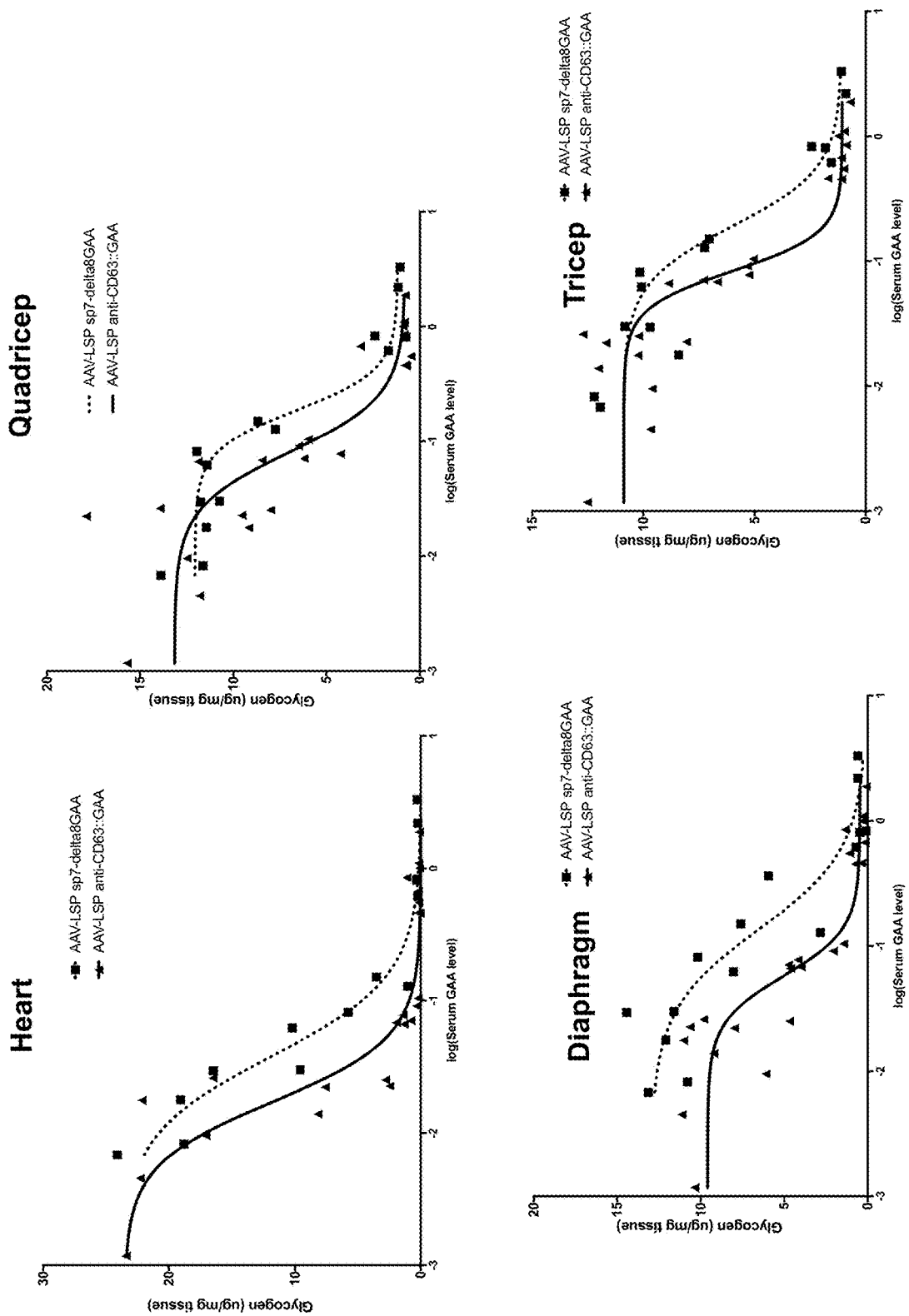

FIG. 12 provides dot blots depicting the levels of glycogen in micrograms per milligram of tissue (heart, quadricep, diaphragm, or tricep) as a function of GAA serum levels. Squares represent AAV-LSP-48GAA. Pyramids represent AAV-anti-hCD63scFv::GAA. Both constructs provided a liver-specific promoter (LSP) to drive expression).

DESCRIPTION

This invention is not limited to particular embodiments, compositions, methods and experimental conditions described, as such embodiments, compositions, methods and conditions may vary. The terminology used herein is for the purpose of describing particular embodiments only, and is not intended to be limiting, since the scope of the present invention will be limited only by the appended claims.

Although any methods and materials similar or equivalent to those described herein can be used in the practice or testing of the present invention, some preferred methods and materials are now described. All publications cited herein are incorporated herein by reference to describe in their entirety. Unless defined otherwise, all technical and scientific terms used herein have the same meaning as commonly understood by one of ordinary skill in the art to which this invention belongs.

"Enzyme-deficiency diseases" include non-lysosomal storage disease such as Krabbe disease (galactosylceramidase), phenylketonuria, galactosemia, maple syrup urine disease, mitochondrial disorders, Friedreich ataxia, Zellweger syndrome, adrenoleukodystrophy, Wilson disease, hemochromatosis, ornithine transcarbamylase deficiency, methylmalonic academia, propionic academia, and lysosomal storage diseases. "Lysosomal storage diseases" include any disorder resulting from a defect in lysosome function. Currently, approximately 50 lysosomal storage disorders have been identified, the most well-known of which include Tay-Sachs, Gaucher, and Niemann-Pick disease. The pathogeneses of the diseases are ascribed to the buildup of incomplete degradation products in the lysosome, usually due to loss of protein function. Lysosomal storage diseases are caused by loss-of-function or attenuating variants in the proteins whose normal function is to degrade or coordinate degradation of lysosomal contents. The proteins affiliated with lysosomal storage diseases include enzymes, receptors and other transmembrane proteins (e.g., NPC1), post-translational modifying proteins (e.g., sulfatase), membrane transport proteins, and non-enzymatic cofactors and other soluble proteins (e.g., GM2 ganglioside activator). Thus, lysosomal storage diseases encompass more than those disorders caused by defective enzymes per se, and include any disorder caused by any molecular defect. Thus, as used herein, the term "enzyme" is meant to encompass those other proteins associated with lysosomal storage diseases.

The nature of the molecular lesion affects the severity of the disease in many cases, i.e. complete loss-of-function tends to be associated with pre-natal or neo-natal onset, and involves severe symptoms; partial loss-of-function is associated with milder (relatively) and later-onset disease. Generally, only a small percentage of activity needs to be restored to have to correct metabolic defects in deficient cells. Table 1 lists some of the more common lysosomal storage diseases and their associated loss-of-function proteins. Lysosomal storage diseases are generally described in Desnick and Schuchman, 2012.

Lysosomal storage diseases can be categorized according to the type of product that accumulates within the defective lysosome. Sphingolipidoses are a class of diseases that affect the metabolism of sphingolipids, which are lipids containing fatty acids linked to aliphatic amino alcohols (reviewed in S. Hakomori, "Glycosphingolipids in Cellular Interaction, Differentiation, and Oncogenesis," 50 Annual Review of Biochemistry 733-764, July 1981). The accumulated products of sphingolipidoses include gangliosides (e.g., Tay-Sachs disease), glycolipids (e.g., Fabry's disease), and glucocerebrosides (e.g., Gaucher's disease).

Mucopolysaccharidoses are a group of diseases that affect the metabolism of glycosaminoglycans (GAGS or mucopolysaccharides), which are long unbranched chains of repeating disaccharides that help build bone, cartilage, tendons, corneas, skin and connective tissue (reviewed in J. Muenzer, "Early initiation of enzyme replacement therapy for the mucopolysaccharidoses," 111(2) Mol. Genet. Metab. 63-72 (February 2014); Sasisekharan et al., "Glycomics approach to structure-function relationships of glycosaminoglycans," 8(1) Ann. Rev. Biomed. Eng. 181-231 (December 2014)). The accumulated products of mucopolysaccharidoses include heparan sulfate, dermatan sulfate, keratin sulfate, various forms of chondroitin sulfate, and hyaluronic acid. For example, Morquio syndrome A is due to a defect in the lysosomal enzyme galactose-6-sulfate sulfatase, which results in the lysosomal accumulation of keratin sulfate and chondroitin 6-sulfate.

Glycogen storage diseases (a.k.a., glycogenosis) result from a cell's inability to metabolize (make or break-down) glycogen. Glycogen metabolism is moderated by various enzymes or other proteins including glucose-6-phosphatase, acid alpha-glucosidase, glycogen de-branching enzyme, glycogen branching enzyme, muscle glycogen phosphorylase, liver glycogen phosphorylase, muscle phosphofructokinase, phosphorylase kinase, glucose transporter, aldolase A, beta-enolase, and glycogen synthase. An exemplar lysosomal storage/glycogen storage disease is Pompe's disease, in which defective acid alpha-glucosidase causes glycogen to accumulate in lysosomes. Symptoms include hepatomegaly, muscle weakness, heart failure, and in the case of the infantile variant, death by age 2 (see DiMauro and Spiegel, "Progress and problems in muscle glycogenosis," 30(2) Acta Myol. 96-102 (October 2011)).

"Multidomain therapeutic protein" includes (i) a single protein that contains more than one functional domain, (ii) a protein that contains more than one polypeptide chain, and (iii) a mixture of more than one protein or more than one polypeptide. The term polypeptide is generally taken to mean a single chain of amino acids linked together via peptide bonds. The term protein encompasses the term polypeptide, but also includes more complex structures. That is, a single polypeptide is a protein, and a protein can contain one or more polypeptides associated in a higher order structure. For example, hemoglobin is a protein containing four polypeptides: two alpha globin polypeptides and two beta globin polypeptides. Myoglobin is also a protein, but it contains only a single myoglobin polypeptide.

The multidomain therapeutic protein comprises one or more polypeptide(s) and at least two domains providing two functions. One of those domains is the "enzyme domain" which provides the replacement of a defective protein activity associated with an enzyme deficiency disease. The other of those domains is the "delivery domain" which provides binding to an internalization effector. Thus, a single polypeptide that provides an enzyme replacement activity and the ability to bind to an internalization effector (a.k.a. internalization effector-binding protein (delivery domain activity) is a multidomain therapeutic protein. Also, a mixture of proteins, wherein one protein provides the enzyme function, and another protein provides the internalization effector binding activity, is a multidomain therapeutic protein. FIG. 1A depicts various exemplars of multidomain therapeutic proteins. In one example (FIG. 1A, panel A), the multidomain therapeutic protein contains an enzyme (represented by the hexagon) and a bispecific antibody (the IE-BP) that binds the enzyme (hashed lines) and an internalization effector (solid lines). Here, one arm of the bispecific antibody binds non-covalently to the enzyme, and the other arm binds non-covalently to the internalization effector, thereby enabling the internalization of the replacement enzyme into the cell or subcellular compartment. In another example (panel B), the multidomain therapeutic protein comprises a single protein containing two polypeptides, one polypeptide having enzyme function and the other having delivery domain function. Here, the enzyme is fused to an immunoglobulin Fc domain or heavy chain constant region, which associates with the Fc domain of the enzyme half-antibody to form the bifunctional multidomain therapeutic protein. The embodiment depicted in panel B is similar to that in panel A, except that the enzyme is covalently attached to one of the half-antibodies, rather than through antigen-antibody interaction at the immunoglobulin variable domain of the half-antibody.

In other examples, the multidomain therapeutic protein consists of the enzyme covalently linked (directly or indirectly through a linker) to the delivery domain. In one embodiment, the enzyme is attached to the C-terminus of an immunoglobulin molecule (e.g., the heavy chain or alternatively the light chain). In another embodiment, the enzyme is attached to the N-terminus of the immunoglobulin molecule (e.g., the heavy chain or alternatively the light chain). In these exemplars, the immunoglobulin molecule is the delivery domain. In yet another embodiment, the enzyme is attached to the C-terminus of a scFv molecule that binds the internalization effector.

In one embodiment, the multidomain therapeutic protein comprises two delivery domains. In one embodiment, the first delivery domain binds to a lysosomal trafficking molecule or other internalization effector (e.g., CD63). In another embodiment, the second delivery domain binds to a transcytosis effector to facilitate transcellular transport of the multidomain therapeutic protein. In one embodiment, the transcytosis effector is inter alia an LDL receptor, an IgA receptor, a transferrin receptor, or a neonatal Fc receptor (FcRn). In a specific embodiment, the transcytosis delivery domain comprises a molecule that binds to a transferrin receptor, such as e.g., an anti-transferrin receptor antibody or an anti-transferrin receptor scFv molecule. Tuma and Hubbard, "Transcytosis: Crossing Cellular Barriers," Physiological Reviews, 83(3): 871-935 (1 Jul. 2003) is incorporated herein by reference for cell surface receptors that mediate transcytosis that are useful in the practice of the subject invention.

"Enzyme domain" or "enzyme" denotes any protein associated with the etiology or physiological effect of an enzyme deficiency disease. An enzyme includes the actual enzyme, transport protein, receptor, or other protein that is defective and which is attributed as the molecular lesion that caused the disease. An enzyme also includes any protein that can provide a similar or sufficient biochemical or physiological activity that replaces or circumvents the molecular lesion of the disease. For example, an "isozyme" may be used as an enzyme. Examples of lysosomal storage disease-related proteins include those listed in Table 1 as "Involved Enzyme/Protein" and any known or later discovered protein or other molecule that circumvents the molecular defect of the enzyme-deficiency disease.

In some embodiments, the enzyme is a hydrolase, including esterases, glycosylases, hydrolases that act on ether bonds, peptidases, linear amidases, diphosphatases, ketone hydrolases, halogenases, phosphoamidases, sulfohydrolases, sulfinases, desulfinases, and the like. In some embodiments, the enzyme is a glycosylase, including glycosidases and N-glycosylases. In some embodiments, the enzyme is a glycosidase, including alpha-amylase, beta-amylase, glucan 1,4-alpha-glucosidase, cellulose, endo-1,3(4)-beta-glucanase, inulinase, endo-1,4-beta-xylanase, endo-1,4-b-xylanase, dextranase, chitinase, polygalacturonidase, lysozyme, exo-alpha-sialidase, alpha-glucosidase, beta-glucosidase, alpha-galactosidase, beta-galactosidase, alpha-mannosidase, beta-mannosidase, beta-fructofuranosidase, alpha,alpha-trehalose, beta-glucuronidase, xylan endo-1,3-beta-xylosidase, amylo-alpha-1,6-glucosidase, hyaluronoglucosaminidase, hyaluronoglucuronidase, and the like.

In the case of Pompe disease, in which the molecular defect is a defect in α-glucosidase activity, enzymes include human alpha-glucosidase, and "isozymes" such as other alpha-glucosidases, engineered recombinant alpha-glucosidase, other glucosidases, recombinant glucosidases, any protein engineered to hydrolyze a terminal non-reducing 1-4 linked alpha-glucose residue to release a single alpha-glucose molecule, any EC 3.2.1.20 enzyme, natural or recombinant low pH carbohydrate hydrolases for glycogen or starches, and glucosyl hydrolases such as sucrase isomaltase, maltase glucoamylase, glucosidase II, and neutral alpha-glucosidase.

An "internalizing effector" includes a protein that is capable of being internalized into a cell or that otherwise participates in or contributes to retrograde membrane trafficking. In some instances, the internalizing effector is a protein that undergoes transcytosis; that is, the protein is internalized on one side of a cell and transported to the other side of the cell (e.g., apical-to-basal). In many embodiments, the internalizing effector protein is a cell surface-expressed protein or a soluble extracellular protein. However, the present invention also contemplates embodiments in which the internalizing effector protein is expressed within an intracellular compartment such as the endosome, endoplasmic reticulum, Golgi, lysosome, etc. For example, proteins involved in retrograde membrane trafficking (e.g., pathways from early/recycling endosomes to the trans-Golgi network) may serve as internalizing effector proteins in various embodiments of the present invention. In any event, the binding of the delivery domain to an internalizing effector protein causes the entire multidomain therapeutic protein, and any molecules associated therewith (e.g., enzyme), to also become internalized into the cell. As explained below, internalizing effector proteins include proteins that are directly internalized into a cell, as well as proteins that are indirectly internalized into a cell.

Internalizing effector proteins that are directly internalized into a cell include membrane-associated molecules with at least one extracellular domain (e.g., transmembrane proteins, GPI-anchored proteins, etc.), which undergo cellular internalization, and are preferably processed via an intracellular degradative and/or recycling pathway. Specific non-limiting examples of internalizing effector proteins that are directly internalized into a cell include, e.g., CD63, MHC-I (e.g., HLA-B27), Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), MAL (Myelin And Lymphocyte protein, a.k.a. VIP17), IGF2R, vacuolar-type H+ ATPase, diphtheria toxin receptor, folate receptor, glutamate receptors, glutathione receptor, leptin receptors, scavenger receptors (e.g., SCARA1-5, SCARB1-3, CD36), and the like.

In certain embodiments, the internalizing effector is prolactin receptor (PRLR). It was discovered that PRLR is, not only a target for certain therapeutic applications, but also an effective internalizing effector protein on the basis of its high rate of internalization and turn-over. The potential for PRLR as an internalizing effector protein, for example, is illustrated in WO2015/026907, where it is demonstrated, inter alia, that anti-PRLR antibodies are effectively internalized by PRLR-expressing cells in vitro.

In certain embodiments, the internalization effector is a kidney specific internalizer, such as CDH16 (Cadheri-16), CLDN16 (Claudn-16), KL (Klotho), PTH1R (parathyroid hormone receptor), SLC22A13 (Solute carrier family 22 member 13), SLC5A2 (Sodium/glucose cotransporter 2), and UMOD (Uromodulin). In other certain embodiments, the internalization effector is a muscle specific internalizer, such as BMPR1A (Bone morphogenetic protein receptor 1A), m-cadherin, CD9, MuSK (muscle-specific kinase), LGR4/GPR48 (G protein-coupled receptor 48), cholinergic receptor (nicotinic) alpha 1, CDH15 (Cadheri-15), ITGA7 (Integrin alpha-7), CACNG1 (L-type calcium channel subunit gamma-1), CACNA1S (L-type calcium channel subunit alpha-15), CACNG6 (L-type calcium channel subunit gamma-6), SCN1B (Sodium channel subunit beta-1), CHRNA1 (ACh receptor subunit alpha), CHRND (ACh receptor subunit delta), LRRC14B (Leucine-rich repeat-containing protein 14B), dystroglycan (DAG1), and POPDC3 (Popeye domain-containing protein 3). In some specific embodiments, the internalization effector is ITGA7, CD9, CD63, ALPL2, ASGR1, ASGR2, or PRLR.

In those embodiments in which the internalization effector (IE) is directly internalized into a cell, the delivery domain can be, e.g., an antibody or antigen-binding fragment of an antibody that specifically binds the IE, or a ligand or portion of a ligand that specifically interacts with the IE. For example, if the IE is Kremen-1 or Kremen-2, the delivery domain can comprise or consist of a Kremen ligand (e.g., DKK1) or Kremen-binding portion thereof. As another example, if the IE is a receptor molecule such as ASGR1, the delivery domain can comprise or consist of a ligand specific for the receptor (e.g., asialoorosomucoid [ASOR] or Beta-GalNAc) or a receptor-binding portion thereof.

Internalizing effector proteins that are indirectly internalized into a cell include proteins and polypeptides that do not internalize on their own, but become internalized into a cell after binding to or otherwise associating with a second protein or polypeptide that is directly internalized into the cell. Proteins that are indirectly internalized into a cell include, e.g., soluble ligands that are capable of binding to an internalizing cell surface-expressed receptor molecule. A non-limiting example of a soluble ligand that is (indirectly) internalized into a cell via its interaction with an internalizing cell surface-expressed receptor molecule is transferrin. In embodiments wherein the IE is transferrin (or another indirectly internalized protein), the binding of the delivery domain to the IE, and the interaction of IE with transferrin receptor (or another internalizing cell-surface expressed receptor molecule), causes the entire delivery domain, and any molecules associated therewith (e.g., the enzyme), to become internalized into the cell concurrent with the internalization of the IE and its binding partner.

In those embodiments in which the IE is indirectly internalized into a cell, the delivery domain can be, e.g., an antibody, antigen-binding fragment of an antibody, or an scFv that specifically binds IE, or a receptor or portion of a receptor that specifically interacts with the soluble effector protein. For example, if the IE is a cytokine, the delivery domain can comprise or consist of the corresponding cytokine receptor or ligand-binding portion thereof.

An exemplar IE is CD63, which is a member of the tetraspanin superfamily of cell surface proteins that span the cell membrane four times. CD63 is expressed in virtually all tissues and is thought to be involved in forming and stabilizing signaling complexes. CD63 localizes to the cell membrane, lysosomal membrane, and late endosomal membrane. CD63 is known to associate with integrins and may be involved in epithelial-mesenchymal transitioning. See H. Maecker et al., "The tetraspanin superfamily: molecular facilitators," 11(6) FASEB J. 428-42, May 1997; and M. Metzelaar et al., "CD63 antigen. A novel lysosomal membrane glycoprotein, cloned by a screening procedure for intracellular antigens in eukaryotic cells," 266 J. Biol. Chem. 3239-3245, 1991.

Another exemplar IE is amyloid beta (A4) precursor-like protein 2 ("APLP2"), a ubiquitously expressed member of the APP (amyloid precursor protein) family. APLP2 is a membrane-bound protein known to interact with major histocompatibility complex (MHC) class I molecules (e.g., Kd). It binds Kd at the cell surface and is internalized in a clathrin-dependent manner with Kd in tow. See Tuli et al., "Mechanism for amyloid precursor-like protein 2 enhancement of major histocompatibility complex class I molecule degradation," 284 The Journal of Biological Chemistry 34296-34307 (2009).

Another IE exemplar is the prolactin receptor (PRLR). The prolactin receptor is a member of the type I cytokine receptor family and upon ligand binding and subsequent dimerization activates "the tyrosine kinases Jak2, Fyn and Tec, the phosphatase SHP-2, the guanine nucleotide exchange factor Vav, and the signaling suppressor SOCS," (see Clevenger and Kline, "Prolactin receptor signal transduction," 10(10) Lupus 706-18 (2001), abstract). The prolactin receptor undergoes endocytic recycling and can be found in lysosomal fractions. See Genty et al., "Endocytosis and degradation of prolactin and its receptor in Chinese hamster ovary cells stably transfected with prolactin receptor cDNA," 99(2) Mol. Cell Endocrinol. 221-8 (1994); and Ferland et al., "The effect of chloroquine on lysosomal prolactin receptors in rat liver," 115(5) Endocrinology 1842-9 (1984).

As used herein, "immunological reaction" generally means a patient's immunological response to an outside or 37 non-self" protein. This immunological response includes an allergic reaction and the development of antibodies that interfere with the effectiveness of the replacement enzyme. Some patients may not produce any of the non-functioning protein, thus rendering the replacement enzyme a "foreign" protein. For example, repeated injection of recombinant GLA (rGLA) to those Fabry patients who lack GLA frequently results in an allergic reaction. In other patients, the production of antibodies against rGLA has been shown to decrease the effectiveness of the replacement enzyme in treating the disease. See for example Tajima et al. ("Use of a Modified α-N-Acetylgalactosaminidase (NAGA) in the Development of Enzyme Replacement Therapy for Fabry Disease," 85(5) Am. J. Hum. Genet. 569-580 (2009)), which discusses the use of modified NAGA as the "isozyme" to replace GLA. The modified NAGA has no immunological cross-reactivity with GLA, and "did not react to serum from a patient with Fabry disease recurrently treated with a recombinant GLA." Id, abstract.

An "immunosuppressive agent" includes drugs and/or proteins that result in general immunosuppression, and may be used to prevent cross-reactive immunological materials (CRIM) against replacement enzymes, e.g., GAA or GLA respectively in a patient with Pompe or Fabry's disease. Non-limiting examples of an immunosuppressive agent include methotrexate, mycophenolate mofetil, cyclophosphamide, rapamycin DNA alkylating agents, anti-CD20 antibody, anti-BAFF antibody, anti-CD3 antibody, anti-CD4 antibody, and any combination thereof.

Regulatory elements, e.g., promoters, that are specific to a tissue, e.g., liver, enhance expression of nucleic acid sequences, e.g., genes, under the control of such regulatory element in the tissue for which the regulatory element is specific. Non-limiting examples of a liver specific regulatory element, e.g., liver specific promoters, may be found in Chuah et al. (2014) *Mol. Ther.* 22:1605-13.

The term "protein" means any amino acid polymer having more than about 20 amino acids covalently linked via amide bonds. Proteins contain one or more amino acid polymer chains, generally known in the art as "polypeptides". Thus, a polypeptide may be a protein, and a protein may contain multiple polypeptides to form a single functioning biomolecule. Disulfide bridges (i.e., between cysteine residues to form cystine) may be present in some proteins. These covalent links may be within a single polypeptide chain, or between two individual polypeptide chains. For example, disulfide bridges are essential to proper structure and function of insulin, immunoglobulins, protamine, and the like. For a recent review of disulfide bond formation, see Oka and Bulleid, "Forming disulfides in the endoplasmic reticulum," 1833(11) Biochim Biophys Acta 2425-9 (2013).

As used herein, "protein" includes biotherapeutic proteins, recombinant proteins used in research or therapy, trap proteins and other Fc-fusion proteins, chimeric proteins, antibodies, monoclonal antibodies, human antibodies, bispecific antibodies, antibody fragments, nanobodies, recombinant antibody chimeras, scFv fusion proteins, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," 28 Biotechnol Genet Eng Rev. 147-75 (2012).

The term "antibody", as used herein, includes immunoglobulin molecules comprising four polypeptide chains, two heavy (H) chains and two light (L) chains inter-connected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. The term "high affinity" antibody refers to those antibodies having a binding affinity to their target of at least $10^{-9}$ M, at least $10^{-10}$M; at least $10^{-11}$ M; or at least $10^{-12}$M, as measured by surface plasmon resonance, e.g., BIACORE™ or solution-affinity ELISA. The term "antibody" may encompass any type of antibody, such as e.g. monoclonal or polyclonal. Moreover, the antibody may be or any origin, such as e.g. mammalian or non-mammalian. In one embodiment, the antibody may be mammalian or avian. In a further embodiment, the antibody may be or human origin and may further be a human monoclonal antibody.

The phrase "bispecific antibody" includes an antibody capable of selectively binding two or more epitopes. Bispecific antibodies generally comprise two different heavy chains, with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes.

The phrase "heavy chain," or "immunoglobulin heavy chain" includes an immunoglobulin heavy chain constant region sequence from any organism, and unless otherwise specified includes a heavy chain variable domain. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an antigen (e.g., recognizing the antigen with a KD in the micromolar, nanomolar, or picomolar range), that is capable of expressing and secreting from a cell, and that comprises at least one CDR.

The phrase "light chain" includes an immunoglobulin light chain constant region sequence from any organism, and unless otherwise specified includes human kappa and lambda light chains. Light chain variable (VL) domains typically include three light chain CDRs and four framework (FR) regions, unless otherwise specified. Generally, a full-length light chain includes, from amino terminus to carboxyl terminus, a VL domain that includes FR1-CDR1-FR2-CDR2-FR3-CDR3-FR4, and a light chain constant domain. Light chains that can be used with this invention include e.g., those, that do not selectively bind either the first or second antigen selectively bound by the antigen-binding protein. Suitable light chains include those that can be identified by screening for the most commonly employed light chains in existing antibody libraries (wet libraries or in silico), where the light chains do not substantially interfere with the affinity and/or selectivity of the antigen-binding domains of the antigen-binding proteins. Suitable light chains include those that can bind one or both epitopes that are bound by the antigen-binding regions of the antigen-binding protein.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4. A "variable domain" includes an amino acid sequence capable of folding into a canonical domain (VH or VL) having a dual beta sheet structure wherein the beta sheets are connected by a disulfide bond between a residue of a first beta sheet and a second beta sheet.

The phrase "complementarity determining region," or the term "CDR," includes an amino acid sequence encoded by a nucleic acid sequence of an organism's immunoglobulin genes that normally (i.e., in a wildtype animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "antibody fragment", refers to one or more fragments of an antibody that retain the ability to specifically bind to an antigen. Examples of binding fragments encompassed within the term "antibody fragment" include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) PNAS USA 90:6444-6448; Poljak et al. (1994) Structure 2:1121-1123).

The phrase "Fc-containing protein" includes antibodies, bispecific antibodies, immunoadhesins, and other binding proteins that comprise at least a functional portion of an immunoglobulin CH2 and CH3 region. A "functional portion" refers to a CH2 and CH3 region that can bind a Fc receptor (e.g., an FcγR; or an FcRn, i.e., a neonatal Fc receptor), and/or that can participate in the activation of complement. If the CH2 and CH3 region contains deletions, substitutions, and/or insertions or other modifications that render it unable to bind any Fc receptor and also unable to activate complement, the CH2 and CH3 region is not functional.

Fc-containing proteins can comprise modifications in immunoglobulin domains, including where the modifications affect one or more effector function of the binding protein (e.g., modifications that affect FcγR binding, FcRn binding and thus half-life, and/or CDC activity). Such modifications include, but are not limited to, the following modifications and combinations thereof, with reference to EU numbering of an immunoglobulin constant region: 238, 239, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, the binding protein is an Fc-containing protein and exhibits enhanced serum half-life (as compared with the same Fc-containing protein without the recited modification(s)) and have a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/SI/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); a 307 and/or 308 modification (e.g., 308F or 308P).

The term "antigen-binding protein," as used herein, refers to a polypeptide or protein (one or more polypeptides complexed in a functional unit) that specifically recognizes an epitope on an antigen, such as a cell-specific antigen and/or a target antigen of the present invention. An antigen-binding protein may be multi-specific. The term "multi-specific" with reference to an antigen-binding protein means that the protein recognizes different epitopes, either on the same antigen or on different antigens. A multi-specific antigen-binding protein of the present invention can be a single multifunctional polypeptide, or it can be a multimeric complex of two or more polypeptides that are covalently or non-covalently associated with one another. The term "antigen-binding protein" includes antibodies or fragments thereof of the present invention that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bispecific or a multi-specific antigen-binding molecule with a second binding specificity.

As used herein, the term "epitope" refers to the portion of the antigen which is recognized by the multi-specific antigen-binding polypeptide. A single antigen (such as an antigenic polypeptide) may have more than one epitope. Epitopes may be defined as structural or functional. Functional epitopes are generally a subset of structural epitopes and are defined as those residues that directly contribute to the affinity of the interaction between the antigen-binding polypeptide and the antigen. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. Epitopes formed from contiguous amino acids are typically retained on exposure to denaturing solvents, whereas epitopes formed by tertiary folding are typically lost on treatment with denaturing solvents.

The term "domain" refers to any part of a protein or polypeptide having a particular function or structure. Preferably, domains of the present invention bind to cell-specific or target antigens. Cell-specific antigen- or target antigen-binding domains, and the like, as used herein, include any naturally occurring, enzymatically obtainable, synthetic, or genetically engineered polypeptide or glycoprotein that specifically binds an antigen.

The term "half-body" or "half-antibody", which are used interchangeably, refers to half of an antibody, which essentially contains one heavy chain and one light chain. Antibody heavy chains can form dimers, thus the heavy chain of one half-body can associate with heavy chain associated with a different molecule (e.g., another half-body) or another Fc-containing polypeptide. Two slightly different Fc-domains may "heterodimerize" as in the formation of bispecific antibodies or other heterodimers, -trimers, -tetramers, and the like. See Vincent and Murini, "Current strategies in antibody engineering: Fc engineering and pH-dependent antigen binding, bispecific antibodies and antibody drug conjugates," 7 Biotechnol. J. 1444-1450 (20912); and Shimamoto et al., "Peptibodies: A flexible alternative format to antibodies," 4(5) MAbs 586-91 (2012).

In one embodiment, the half-body variable domain specifically recognizes the internalization effector and the half body Fc-domain dimerizes with an Fc-fusion protein that comprises a replacement enzyme (e.g., a peptibody) Id, 586.

The term "single-chain variable fragment" or "scFv" includes a single chain fusion polypeptide containing an immunoglobulin heavy chain variable region (VH) and an immunoglobulin light chain variable region (VL). In some embodiments, the VH and VL are connect by a linker sequence of 10 to 25 amino acids. ScFv polypeptides may also include other amino acid sequences, such as CL or CH1 regions. ScFv molecules can be manufactured by phage display or made by directly subcloning the heavy and light chains from a hybridoma or B-cell. Ahmad et al., Clinical and Developmental Immunology, volume 2012, article ID 98025 is incorporated herein by reference for methods of making scFv fragments by phage display and antibody domain cloning.

"Alpha-glucosidase" (or "α-glucosidase"), "α-glucosidase activity", "GAA", and "GAA activity" are used interchangeably and refer to any protein that facilitates the hydrolysis of 1,4-alpha bonds of glycogen and starch into glucose. GAA is also known inter alia as EC 3.2.1.20, maltase, glucoinvertase, glucosidosucrase, maltase-glucoamylase, alpha-glucopyranosidase, glucosidoinvertase, alpha-D-glucosidase, alpha-glucoside hydrolase, alpha-1,4-glucosidase, and alpha-D-glucoside glucohydrolase. GAA can be found in the lysosome and at the brush border of the small intestine. Patients who suffer from Pompe disease lack functioning lysosomal α-glucosidase. See S. Chiba, "Molecular mechanism in alpha-glucosidase and glucoamylase," 61(8) Biosci. Biotechnol. Biochem. 1233-9 (1997); and Hesselink et al., "Lysosomal dysfunction in muscle with special reference to glycogen storage disease type II," 1637 (2) Biochim. Biophys. Acta. 164-70 (2003).

"Alpha-galactosidase A" (or "α-galactosidase A"), "α-galactosidase A activity", "α-galactosidase", "α-galactosidase activity", "GLA", and "GLA activity" are used interchangeably and refer to any protein that facilitates the hydrolysis of terminal α-galactosyl moieties from glycolipids and glycoproteins, and also hydrolyses α-D-fucosides. GLA is also known inter alia as EC 3.2.1.22, melibiase, α-D-galactosidase, α-galactosidase A, α-galactoside galactohydrolase, α-D-galactoside galactohydrolase. GLA is a lysosomal enzyme encoded by the X-linked GLA gene. Defects in GLA can lead to Fabry Disease, in which the glycolipid known as globotriaosylceramide (a.k.a. Gb3, GL-3, or ceramide trihexoside) accumulates within blood vessels (i.e., prominent vasculopathy), resulting in pain and impairment in the function of kidney, heart, skin, and/or cerebrovascular tissues. and other tissues, and organs. See for example Prabakaran et al. "Mannose 6-phosphate receptor and sortilin mediated endocytosis of α-galactosidase A in kidney endothelial cells," 7(6) PLoS One e39975 pp. 1-9 (2012).

In one aspect, the invention provides a method of treating a patient (or subject) suffering from a lysosomal storage disease by administering to the patient a "multidomain therapeutic protein". The multidomain therapeutic protein enters the cells of the patient and delivers to the lysosomes an enzyme or enzymatic activity that (i.e., "replacement enzyme") that replaces the enzyme (i.e, "endogenous enzyme") or enzymatic activity that is associated with the LSD. In one embodiment, the multidomain therapeutic protein is delivered to the patient via a gene therapy vector that contains a polynucleotide that encodes the multidomain therapeutic protein.

LSDs include sphingolipidoses, a mucopolysaccharidoses, and glycogen storage diseases. In some embodiments, the LSD is any one or more of Fabry disease, Gaucher disease type I, Gaucher disease type II, Gaucher disease type III, Niemann-Pick disease type A, Niemann-Pick disease type BGM1-gangliosidosis, Sandhoff disease, Tay-Sachs disease, GM2-activator deficiency, GM3-gangliosidosis, metachromatic leukodystrophy, sphingolipid-activator deficiency, Scheie disease, Hurler-Sceie disease, Hurler disease, Hunter disease, Sanfilippo A, Sanfilippo B, Sanfilippo C, Sanfilippo D, Morquio syndrome A, Morquio syndrome B, Maroteaux-Lamy disease, Sly disease, MPS IX, and Pompe disease. In a specific embodiment, the LSD is Fabry disease. In another embodiment, the LSD is Pompe disease.

In some embodiments, the multidomain therapeutic protein comprises (a) the replacement enzyme, and (b) a molecular entity that binds an internalization effector (delivery domain). In some cases, the replacement enzyme is any one or more of α-galactosidase, β-galactosidase, α-glucosidase, β-glucosidase, saposin-C activator, ceramidase, sphingomyelinase, β-hexosaminidase, GM2 activator, GM3 synthase, arylsulfatase, sphingolipid activator, α-iduronidase, iduronidase-2-sulfatase, heparin N-sulfatase, N-acetyl-α-glucosaminidase, α-glucosamide N-acetyltransferase, N-acetylglucosamine-6-sulfatase, N-acetylgalactosamine-6-sulfate sulfatase, N-acetylgalactosamine-4-sulfatase, β-glucuronidase, and hyaluronidase.

In some cases, the patient may not make sufficient protein such that a replacement enzyme is recognized by the patient as "non-self" and an immunological reaction ensues after administering a replacement enzyme. This is not desirable. Therefore, in some embodiments, the replacement enzyme is designed or produced in such a way as to avoid inducing an immunological reaction in the subject. One such solution is to use an "isozyme" as a replacement enzyme. An isozyme is sufficiently close to a "self" protein of the patient, but has the replacement enzyme activity sufficient to ameliorate the symptoms of the LSD.

In one particular embodiment, in which the LSD is Pompe disease and the endogenous enzyme is α-glucosidase (GAA), the isozyme can be any one of acid α-glucosidase, sucrase-isomaltase (SI), maltase-glucoamylase (MGAM), glucosidase II (GANAB), and neutral α-glucosidase (C GNAC). In another particular embodiment, in which the LSD is Fabry disease and the endogenous enzyme is α-galactosidase A (GLA), the isozyme can be an α-N-acetylgalactosaminidase engineered to have GLA activity.

Provided herein are methods, other than to use of a isozyme, to reduce cross-reactive immunological materials (CRIM) against the replacement enzyme. As demonstrated in FIGS. 5 and 6, administration of a multidomain therapeutic protein (e.g., via a gene therapy vector) comprising an internalizing effector binding domain and the enzyme domain reduces the level of CRIM against the replacement enzyme comprised to administration of a control therapeutic protein (lacking the internalizing effector domain and comprising an enzyme domain). As such, in one embodiment or reducing CRIM against an enzyme in a patient with a deficiency in the enzyme comprises administering to the patient the patient a multidomain therapeutic protein (or nucleic acid encoding same, e.g., a gene therapy vector containing a gene encoding the multidomain therapeutic protein, wherein the multidomain therapeutic protein comprises a delivery domain (e.g., internalization effector binding protein) and an enzyme domain.

The multidomain therapeutic protein has an internalization effector binding protein component that enables the uptake of the replacement enzyme into the cell. Thus, in some embodiments, the internalization effector can be CD63, MHC-I, Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), PRLR (prolactin receptor), MAL (Myelin And Lymphocyte protein, a.k.a. VIP17), IGF2R, vacuolar-type H+ ATPase, diphtheria toxin receptor, folate receptor, glutamate receptors, glutathione receptor, leptin receptor, scavenger receptor, SCARA1-5, SCARB1-3, and CD36. In certain embodiments, the internalization effector is a kidney specific internalizer, such as CDH16 (Cadheri-16), CLDN16 (Claudn-16), KL (Klotho), PTH1R (parathyroid hormone receptor), SLC22A13 (Solute carrier family 22 member 13), SLC5A2 (Sodium/glucose cotransporter 2), and UMOD (Uromodulin). In other certain embodiments, the internalization effector is a muscle specific internalizer, such as BMPR1A (Bone morphogenetic protein receptor 1A), m-cadherin, CD9, MuSK (muscle-specific kinase), LGR4/GPR48 (G protein-coupled receptor 48), cholinergic receptor (nicotinic) alpha 1, CDH15 (Cadheri-15), ITGA7 (Integrin alpha-7), CACNG1 (L-type calcium channel subunit gamma-1), CACNA1S (L-type calcium channel subunit alpha-1S), CACNG6 (L-type calcium channel subunit gamma-6), SCN1B (Sodium channel subunit beta-1), CHRNA1 (ACh receptor subunit alpha), CHRND (ACh receptor subunit delta), LRRC14B (Leucine-rich repeat-containing protein 14B), dystroglycan (DAG1), and POPDC3 (Popeye domain-containing protein 3). In some specific embodiments, the internalization effector is ITGA7, CD9, CD63, APLP2, ASGR1, ASGR2, or PRLR.

In some embodiments, the internalization effector-binding protein comprises an antigen-binding protein, which includes for example a receptor-fusion molecule, a trap molecule, a receptor-Fc fusion molecule, an antibody, an Fab fragment, an F(ab')2 fragment, an Fd fragment, an Fv fragment, a single-chain Fv (scFv) molecule, a dAb fragment, an isolated complementarity determining region (CDR), a CDR3 peptide, a constrained FR3-CDR3-FR4 peptide, a domain-specific antibody, a single domain antibody, a domain-deleted antibody, a chimeric antibody, a CDR-grafted antibody, a diabody, a triabody, a tetrabody, a minibody, a nanobody, a monovalent nanobody, a bivalent nanobody, a small modular immunopharmaceutical (SMIP), a camelid antibody (VHH heavy chain homodimeric antibody), and a shark variable IgNAR domain.

In one embodiment, the molecular entity that binds the internalization effector is an antibody, an antibody fragment, or other antigen-binding protein. For example, the molecular entity can be a bispecific antibody, in which one arm binds the internalization effector (e.g., ITGA7, CD9, CD63, PRLR, APLP2. ASGR1, ASGR2), and the other arm binds the replacement enzyme. Here, the multidomain therapeutic protein comprises the bispecific antibody and the replacement enzyme (FIG. 1A). In a specific embodiment, the disease treated is Fabry disease, and the multidomain therapeutic protein comprises GLA and a bispecific antibody that binds GLA and CD63. In a specific embodiment, the disease treated is Fabry disease, and the multidomain therapeutic protein comprises GLA and a bispecific antibody that binds GLA and ITGA7. In another specific embodiment, the disease treated is Pompe disease, and the multidomain therapeutic protein comprises GAA and a bispecific antibody that binds GAA and CD63. In another specific embodiment, the disease treated is Pompe disease, and the multidomain therapeutic protein comprises GAA and a bispecific antibody that binds GAA and ITGA7.

In another embodiment, the molecular entity that binds the internalization effector comprises a half-antibody, and the replacement enzyme contains an Fc domain (enzyme-Fc fusion polypeptide). In one embodiment, the Fc domain of the enzyme-Fc fusion polypeptide associates with the Fc domain of the internalization effector-specific half-body to form the multidomain therapeutic protein (FIG. 1B).

In other embodiments, the replacement enzyme is covalently linked to internalization effector-binding protein. The enzyme-Fc fusion:half-body embodiment described in the previous paragraph (see also FIG. 1B) falls into this class, since the Fc dimer can be secured via one or more disulfide bridges. The covalent linkage between the enzyme activity domain or polypeptide and the internalization-binding domain or polypeptide may be any type of covalent bond, i.e., any bond that involved sharing of electrons. In some cases, the covalent bond is a peptide bond between two amino acids, such that the replacement enzyme and the internalization effector-binding protein in whole or in part form a continuous polypeptide chain, as in a fusion protein. In some cases, the replacement enzyme portion and the internalization effector-binding protein are directly linked. In other cases, a linker is used to tether the two portions. See Chen et al., "Fusion protein linkers: property, design and functionality," 65(10) Adv Drug Deliv Rev. 1357-69 (2013).

In a particular embodiment, the replacement enzyme is covalently linked to the C-terminus of the heavy chain of an anti-internalization effector antibody (see FIG. 1C) or to the C-terminus of the light chain (FIG. 1E). In another particular embodiment, the replacement enzyme is covalently linked to the N-terminus of the heavy chain of an anti-internalization effector antibody (see FIG. 1D) or to the N-terminus of the light chain (FIG. 1F). In another particular embodiment, the enzyme is linked to the C-terminus of an anti-internalization effector scFv domain (FIG. 1G).

In some cases, especially where the replacement enzyme is not normally proteolytically processed in the lysosome, a cleavable linker is added to those embodiments of the multidomain therapeutic protein that comprise an antibody-enzyme fusion. In some embodiments, a cathepsin cleavable linker is inserted between the antibody and the replacement enzyme to facilitate removal of the antibody in the lysosome in order to a) possibly help preserve enzymatic activity by removing the sterically large antibody and b) possibly increase lysosomal half-life of the enzyme.

In one particular embodiment, the multidomain therapeutic protein is delivered to the patient or cell in a gene therapy vector that contains a polynucleotide that encodes the multidomain therapeutic protein. In one embodiment, the multidomain therapeutic protein comprises a delivery domain and an enzyme domain. In a specific embodiment, the delivery domain binds to an internalizing effector, such as CD63, MHC-I, Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), MAL (myelin and lymphocyte protein (MAL), IGF2R, vacuolar-type H+ ATPase, diphtheria toxin receptor, folate receptor, glutamate receptors, glutathione receptor, leptin receptors, scavenger receptor A1-5 (SCARA1-5), SCARB1-3, or CD36. In one embodiment, the delivery domain is a single-chain variable fragment (scFv) that binds to CD63 (i.e., anti-CD63 scFv). In another embodiment, the delivery domain is a single-chain variable fragment (scFv) that binds to ITGA7 (i.e., anti-ITGA7 scFv).

In one particular embodiment, the enzyme domain of the multidomain therapeutic protein comprises a hydrolase. In a specific embodiment, the enzyme domain comprises a hydrolase that is a glycosylase. In a more specific embodiment, the enzyme domain comprises a glycosylase that is a glycosidase. In a more specific embodiment, the enzyme domain is a glycosidase that is alpha-glucosidase.

Generally, disclosed herein are compositions comprising and use of polynucleotides, e.g., (m)RNA, DNA, and modified forms thereof, that encode a multidomain therapeutic protein comprising an internalizing effector domain and an enzyme domain in the treatment of lysosomal storage diseases, e.g., for the reduction of glycogen and/or the enhancement of immune tolerance for GAA in a patient with Pompe disease.

The term "polynucleotide" includes a polymer of nucleotides (e.g., RNA or DNA) that encodes at least one polypeptide, including fusion polypeptides, e.g., a multidomain therapeutic polypeptide comprising an internalizing effector domain and an enzyme domain. Polynucleotide as used herein encompasses polymers comprising both modified and unmodified nucleotides. A polynucleotide may contain one or more coding and non-coding regions. A polynucleotide can be purified from natural sources, produced using recombinant expression systems and optionally purified, chemically synthesized, etc. Where appropriate, e.g., in the case of chemically synthesized molecules, A polynucleotide can comprise nucleoside analogs such as analogs having chemically modified bases or sugars, backbone modifications, etc. A polynucleotide sequence is presented in the 5' to 3' direction unless otherwise indicated. In some embodiments, a polynucleotide is or comprises natural nucleosides (e.g., adenosine, guanosine, cytidine, uridine); nucleoside analogs (e.g., 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, a polynucleotide comprises one or more nonstandard nucleotide residues. The nonstandard nucleotide residues may include, e.g., 5-methyl-cytidine ("5mC"), pseudouridine (".psi.U"), and/or 2-thio-uridine ("2sU"). See, e.g., U.S. Pat. No. 8,278,036 or WO2011012316, each of which is incorporated in its entirety by reference for a discussion of such residues and their incorporation into a polynucleotide. The presence of nonstandard nucleotide residues may render a polynucleotide more stable and/or less immunogenic than a control a polynucleotide with the same sequence but containing only standard residues. In further embodiments, a polynucleotide may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Certain embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the polynucleotide may be complexed or hybridized with additional polynucleotides and/or peptide polynucleotides (PNA). In embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In certain embodiments, any of these modifications may be present in 0-100% of the nucleotides—for example, more than 0%, 1%, 10%, 25%, 50%, 75%, 85%, 90%, 95%, or 100% of the constituent nucleotides individually or in combination. In some embodiments, a polynucleotide comprises messenger RNA (mRNA) molecules, which may or may not be modified, e.g., which may or may not comprise a modified nucleotide, by well-known methods to increase their stability and/or decrease their immunogenicity. In some embodiments, a polynucleotide comprises DNA molecules, which may which may or may not be modified, e.g., which may or may not comprise a modified nucleotide, by well-known methods to increase their stability and/or decrease their immunogenicity.

In some embodiments, the polynucleotide also includes a "locus-targeting nucleic acid sequence". The locus targeting sequence enables the integration of the multidomain therapeutic protein-encoding polynucleotide into the genome of the recipient host cell. In some embodiments, the locus targeting sequence include flanking homology arms to enable homologous recombination. In some embodiments, the locus targeting sequence includes guide RNA sequences and a type II Cas enzyme to facilitate integration (i.e., the CRISPR-Cas9 method). In some embodiments, the locus targeting sequence includes guide zinc-finger nuclease (ZFN) recognition sequences to facilitate integration. In some embodiments, the locus targeting sequence includes transcription activator-like effector nuclease (TALEN) recognition sequences to facilitate integration. In still other embodiments, the locus targeting sequence includes a single residue-to-nucleotide code used by BuD-derived nucleases to facilitate integration.

In some embodiments, the genomic locus into which the multidomain therapeutic protein-encoding polynucleotide is integrated is a "safe harbor locus". In one embodiment, a "safe harbor locus" enables high expression of the multidomain therapeutic protein, while not interfering with the expression of essential genes or promoting the expression of oncogenes or other deleterious genes. In one embodiment, the genomic locus is at or proximal to the liver-expressed albumin (Alb) locus, a EESYR locus, a SARS locus, position 188,083,272 of human chromosome 1 or its non-human mammalian orthologue, position 3,046,320 of human chromosome 10 or its non-human mammalian orthologue, position 67,328,980 of human chromosome 17 or its non-human mammalian orthologue, an adeno-associated virus site 1 (AAVS1which is a naturally occurring site of integration of AAV virus) on human chromosome 19 or its non-human mammalian orthologue, a chemokine receptor 5 (CCR5) gene, a chemokine receptor gene encoding an HIV-1 coreceptor, or a mouse Rosa26 locus or its non-murine mammalian orthologue. In one embodiment, the genomic locus is an adeno-associated virus site. In one embodiment, the genomic locus for integration is selected according to the method of Papapetrou and Schambach, J. Molecular Therapy, vol. 24 (4):678-684, April 2016, which is herein incorporated by reference for the step-wise selection of a safe harbor genomic locus for gene therapy vector integration; see also Barzel et al. Nature, vol. 517:360-364, incorporated herein by reference in its entirety, for the promoterless gene targeting into the liver-expressed albumin (Alb) locus.

In some embodiments, the polynucleotide, e.g., DNA, also contains a promoter operably linked to the multidomain therapeutic protein-encoding nucleic acid sequence. In a specific embodiment, the promoter is a tissue-specific promotor that drives gene expression in a particular tissue. In one embodiment, the tissue specific promoter is a liver-specific enhancer/promoter derived from serpinal (e.g., SEQ ID NO:9) and/or is a TTR promoter (SEQ ID NO:8). In other embodiments, the promoter is a CMV promoter. In other embodiments, the promoter is a ubiquitin C promoter In one embodiment, the multidomain therapeutic protein-encoding "gene therapy vector" is any vector capable of delivering the polynucleotide encoding the multidomain therapeutic protein to a host, e.g., a patient. In some embodiments the gene therapy vector targets a specific host cell or organ, e.g., for local delivery, e.g., tissue specific delivery. Typically, local delivery requires a protein (e.g., a multidomain therapeutic protein) encoded by mRNAs be translated and expressed mainly in and/or by an organ, e.g., a liver, whereby thereby forming a depot, e.g., a liver depot for production (and secretion) of the protein. In some embodiments, a gene therapy vector delivers a multidomain therapeutic protein polynucleotide to the liver in a patient to form a liver depot. See, e.g., DeRosa et al. svol. 10:699-707, incorporated herein by reference in its entirety. In some embodiments, a gene therapy vector delivers a polynucleotide encoding a multidomain therapeutic protein to muscle tissue in a patient. In some embodiments, a gene therapy vector delivers a polynucleotide encoding a multidomain therapeutic protein to the brain of a patient.

Any now-known or future-developed gene therapy delivery vector, natural or engineered, can be used in the practice of this invention. In some embodiments, the gene therapy vector is a viral vector, e.g., comprises a virus, viral capsid, viral genome etc. In some embodiments, the gene therapy vector is a naked polynucleotide, e.g., an episome. In some embodiments, the gene therapy vector comprises a polynucleotide complex. Exemplary non-limiting polynucleotide complexes for use as a gene therapy vector include lipoplexes, polymersomes, polypexes, dendrimers, inorganic nanoparticles (e.g., polynucleotide coated gold, silica, iron oxide, calcium phosphate, etc.). In some embodiments, a gene therapy vector as described herein comprises a combination of a viral vector, naked polynucleotides, and polynucleotide complexes.

In one embodiment, the gene therapy vector is a virus, including a retrovirus, adenovirus, herpes simplex virus, pox virus, vaccinia virus, lentivirus, or an adeno-associated virus. In one embodiment, the gene therapy vector is an adeno-associated virus (AAV), including serotypes AAV1, AAV2, AAV3, AAV4, AAV5, AAV6, AAV7, AAV8, AAV9, AAV10, and AAV11, or engineered or naturally selected variants thereof.

In one embodiment, the polynucleotide also contains adeno-associated virus (AAV) nucleic acid sequence. In one embodiment, the gene therapy vector is a chimeric adeno-associated virus containing genetic elements from two or more serotypes. For example, an AAV vector with rep genes from AAV1 and cap genes from AAV2 (designated as AAV1/2 or AAV RC1/2) may be used as a gene therapy vector to deliver the multidomain therapeutic protein polynucleotide to a cell or a cell of a patient in need. In one embodiment, the gene therapy vector is an AAV1/2, AAV1/3, AAV1/4, AAV1/5, AAV1/6, AAV1/7, AAV1/8, AAV1/9, AAV1/10, AAV1/11, AAV2/1, AAV2/3, AAV2/4, AAV2/5, AAV2/6, AAV2/7, AAV2/8, AAV2/9, AAV2/10, AAV2/11, AAV3/1, AAV3/2, AAV3/4, AAV3/5, AAV3/6, AAV3/7, AAV3/8, AAV3/9, AAV3/10, AAV3/10, AAV4/1, AAV4/2, AAV4/3, AAV4/5, AAV4/6, AAV4/7, AAV4/8, AAV4/9, AAV4/10, AAV4/11, AAV5/1, AAV5/2, AAV5/3, AAV5/4, AAV5/6, AAV5/7, AAV5/8, AAV5/9, AAV5/10, AAV5/11, AAV6/1, AAV6/2, AAV6/3, AAV6/4, AAV6/5, AAV6/7, AAV6/8, AAV6/9, AAV6/10, AAV6/10, AAV7/1, AAV7/2, AAV7/3, AAV7/4, AAV7/5, AAV7/6, AAV7/8, AAV7/9, AAV7/10, AAV7/11, AAV8/1, AAV8/2, AAV8/3, AAV8/4, AAV8/5, AAV8/6, AAV8/7, AAV8/9, AAV8/10, AAV8/11, AAV9/1, AAV9/2, AAV9/3, AAV9/4, AAV9/5, AAV9/6, AAV9/7, AAV9/8, AAV9/10, AAV9/11, AAV10/1, AAV10/2, AAV10/3, AAV10/4, AAV10/5, AAV10/6, AAV10/7, AAV10/8, AAV10/9, AAV10/11, AAV11/1, AAV11/2, AAV11/3, AAV11/4, AAV11/5, AAV11/6, AAV11/7, AAV11/8, AAV11/9, AAV11/10, chimeric virion or derivatives thereof. Gao et al., "Novel adeno-associated viruses from rhesus monkeys as vectors for human gene therapy," PNAS 99(18): 11854-11859, Sep. 3, 2002, is incorporated herein by reference for AAV vectors and chimeric virions useful as gene therapy vectors, and their construction and use.

In a more specific embodiment, the gene therapy vector is a chimeric AAV vector with a serotype 2 rep gene sequence and a serotype 8 cap sequence ("AAV2/8" or "AAV RC2/8").

In some embodiments, the gene therapy vector is a viral vector that has been pseudotyped (e.g., engineered) to target a specific cell, e.g., a hepatocyte. Many of the advances in targeted gene therapy using viral vectors may be summarized as non-recombinatorial (non-genetic) or recombinatorial (genetic) modification of the viral vector, which result in the pseudotyping, expanding, and/or retargeting of the natural tropism of the viral vector. (Reviewed in Nicklin and Baker (2002) *Curr. Gene Ther.* 2:273-93; Verheiji and Rottier (2012) *Advances Virol* 2012:1-15). Non-genetic approaches typically utilize an adaptor, which recognizes both a wildtype (non-modified) virus surface protein and a target cell. Soluble pseudo-receptors (for the wildtype virus), polymers such as polyethylene glycol, and antibodies or portions thereof, have been used as the virus binding domain of the adaptors, while natural peptide or vitamin ligands, and antibodies and portions thereof have been used for the cell binding domain of the adaptors described above. For example, retargeting of the viral vector to a target cell may be accomplished upon binding of the vector:adaptor complex to a protein expressed on the surface of the target cell, e.g., a cell surface protein. Such approach has been used for AAV (Bartlett et al. (1999) *Nat. Biotechnol.* 74: 2777-2785), adenoviruses (Hemminki et al. (2001) *Cancer Res.* 61: 6377-81; van Beusechem et al. (2003) *Gene Therapy* 10:1982-1991; Einfeld, et al. (2001) *J. Virol.* 75:11284-91; Glasgow et al. (2009) *PLOS One* 4:e8355), herpesviruses (Nakano et al. (2005) *Mol. Ther.* 11:617-24), and paramyxoviruses (Bian et al. (2005) *Cancer Gene Ther.* 12:295-303; Bian et al. (2005) *Int. J. Oncol.* 29:1359-69), Coronaviruses (Haijema et al. (2003) *J. Virol.* 77:4528-4538; Wurdinger et al. (2005) *Gene Therapy* 12:1394-1404).

A more popular approach has been the recombinatorial genetic modification of viral capsid proteins, and thus, the surface of the viral capsid. In indirect recombinatorial approaches, a viral capsid is modified with a heterologous "scaffold", which then links to an adaptor. The adaptor binds to the scaffold and the target cell. (Arnold et al. (2006) *Mol. Ther.* 5:125-132; Ponnazhagen et al. (2002) *J. Virol.* 76:12900-907; see also WO 97/05266) Scaffolds such as (1) Fc binding molecules (e.g., Fc receptors, Protein A, etc.), which bind to the Fc of antibody adaptors, (2) (strept)avidin, which binds to biotinylated adaptors, (3) biotin, which binds to adaptors fused with (strept)avidin, and (4) protein:protein binding pairs that form isometric peptide bonds such as SpyCatcher, which binds a SpyTagged adaptor, have been incorporated into Ad (Pereboeva et al. (2007) *Gene Therapy* 14: 627-637; Park et al. (2008) *Biochemical and Biophysical Research Communications* 366: 769-774; Henning et al. (2002) *Human Gene Therapy* 13:1427-1439; Banerjee et al. (2011) *Bioorganic and Medicinal Chemistry Letters* 21:4985-4988), AAV (Gigout et al. (2005) *Molecular Therapy* 11:856-865; Stachler et al. (2008) *Molecular Therapy* 16:1467-1473), and togavirus (Quetglas et al. (2010) *Virus Research* 153:179-196; Ohno et al. (1997) *Nature Biotechnology* 15:763-767; Klimstra et al. (2005) *Virology* 338:9-21).

In a direct recombinatorial targeting approach, a targeting ligand is directly inserted into, or coupled to, a viral capsid, i.e., protein viral capsids are modified to express a heterologous ligand. The ligand than redirects, e.g., binds, a receptor or marker preferentially or exclusively expressed on a target cell. (Stachler et al. (2006) *Gene Ther.* 13:926-931; White et al. (2004) *Circulation* 109:513-519.). Direct recombinatorial approaches have been used in AAV (Park et al., (2007) *Frontiers in Bioscience* 13:2653-59; Girod et al. (1999) *Nature Medicine* 5:1052-56; Grifman et al. (2001) *Molecular Therapy* 3:964-75; Shi et al. (2001) *Human Gene Therapy* 12:1697-1711; Shi and Bartlett (2003) *Molecular Therapy* 7:515-525), retrovirus (Dalba et al. *Current Gene Therapy* 5:655-667; Tai and Kasahara (2008) *Frontiers in Bioscience* 13:3083-3095; Russell and Cosset (1999) *Journal of Gene Medicine* 1:300-311; Erlwein et al. (2002) *Virology* 302:333-341; Chadwick et al. (1999) *Journal of Molecular Biology* 285:485-494; Pizzato et al. (2001) *Gene Therapy* 8:1088-1096), poxvirus (Guse et al. (2011) *Expert Opinion on Biological Therapy* 11:595-608; Galmiche et al. (1997) *Journal of General Virology* 78:3019-3027; Paul et al. (2007) *Viral Immunology* 20:664-671), paramyxovirus (Nakamura and Russell (2004) *Expert Opinion on Biological Therapy* 4:1685-1692; Hammond et al. (2001) *Journal of Virology* 75:2087-2096; Galanis (2010) *Clinical Pharmacology and Therapeutics* 88:620-625; Blechacz and Russell (2008) *Current Gene Therapy* 8:162-175; Russell and Peng (2009) *Current Topics in Microbiology and Immunology* 330:213-241), and herpesvirus (Shah and Breakefield (2006) *Current Gene Therapy* 6:361-370; Campadelli-Fiume et al. (2011) *Reviews in Medical Virology* 21:213-226).

In some embodiments, a gene therapy vector as described herein is pseudotyped to those tissues that are particularly suited for generating a regulatory response, e.g., tolerance toward, e.g., the replacement enzyme. Such tissues include, but are not limited to mucosal tissue, e.g., gut-associated lymphoid tissue (GALT), hematopoietic stem cells, and the liver. In some embodiments, the gene therapy vector, or gene encoding a multidomain therapeutic protein as described herein is expressed under the control of promoters specific for those tissues, e.g., a liver specific promoter.

In some embodiments, a gene therapy vector as described herein comprises a naked polynucleotide. For example, in some embodiments, a polynucleotide encoding a multidomain therapeutic polypeptide may be injected, e.g., intramuscularly, directly into an organ for the formation of a depot, intravenously, etc. Additional methods well-known for the enhanced delivery of naked polynucleotides include but are not limited to electroporation, sonoporation, use of a gene gun to shoot polynucleotides coated gold particles, magnetofection, and hydrodynamic delivery.

In some embodiments, a gene therapy vector as described herein comprises polynucleotide complexes, such as, but not limited to, nanoparticles (e.g., polynucleotide self-assembled nanoparticles, polymer-based self-assembled nanoparticles, inorganic nanoparticles, lipid nanoparticles, semiconductive/metallic nanoparticles), gels and hydrogels, polynucleotide complexes with cations and anions, microparticles, and any combination thereof.

In some embodiments, the polynucleotides disclosed herein may be formulated as self-assembled nanoparticles. As a non-limiting example, polynucleotides may be used to make nanoparticles which may be used in a delivery system for the polynucleotides (See e.g., International Pub. No. WO2012125987; herein incorporated by reference in its entirety). In some embodiments, the polynucleotide self-assembled nanoparticles may comprise a core of the polynucleotides disclosed herein and a polymer shell. The polymer shell may be any of the polymers described herein and are known in the art. In an additional embodiment, the polymer shell may be used to protect the polynucleotides in the core.

In some embodiment, these self-assembled nanoparticles may be microsponges formed of long polymers of polynucleotide hairpins which form into crystalline 'pleated' sheets before self-assembling into microsponges. These microsponges are densely-packed sponge like microparticles which may function as an efficient carrier and may be able to deliver cargo to a cell. The microsponges may be from 1 μm to 300 nm in diameter. The microsponges may be complexed with other agents known in the art to form larger microsponges. As a non-limiting example, the microsponge may be complexed with an agent to form an outer layer to promote cellular uptake such as polycation polyethyleneime (PEI). This complex can form a 250-nm diameter particle that can remain stable at high temperatures (150° C.) (Grabow and Jaegar, Nature Materials 2012, 11:269-269; herein incorporated by reference in its entirety). Additionally these microsponges may be able to exhibit an extraordinary degree of protection from degradation by ribonucleases. In another embodiment, the polymer-based self-assembled nanoparticles such as, but not limited to, microsponges, may be fully programmable nanoparticles. The geometry, size and stoichiometry of the nanoparticle may be precisely controlled to create the optimal nanoparticle for delivery of cargo such as, but not limited to, polynucleotides.

In some embodiments, polynucleotides may be formulated in inorganic nanoparticles (U.S. Pat. No. 8,257,745, herein incorporated by reference in its entirety). The inorganic nanoparticles may include, but are not limited to, clay substances that are water swellable. As a non-limiting example, the inorganic nanoparticle may include synthetic smectite clays which are made from simple silicates (See e.g., U.S. Pat. Nos. 5,585,108 and 8,257,745 each of which are herein incorporated by reference in their entirety).

In some embodiments, a polynucleotide may be formulated in water-dispersible nanoparticle comprising a semiconductive or metallic material (U.S. Pub. No. 20120228565; herein incorporated by reference in its entirety) or formed in a magnetic nanoparticle (U.S. Pub. No. 20120265001 and 20120283503; each of which is herein incorporated by reference in its entirety). The water-dispersible nanoparticles may be hydrophobic nanoparticles or hydrophilic nanoparticles.

In some embodiments, the polynucleotides disclosed herein may be encapsulated into any hydrogel known in the art which may form a gel when injected into a subject. Hydrogels are a network of polymer chains that are hydrophilic, and are sometimes found as a colloidal gel in which water is the dispersion medium. Hydrogels are highly absorbent (they can contain over 99% water) natural or synthetic polymers. Hydrogels also possess a degree of flexibility very similar to natural tissue, due to their significant water content. The hydrogel described herein may used to encapsulate lipid nanoparticles which are biocompatible, biodegradable and/or porous.

As a non-limiting example, the hydrogel may be an aptamer-functionalized hydrogel. The aptamer-functionalized hydrogel may be programmed to release one or more polynucleotides using polynucleotide hybridization. (Battig et al., J. Am. Chem. Society. 2012 134:12410-12413; herein incorporated by reference in its entirety). In some embodiment, the polynucleotide may be encapsulated in a lipid nanoparticle and then the lipid nanoparticle may be encapsulated into a hyrdogel.

In some embodiments, the polynucleotides disclosed herein may be encapsulated into a fibrin gel, fibrin hydrogel or fibrin glue. In another embodiment, the polynucleotides may be formulated in a lipid nanoparticle or a rapidly eliminated lipid nanoparticle prior to being encapsulated into a fibrin gel, fibrin hydrogel or a fibrin glue. In yet another embodiment, the polynucleotides may be formulated as a lipoplex prior to being encapsulated into a fibrin gel, hydrogel or a fibrin glue. Fibrin gels, hydrogels and glues comprise two components, a fibrinogen solution and a thrombin solution which is rich in calcium (See e.g., Spicer and Mikos, Journal of Controlled Release 2010. 148: 49-55; Kidd et al. Journal of Controlled Release 2012. 157:80-85; each of which is herein incorporated by reference in its entirety). The concentration of the components of the fibrin gel, hydrogel and/or glue can be altered to change the characteristics, the network mesh size, and/or the degradation characteristics of the gel, hydrogel and/or glue such as, but not limited to changing the release characteristics of the fibrin gel, hydrogel and/or glue. (See e.g., Spicer and Mikos, Journal of Controlled Release 2010. 148: 49-55; Kidd et al. Journal of Controlled Release 2012. 157:80-85; Catelas et al. Tissue Engineering 2008. 14:119-128; each of which is herein incorporated by reference in its entirety). This feature may be advantageous when used to deliver the polynucleotide disclosed herein. (See e.g., Kidd et al. Journal of Controlled Release 2012. 157:80-85; Catelas et al. Tissue Engineering 2008. 14:119-128; each of which is herein incorporated by reference in its entirety).

In some embodiments, a polynucleotide disclosed herein may include cations or anions. In one embodiment, the formulations include metal cations such as, but not limited to, Zn2+, Ca2+, Cu2+, Mg+ and combinations thereof. As a non-limiting example, formulations may include polymers and a polynucleotide complexed with a metal cation (See e.g., U.S. Pat. Nos. 6,265,389 and 6,555,525, each of which is herein incorporated by reference in its entirety).

In some embodiments, a polynucleotide may be formulated in nanoparticles and/or microparticles. These nanoparticles and/or microparticles may be molded into any size shape and chemistry. As an example, the nanoparticles and/or microparticles may be made using the PRINT® technology by LIQUIDA TECHNOLOGIES® (Morrisville, N.C.) (See e.g., International Pub. No. WO2007024323; herein incorporated by reference in its entirety).

In some embodiments, the polynucleotides disclosed herein may be formulated in NanoJackets and NanoLiposomes by Keystone Nano (State College, Pa.). NanoJackets are made of compounds that are naturally found in the body including calcium, phosphate and may also include a small amount of silicates. Nanojackets may range in size from 5 to 50 nm and may be used to deliver hydrophilic and hydrophobic compounds such as, but not limited to, polynucleotides, primary constructs and/or polynucleotide. NanoLiposomes are made of lipids such as, but not limited to, lipids which naturally occur in the body. NanoLiposomes may range in size from 60-80 nm and may be used to deliver hydrophilic and hydrophobic compounds such as, but not limited to, polynucleotides, primary constructs and/or polynucleotide. In one aspect, the polynucleotides disclosed herein are formulated in a NanoLiposome such as, but not limited to, Ceramide NanoLiposomes.

In one embodiment, the multidomain therapeutic protein is an anti-CD63 scFv-GAA fusion protein or an anti-ITGA7 scFv-GAA fusion protein. The administration of the anti-CD63 scFv-GAA fusion protein or the anti-ITGA7 scFv-GAA fusion protein via AAV-delivery provides long term stable production of GAA in the serum of the patient after administration of the multidomain therapeutic protein-harboring gene therapy vector. In one embodiment, the level of GAA in the serum of the recipient patient is ≥1.5 fold to 100 fold, ≥1.5 fold to 10 fold, ≥2.5 fold, 2.5 fold-3 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 3.6 fold, 3.7 fold, 3.8 fold, 3.9 fold, 4 fold, 5 fold, 6 fold, 7 fold, 8 fold, 9 fold, or 10 fold greater than the serum levels of a patient receiving GAA not linked to a delivery domain after 1 month, 3 months, 4 months, 5 months, or 6 months after administration of the multidomain therapeutic protein-harboring gene therapy vector.

In one embodiment, the administration of the anti-CD63 scFv-GAA fusion protein or the anti-ITGA7 scFv-GAA fusion protein via AAV-delivery provides long term stable reduction in stored glycogen levels in patients with Pompe disease. In one embodiment, the glycogen levels in heart, skeletal muscle, and liver tissue in the patient are reduced to wildtype (non-disease) levels. In one embodiment, the glycogen levels in heart, skeletal muscle, and liver tissue in the patient are maintained at wildtype levels 1 month, 2 months, 3 months, 4 months, 5 months, or 6 months after administration of the multidomain therapeutic protein-harboring gene therapy vector.

In one embodiment, the administration of the anti-CD63 scFv-GAA fusion protein or the anti-ITGA7 scFv-GAA fusion protein via AAV-delivery provides long term restoration of muscle strength in patients with Pompe disease. In one embodiment, the strength of the patient as measured by grip strength is restored to normal (i.e., non-disease normal levels) 1 month, 2 months, 3 months, 4 months, 5 months, or 6 months after administration of the multidomain therapeutic protein-harboring gene therapy vector.

In another aspect, the invention provides a composition comprising an enzyme activity and an antigen-binding protein, wherein the enzyme is associated with an enzyme-deficiency disease (LSD) and internalization effector-binding protein. Enzymes (which include proteins that are not per se catalytic) associated with lysosomal storage diseases include for example any and all hydrolases, α-galactosidase, β-galactosidase, α-glucosidase, β-glucosidase, saposin-C activator, ceramidase, sphingomyelinase, β-hexosaminidase, GM2 activator, GM3 synthase, arylsulfatase, sphingolipid activator, α-iduronidase, iduronidase-2-sulfatase, heparin N-sulfatase, N-acetyl-α-glucosaminidase, α-glucosamide N-acetyltransferase, N-acetylglucosamine-6-sulfatase, N-acetylgalactosamine-6-sulfate sulfatase, N-acetylgalactosamine-4-sulfatase, β-glucuronidase, hyaluronidase, and the like.

Internalization effector-binding proteins for example include a receptor-fusion molecule, a trap molecule, a receptor-Fc fusion molecule, an antibody, an Fab fragment, an F(ab')2 fragment, an Fd fragment, an Fv fragment, a single-chain Fv (scFv) molecule, a dAb fragment, an isolated complementarity determining region (CDR), a CDR3 peptide, a constrained FR3-CDR3-FR4 peptide, a domain-specific antibody, a single domain antibody, a domain-deleted antibody, a chimeric antibody, a CDR-grafted antibody, a diabody, a triabody, a tetrabody, a minibody, a nanobody, a monovalent nanobody, a bivalent nanobody, a small modular immunopharmaceutical (SMIP), a camelid antibody (VHH heavy chain homodimeric antibody), a shark variable IgNAR domain, other antigen-binding proteins, and the like.

Internalization effectors include for example CD63, MHC-I, Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), PRLR (prolactin receptor), MAL (Myelin And Lymphocyte protein, a.k.a. VIP17), IGF2R, vacuolar-type H+ ATPase, diphtheria toxin receptor, folate receptor, glutamate receptors, glutathione receptor, leptin receptor, scavenger receptor, SCARA1-5, SCARB1-3, and CD36. In certain embodiments, the internalization effector is a kidney specific internalizer, such as CDH16 (Cadheri-16), CLDN16 (Claudn-16), KL (Klotho), PTH1R (parathyroid hormone receptor), SLC22A13 (Solute carrier family 22 member 13), SLC5A2 (Sodium/glucose cotransporter 2), and UMOD (Uromodulin). In other certain embodiments, the internalization effector is a muscle specific internalizer, such as BMPR1A (Bone morphogenetic protein receptor 1A), m-cadherin, CD9, MuSK (muscle-specific kinase), LGR4/GPR48 (G protein-coupled receptor 48), cholinergic receptor (nicotinic) alpha 1, CDH15 (Cadheri-15), ITGA7 (Integrin alpha-7), CACNG1 (L-type calcium channel subunit gamma-1), CACNA1S (L-type calcium channel subunit alpha-15), CACNG6 (L-type calcium channel subunit gamma-6), SCN1B (Sodium channel subunit beta-1), CHRNA1 (ACh receptor subunit alpha), CHRND (ACh receptor subunit delta), LRRC14B (Leucine-rich repeat-containing protein 14B), dystroglycan (DAG1), and POPDC3 (Popeye domain-containing protein 3). In some specific embodiments, the internalization effector is ITGA7, CD9, CD63, ALPL2, ASGR1, ASGR2 or PRLR.

In some embodiments, the enzyme is covalently linked (i.e., electrons shared across atoms) to the antigen-binding protein. In one particular embodiment, the internalization effector-binding protein consists of or contains a half-body; the enzyme is fused to an Fc-fusion domain (e.g., at the C-terminus); and the Fc-domain that is covalently linked to the enzyme associates with the Fc-domain of the antigen-binding protein, such that the association contains one or more disulfide bridges. This particular embodiment is schematically depicted in FIG. 1A, panel B.

In another particular embodiment, the internalization effector-binding protein (delivery domain) consists of or contains an antibody or an antibody fragment, and the enzyme is covalently linked to the antibody or antibody fragment. In a specific embodiment, the delivery domain is an antibody, and the enzyme is covalently linked (directly through a peptide bond, or indirectly via a linker) to the C-terminus of the heavy chain or the light chain of the antibody (FIG. 1A, panels C or E, respectively). In another specific embodiment, the delivery domain is an antibody, and the enzyme is covalently linked (directly through a peptide bond, or indirectly via a linker) to the N-terminus of the heavy chain or the light chain of the antibody (FIG. 1A, panels D or F, respectively).

In some embodiments, the enzyme and delivery domain are not covalently linked, but are combined in an admixture. The delivery domain and the enzyme can associate through non-covalent forces to form a complex. For example, in one particular embodiment, the delivery domain is a bispecific antibody in which one arm of the antibody binds the internalization effector and the other arm binds the enzyme. This embodiment is schematically depicted in FIG. 1A, panel A.

In some embodiments, the enzyme is GAA or comprises GAA activity (e.g., an isozyme with GAA activity), and the internalization effector is ITGA7, CDH15, CD9, CD63, APLP2, ASGR1, ASGR2 or PRLR. In a particular embodiment, the enzyme is GAA or comprises GAA activity, the internalization domain is CD63, and the delivery domain is a bispecific antibody with specificity for CD63 and GAA. In a particular embodiment, the enzyme is GAA or comprises GAA activity, the internalization domain is ITGA7, and the delivery domain is a bispecific antibody with specificity for ITGA7 and GAA.

In some embodiments, the enzyme is GLA or comprises GLA activity (e.g., an isozyme with GAA activity), and the internalization effector is ITGA7, CD9, CD63, APLP2, ASGR1, ASGR2, or PRLR. In a particular embodiment, the enzyme is GLA or comprises GLA activity, the internalization domain is CD63, and the delivery domain is a bispecific antibody with specificity for CD63 and GLA. In a particular embodiment, the enzyme is GLA or comprises GLA activity, the internalization domain is ITGA7, and the delivery domain is a bispecific antibody with specificity for ITGA7 and GLA.

Pharmaceutical Compositions and Administration Thereof

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21.sup.st Edition, A. R. Gennaro (Lippincott, Williams & Wilkins, Baltimore, Md., 2006; incorporated herein by reference in its entirety) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN® 20], polyoxyethylene sorbitan [TWEEN® 60], polyoxyethylene sorbitan monooleate [TWEEN® 80], sorbitan monopalmitate [SPAN® 40], sorbitan monostearate [SPAN® 60], sorbitan tristearate [SPAN® 65], glyceryl monooleate, sorbitan monooleate [SPAN® 80]), polyoxyethylene esters (e.g. polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ® 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC® F 68, POLOXAMER® 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfate, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN® II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof Excipients such as cocoa butter and suppository waxes, coloring agents, coating agents, sweetening, flavoring, and/or perfuming agents can be present in the composition, according to the judgment of the formulator.

Delivery

The present disclosure encompasses the delivery of the gene therapy vector (e.g., the polynucleotides) by any appropriate route taking into consideration likely advances in the sciences of drug delivery. Delivery may be naked or formulated.

Naked Delivery

The polynucleotides of the present invention may be delivered to a cell naked. As used herein in, "naked" refers to delivering polynucleotides free from agents which promote transfection. For example, the polynucleotides delivered to the cell may contain no modifications. The naked polynucleotides may be delivered to the cell using routes of administration known in the art and described herein.

Formulated Delivery

The polynucleotides may be formulated, using the methods described herein. The formulations may contain polynucleotides and may further include, but are not limited to, cell penetration agents, a pharmaceutically acceptable carrier, a delivery agent, a bioerodible or biocompatible polymer, a solvent, and a sustained-release delivery depot. The formulated polynucleotides mRNA may be delivered to the cell using routes of administration known in the art and described herein.

Administration

The polynucleotides of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them cross the blood-brain barrier, vascular barrier, or other epithelial barrier. Non-limiting routes of administration for the polynucleotides, primary constructs or mRNA of the present invention are described below.

Parenteral and Injectible Administration

Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Depot Administration

As described herein, in some embodiments, the composition is formulated in depots for extended release. Generally, a specific organ or tissue (a "target tissue") is targeted for administration.

In some aspects of the invention, the polynucleotides are spatially retained within or proximal to a target tissue. Provided are method of providing a composition to a target tissue of a mammalian subject by contacting the target tissue (which contains one or more target cells) with the composition under conditions such that the composition, in particular the nucleic acid component(s) of the composition, is substantially retained in the target tissue, meaning that at least 10, 20, 30, 40, 50, 60, 70, 80, 85, 90, 95, 96, 97, 98, 99, 99.9, 99.99 or greater than 99.99% of the composition is retained in the target tissue. Advantageously, retention is determined by measuring the amount of the nucleic acid present in the composition that enters one or more target cells. For example, at least 1, 5, 10, 20, 30, 40, 50, 60, 70, 80, 85, 90, 95, 96, 97, 98, 99, 99.9, 99.99 or greater than 99.99% of the nucleic acids administered to the subject are present intracellularly at a period of time following administration. For example, intramuscular injection to a mammalian subject is performed using an aqueous composition containing a polynucleotide and a transfection reagent, and retention of the composition is determined by measuring the amount of the ribonucleic acid present in the muscle cells.

Aspects of the invention are directed to methods of providing a composition to a target tissue of a mammalian subject, by contacting the target tissue (containing one or more target cells) with the composition under conditions such that the composition is substantially retained in the target tissue. The composition contains an effective amount of a polynucleotide such that the polypeptide of interest is produced in at least one target cell. The compositions generally contain a cell penetration agent, although "naked" nucleic acid (such as nucleic acids without a cell penetration agent or other agent) is also contemplated, and a pharmaceutically acceptable carrier.

In some circumstances, the amount of a protein produced by cells in a tissue is desirably increased. Preferably, this increase in protein production is spatially restricted to cells within the target tissue. Thus, provided are methods of increasing production of a protein of interest in a tissue of a mammalian subject. A composition is provided that contains polynucleotides characterized in that a unit quantity of composition has been determined to produce the polypeptide of interest in a substantial percentage of cells contained within a predetermined volume of the target tissue.

In some embodiments, the composition includes a plurality of different polynucleotides, where one or more than one of the polynucleotides encodes a polypeptide of interest. Optionally, the composition also contains a cell penetration agent to assist in the intracellular delivery of the composition. A determination is made of the dose of the composition required to produce the polypeptide of interest in a substantial percentage of cells contained within the predetermined volume of the target tissue (generally, without inducing significant production of the polypeptide of interest in tissue adjacent to the predetermined volume, or distally to the target tissue). Subsequent to this determination, the determined dose is introduced directly into the tissue of the mammalian subject.

In one embodiment, the invention provides for the polynucleotides to be delivered in more than one injection or by split dose injections.

In one embodiment, the invention may be retained near target tissue using a small disposable drug reservoir, patch pump or osmotic pump. Non-limiting examples of patch pumps include those manufactured and/or sold by BD® (Franklin Lakes, N.J.), Insulet Corporation (Bedford, Mass.), SteadyMed Therapeutics (San Francisco, Calif.), Medtronic (Minneapolis, Minn.) (e.g., MiniMed), UniLife (York, Pa.), Valeritas (Bridgewater, N.J.), and SpringLeaf Therapeutics (Boston, Mass.). A non-limiting example of an osmotic pump include those manufactured by DURECT® (Cupertino, Calif.) (e.g., DUROS® and ALZET®).

Dosing

The present invention provides methods comprising administering a gene therapy vector comprising polynucleotide encoding a multidomain therapeutic polypeptide, and optionally subsequently the multidomain therapeutic polypeptide to a subject in need thereof. In some embodiments, a method comprises administering a gene therapy vector comprising polynucleotide encoding a multidomain therapeutic polypeptide in a therapeutically effective amount to a patient in need thereof, wherein the therapeutically effective amount is sufficient to obviate the subsequent administration of the multidomain therapeutic polypeptide. Accordingly, in some embodiments, a method of treating a patient in need thereof lacking an enzyme, e.g., reducing glycogen levels and/or reducing CRIM to GAA in a patient with Pompe disease, comprises administering to the patient a gene therapy vector comprising a polynucleotide encoding a multidomain therapeutic protein comprising the replacement enzyme, e.g., an anti-CD63 scFv::GAA fusion protein, e.g., a multidomain therapeutic protein comprising the sequence set forth as SEQ ID NO:11, in a therapeutically effective amount, wherein the therapeutically effective amount negates the need for subsequent administration to the patient of the replacement enzyme, e.g., GAA or derivatives thereof. In some embodiments, a method of treating a patient lacking an enzyme and in need thereof, e.g., reducing glycogen levels and/or reducing CRIM to GAA in a patient with Pompe disease, comprises administering to the patient a gene therapy vector comprising a polynucleotide encoding a multidomain therapeutic protein comprising a replacement enzyme, e.g., an anti-CD63 scFv::GAA fusion protein, e.g., a multidomain therapeutic protein comprising the sequence set forth as SEQ ID NO:11, in a therapeutically effective amount, and further comprises administering to the patient a therapeutically effective amount of the replacement enzyme. Nucleic acids, proteins or complexes, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The following examples are provided to further illustrate the methods of the present invention. These examples are illustrative only and are not intended to limit the scope of the invention in any way.

EXAMPLES

Example 1: Construction of Anti-hCD63 ScFv::GAA Polynucleotide and Gene Therapy Vector AAV2/8 viruses encoding for the expression of human GAA (hGAA; SEQ ID NO: 1; nucleic acid sequence represented by SEQ ID NO:12) or an anti-human CD63 single chain variable fragment (ScFv) fused on its C-terminus to human GAA (anti-hCD63 ScFv-hGAA; SEQ ID NO: 10; nucleic acid represented by SEQ ID NO:11) were generated using a standard triple transfection protocol (Gray et al. 2011; see also "Production of recombinant adeno-associated viral vectors and use in vitro and in vivo administration", Current Protocols in Neuroscience, John Wiley & Sons, New York (1999), pp. 4.17.1-4.17.25, Vol 1). For the production, 1×10$^7$ HEK293 cells were plated onto 15 cm plates. The following day the cells were transfected with (A) either 8 µg of a control pAAV vector comprising a liver specific serpina 1 enhancer (SEQ ID NO:9) and encoding TTR driven human GAA or test pAAV comprising a liver specific serpina 1 enhancer (SEQ ID NO:9) and encoding a TTR driven hCD63 ScFv-hGAA (see FIG. 1B) and (B) pAAV RC2/8-derived vector (Gao, 2002) and 16 µg of pHelper (Agilent, Cat #240074) using PEIpro (Polyplus transfection, New York, N.Y. catalog#115-100)-mediated transfection at ratio of 1:1 (1 ul PEIpro: DNA). Seventy-two hours after transfection, the cells were collected and lysed in a buffer comprised of 20 mM Tris-HCl, 1 mM MgCl2, 2.5 mM KCl, 100 mM NaCl using a standard freeze-thaw method. Next, benzonase (Sigma, Cat# E1014-25KU) was added to the samples at a final concentration of 0.5 U/µL, and this was then incubated at 37° C. for 60 minutes. Viruses were then purified using iodixanol gradient ultracentrifugation as described in (Zolotukhin et al., 1999, Gene Ther 1999; 6:973-985) and were subsequently titrated by qPCR.

AAV samples were treated with DNaseI (Thermofisher Scientific, Cat #EN0525) at 37° C. for one hour and lysed using DNA extract All Reagents (Thermofisher Scientific Cat#4403319). Encapsidated viral genomes were quantified using an QuantStudio 3 Real-Time PCR System (Thermofisher Scientific) using primers directed to the AAV2 ITRs. The sequences of the AAV2 ITRs primers are 5'-GGAACCCCTAGTGATGGAGTT-3' (fwd ITR; SEQ ID NO:3) and 5'-CGGCCTCAGTGAGCGA-3' (rev ITR; SEQ ID NO:4) (Aurnhammer et al., 2012), derived the left internal inverted repeat (ITR) sequence from of the AAV (SEQ ID NO:6) and the right internal inverted repeat (ITR) sequence from of the AAV (SEQ ID NO:7), respectively. The sequence of the AAV2 ITRs probe is 5'-6-FAM-CACTCCCTCTCTGCGCGCTCG-TAMRA-3' (SEQ ID NO:5) (Aurnhammer C., Haase M., Muether N., et al., 2012, Hum. Gene Ther. Methods 23, 18-28). After a 95° C. activation step for 10 min, a two-step PCR cycle was performed at 95° C. for 15 seconds and 60° C. for 30 seconds for 40 cycles. The TaqMan Universal PCR Master Mix (Thermofisher Scientific, Cat #4304437) was used in the qPCR. DNA plasmid (Agilent, Cat #240074) was used as standard to determine absolute titers.

Anti-human CD63 antibodies and their fusions used the H5C6 mouse anti-human CD63 variable domains (amino acids 1-119 of SEQ ID NO:10 provide the amino acid sequence of the heavy chain variable domain ($V_H$) of the H5C6 antibody and amino acids 135-245 of SEQ ID NO:10 provide the amino acid sequence of the light chain variable domain ($V_L$) of the H5C6 antibody). The anti-hCD63 ScFv used here (SEQ ID NO:2) was derived from the H5C6 clone, which is mouse-anti-hCD63 monoclonal IgG1, kappa light chain antibody (H5C6 was deposited to the Developmental Studies Hybridoma Bank at the University of Iowa by August, J. T./Hildreth, J. E. K. (DSHB Hybridoma Product H5C6; DSHB Cat# h5c6, RRID:AB_528158). ScFv versions of the antibodies were cloned with variable domains in heavy-light order with a glycine-serine linker in between (5'-VH-Gly-Ser-VL-3')

Example 2: Glycogen Content in Murine Pompe Model Post-AAV

To determine the effect of AAV delivered anti-hCD63 ScFv-GAA fusion versus AAV delivered GAA, in a relevant glycogen storage in vivo model, both therapies were delivered to a Pompe disease mouse model where mice were homozygous for the deletion of the mouse GAA gene and were homozygous for the expression of human CD63 in place of mouse CD63 with a strain background of 75% C57BL/6; 25% 129SvJ. These mice are herein referred to as CD63 HumIn GAA KO mice or alternatively as CD63hu/hu; GAA$^{-/-}$ mice.

For the experiment, 2-month-old CD63 HumIn GAA KO mice were administered via tail vein injection with either AAV2/8 virus containing a genome with either the TTR liver specific promoter driving human GAA (AAV-hGAA; described in Example 1) or the TTR liver specific promoter driving anti-human CD63 ScFv fused at its C-terminus with human GAA (AAV-anti-hCD63 ScFv-hGAA; described in Example 1). Both AAV2/8 viruses were delivered at either one of two doses, 1e10 vg/mouse or 1e11 vg/mouse. As controls, untreated CD63 HumIn GAA KO mice and untreated CD63 HumIn with the mouse GAA gene intact were included in the assay. Mice were housed for 3 months after treatment and bled incrementally (monthly) during this period for serum measurements of GAA levels and anti-GAA antibodies. After 3 months, all mice were sacrificed and individual tissues were harvested for glycogen measurements, PAS-H staining, quantification of central nuclei, measurement of lysosomal proliferation, and measurement of LC3b expression. Experimental dosing and treatment protocol for groups of mice are shown in Table 4.

TABLE 4

Experimental dosing and treatment protocol for groups of mice

| Group | Mice | Number of Mice | Treatment | Dosage |
| --- | --- | --- | --- | --- |
| 1 | CD63 HumIn GAA KO | 4 | None | N/A |
| 2 | CD63 HumIn GAA KO | 4 | AAV-hGAA | 1e10 vg/mouse |
| 3 | CD63 HumIn GAA KO | 4 | AAV-hGAA | 1e11 vg/mouse |
| 4 | CD63 HumIn GAA KO | 5 | AAV-anti-hCD63 ScFv-hGAA | 1e10 vg/mouse |
| 5 | CD63 HumIn GAA KO | 4 | AAV-anti-hCD63 ScFv-hGAA | 1e11 vg/mouse |
| 6 | CD63 HumIn GAA WT | 2 | None | N/A |

The results are also depicted in FIG. 2, which shows that anti-hCD63scFv::GAA brings glycogen down to wildtype levels in skeletal muscle, unlike GAA alone. Treatment with the two-domain anti-hCD63scFv::GAA multidomain therapeutic protein resulted in much greater reduction in stored glycogen compared to the single-domain GAA replacement enzyme. By plotting quadriceps glycogen levels (FIG. 3) or heart glycogen levels (FIG. 4) against the total serum expression of GAA or scfv-GAA over three months for individual mice, it was observed that the anti-hCD63scFv::GAA fusion protein removes more glycogen than the GAA enzyme alone, even at similar serum levels (FIGS. 3 and 4).

Example 3: Immunological Response to GAA

To measure anti-human GAA antibody serum levels, serum from all the treatment groups was separated from the blood collected during the terminal bleed using serum separator tubes (BD Biosciences, Cat#365967) as per the manufacturer's specifications. Separately, 96-well high protein binding plates (ThermoFisher, Cat#15041) were coated with 20 μg of hGAA (R&D Systems, Cat#8329-GH-025) diluted in PBS overnight. Plates were washed with PBS+ 0.05% Tween (PBS-T) 3 times. Plates were blocked with 0.5% BSA in PBS-T, and serial dilutions of mouse serum ranging from 1:300 to 1:5.1e7 were added to the plate overnight. Total anti-mouse IgG (subclasses 1+2a+2b+3) was measured using a HRP conjugated goat anti-mouse IgG antibody (Jackson Immuno Research, Cat#115-035-164) and the BD Opt EIA substrate kit. The colormetric reactions were stopped using 1 N phosphoric acid. Absorbance was then read at 450 nm on a Spectramax i3 plate reader (Molecular Devices). Dilution curves were fit to sigmoidal curves, and titers were calculated from the curves. The titers expressed as mean total IgG titer+/−SD are shown in Table 5.

As shown in Table 5, mice that did not receive treatment showed an average background titer with mean levels of 1.1E+03. Mice treated with the low dose of virus (1e10 vg/mouse) of either AAV-anti-hCD63 ScFv-hGAA or AAV-hGAA demonstrated high titers, whereas in mice treated with the high dose (1e11 vg/mouse), titers were lower. Mice treated with 1e11 vg of AAV-anti-hCD63 ScFv-hGAA that had the highest levels of GAA in serum had titers within the range of untreated mice.

Higher levels of GAA or anti-hCD63scFv::GAA after AAV administration correspond with lower anti-GAA titers. The serum of GAA null mice treated with high or low titers of AAV-anti-hCD63scFv::GAA or AAV-GAA were assessed for anti-GAA antibodies over the course of the three months post-injection. FIG. 5 depicts serum anti-GAA antibody titers vs GAA exposure (i.e., the total serum expression over 3 months of GAA or scfv-GAA) for individual mice, which demonstrates a negative correlation between antibody titer and serum exposure to GAA, demonstrating that mice with high GAA exposure were tolerized to GAA. Likewise, FIG. 6, which plots anti-GAA antibody titers for various groups infected with AAV encoding GAA or an anti-hCD63scFv::GAA protein, demonstrates that higher doses of construct led to lower titers of anti-GAAs.

Example 4: Serum GAA

To measure human GAA serum levels over the course of the experiment, samples were collected at monthly time points via tail bleed. Serum was separated from the blood using serum separator tubes (BD Biosciences, Cat#365967) as per the manufacturer's specifications. 1 μL of isolated serum was then loaded onto a 4-20% Novex wedgewell pre-cast gel, run at 220V for 45 minutes and transferred to nitrocellulose membrane at 200 mA for 1 hour using standard procedures. The nitrocellulose membrane was then probed with an anti-GAA primary antibody (Abcam, #ab137068) used at a dilution of 1:2000 and an anti-GAPDH antibody (Abcam, #AB9484) used at a dilution of 1:1000 in 12 mL and incubated overnight at 4° C. After primary antibody incubation, the membrane was washed three times with 1×TBST for 5 minutes per wash. Anti-rabbit IgG (LiCor, 926-32211) and anti-mouse IgG (LiCor, 925-68070) (LiCor, Lincoln, Nebr.) secondary antibodies at a dilution of 1:15000 in 12 mL were then added to the membrane and incubated for 1 hour at room temperature. After secondary antibody incubation, the membrane was washed two times with 1×TBST for 5 minutes per wash and one time with 1×TBS for 5 minutes. The membrane was then imaged and quantified using a LiCor Odyssey instrument (LI-COR Biotechnology). Serum levels of GAA expressed as mean+/− standard deviation (SD) in arbitrary units are shown in Table 6.

As shown in Table 6, CD63 HumIn GAA KO mice treated with the high dose (10¹¹ vg/mouse) of AAV-anti-hCD63 ScFv-hGAA or AAV-hGAA tested demonstrated sustained levels of GAA in the serum over the course of the experiment, with serum levels of GAA somewhat higher in AAV-

TABLE 5

Serum anti-GAA antibody levels

| | Total IgG anti-GAA titer CD63 HumIn GAA KO + no treatment | CD63 HumIn GAAKO + AAV-hGAA (1e10vg) | CD63 HumIn GAA KO + AAV-hGAA (1e11vg) | CD63 HumIn GAA KO + AAV-anti-hCD63 ScFv-hGAA (1e10vg) | CD63 HumIn GAA KO + AAV-anti-hCD63 ScFv-hGAA (1e11vg) |
|---|---|---|---|---|---|
| Mean | 1.1E+03 | 7.6E+06 | 2.4E+04 | 5.5E+04 | 4.0E+03 |
| SD | 1.3E+03 | 1.0E+07 | 2.5E+04 | 1.9E+04 | 4.9E+03 | anti-hCD63 ScFv-hGAA treated mice than in the AAV-hGAA treated mice. In mice treated with the treated with the low dose ($10^{10}$ vg/mouse) of either AAV-anti-hCD63 ScFv-hGAA or AAV-hGAA, the levels of GAA dropped over the course of the experiment, approaching negligible levels in some mice by the 12 week time point.

TABLE 6

Serum GAA levels

| Week | AAV-anti-hCD63 ScFv-hGAA ($10^{10}$vg) | | AAV-hGAA ($10^{10}$vg) | | AAV-anti-hCD63 ScFv-hGAA ($10^{11}$vg) | | AAV-hGAA ($10^{11}$vg) | |
|---|---|---|---|---|---|---|---|---|
|  | Mean | SD | Mean | SD | Mean | SD | Mean | SD |
| 1 | 0.21 | 0.17 | 0.04 | 0.03 | 2.36 | 1.78 | 0.77 | 0.53 |
| 2 | 0.19 | 0.16 | 0.07 | 0.07 | 2.02 | 1.18 | 1.15 | 0.56 |
| 4 | 0.17 | 0.15 | 0.01 | 0.02 | 2.80 | 1.16 | 1.22 | 0.75 |
| 8 | 0.29 | 0.33 | 0.03 | 0.05 | 2.58 | 1.18 | 0.62 | 0.60 |
| 12 | 0.12 | 0.19 | 0.00 | 0.01 | 2.61 | 1.53 | 0.77 | 0.86 |
| Area under the curve | 2.27 | 2.23 | 0.27 | 0.36 | 28.13 | 13.73 | 9.80 | 7.22 |

Expression of GAA or anti-hCD63scfv::GAA was maintained over time in mice receiving the high dose of AAV ($10^{11}$ vg/mouse), but fell off in mice receiving the lower dose ($10^{10}$ vg/mouse). FIG. 7A depicts a graph plotting serum levels of GAA, as probed by western blot, over time for various groups infected with AAV encoding GAA or an anti-hCD63 scfv fusion to GAA. The fusion protein (scFv::GAA) demonstrated consistently higher levels (e.g., 2.5 to 3-fold) of serum GAA than the GAA enzyme without the delivery domain (FIG. 7A).

Real-time PCR quantifications of expression in liver, heart, and quadriceps lysates 3 months after injection are shown in FIG. 7B. Liver expression was detected for all injections of AAV construct, with highest levels for the 1e11 vg/mouse injections for both AAV-hGAA and AAV-anti-hCD63::hGAA (both driven by liver-specific promoter, LSP). A comparison of serum GAA level to RNA expression level of GAA was also made (FIG. 7C) and the results show that mice receiving the AAV encoding the fusion protein presented lower GAA RNA expression localized to the liver at 3 months however GAA serum levels were high in that particular mouse. AAV-LSP-hGAA injections did not present high serum levels of GAA when RNA levels were low in the liver. See FIG. 7C. This data suggests that the AAV encoding the fusion protein (and expression is driven by a liver-specific promoter) attains an improved secretion profile for GAA.

A higher secreted to intracellular ratio of antibody::hGAA versus hGAA alone in Huh-7 hepatocytes was also observed. In one experiment, Huh-7 human hepatocytes were transiently transfected with liver-specific promoter driven constructs encoding for hGAA, anti-hCD63 scFv::GAA fusion, or a non-binding scFv::GAA fusion control. Both scFv::GAA fusion constructs had a higher ratio of protein in the secreted supernatant than hGAA alone 3 days after transfection (statistically significant to p<0.05, n=3). Addition of M6P into the supernatant during the experimental period to mitigate CI-MPR-mediated uptake did not affect the ratio.

Example 5: Tissue Measurement of Glycogen and Histological Characterization of Muscle Tissue Tissue Measurements of Glycogen:

To measure the glycogen content in individual tissues, heart, quadriceps, gastrocnemius, diaphragm, soleus, and EDL tissue were dissected from mice from all groups immediately after $CO_2$ asphyxiation, and were then snap frozen in liquid nitrogen, and stored at −80° C.~50 mg of each tissue was lysed on a benchtop homogenizer with stainless steel beads in distilled water at a ratio of 1 mg to 25 µL water for glycogen measurements. Glycogen analysis lysates were heated at 105° for 15 minutes and centrifuged at 21000×g to clear debris. Glycogen measurements were performed using a Glycogen Assay Kit (Sigma-Aldrich, #MAK016) according to manufacturer's instructions for fluorometric assays. The fluorescence of each sample was measured at 535 nm excitation and 587 nm emission on a fluorescence plate reader (Molecular Devices, Spectramax i3). The calculated amount of glycogen was calculated using the following formula provided by the manufacturer. The calculated amount of glycogen from each tissue in each treatment group was then averaged and is expressed as mean+/−standard deviation (SD) in Table 7.

As shown in Table 7, loss of Gaa causes a large increase in mean glycogen levels across all tissues measured, as compared to GAA WT mice. Treatment with AAV-anti-hCD63 ScFv-hGAA at $10^{11}$ vg/mouse reduced glycogen to WT- or near-WT levels in all tissues tested, unlike treatment with AAV-GAA which only partially reduced stored glycogen. The low doses of either virus also reduced glycogen, but to a lesser extent that the high doses. The $10^{10}$ vg/mouse dose of AAV-anti-hCD63 ScFv-hGAA reduced glycogen levels in a similar manner as the $10^{11}$ vg/mouse dose of AAV-GAA.

TABLE 7

Mean +/− SD glycogen level measured in heart, quadriceps, gastrocnemius, diaphragm, soleus, and EDL

|  | no treatment | | AAV-hGAA ($10^{10}$ vg) | | AAV-hGAA ($10^{11}$ vg) | |
|---|---|---|---|---|---|---|
|  | Mean | SD | Mean | SD | Mean | SD |
| Heart | 27.798 | 3.013 | 17.246 | 4.375 | 1.770 | 2.279 |
| Quadricep | 14.650 | 1.783 | 11.012 | 0.528 | 5.878 | 3.504 |
| Gastrocnemius | 14.295 | 0.480 | 10.990 | 0.868 | 6.073 | 3.080 |
| Diaphragm | 15.463 | 1.173 | 11.446 | 1.237 | 3.995 | 3.395 |
| Soleus | 17.260 | 2.262 | 13.684 | 2.506 | 6.533 | 5.201 |
| EDL | 13.588 | 0.498 | 11.178 | 1.760 | 6.275 | 3.159 |

|  | AAV-anti-hCD63 ScFv-hGAA ($10^{10}$ vg) | | AAV-anti-hCD63 ScFv-hGAA ($10^{11}$ vg) | | CD63 HumIn GAA WT mice (control) | |
|---|---|---|---|---|---|---|
|  | Mean | SD | Mean | SD | Mean | SD |
| Heart | 2.190 | 2.678 | 0.058 | 0.010 | 0.085 | 0.007 |
| Quadricep | 4.485 | 3.147 | 0.798 | 0.251 | 0.440 | 0.042 |
| Gastrocnemius | 5.198 | 2.516 | 0.825 | 0.461 | 0.790 | 0.014 |
| Diaphragm | 3.083 | 2.968 | 0.388 | 0.121 | 0.385 | 0.007 |
| Soleus | 5.268 | 2.786 | 1.040 | 0.896 | 0.545 | 0.049 |
| EDL | 2.495 | 1.750 | 0.313 | 0.099 | 0.260 | 0.141 |

Quadricep Harvest for Histopathology and Quantification:

Quadricep tissue samples from mice from each group besides the low dose (1e10 vg/mouse) treatment group were either snap frozen immediately after dissection in liquid nitrogen and stored at −80° C. for quantification of LC3b expression or were placed onto blocks containing O.C.T medium (Tissue-Tek, #4583).

Tissues samples in O.C.T medium were sent to Histoserv, Inc (Germantown, Md.) for sectioning and periodic acid Schiff (PAS) staining to detect polysaccharides. Additional sections were prepared and returned for staining of central nuclei and lysosomal proliferation.

Pas Staining:

PAS stain sections were imaged using a Leica slide scanner at 20× magnification. The resulting images from representative mice for each treatment group are shown in FIG. 8.

As shown in FIG. 8, CD63 HumIn GAA KO that were treated with AAV-anti-hCD63 ScFv-hGAA at 3 months demonstrated a marked decrease in staining as compared to both the CD63 HumIn GAA KO mice with no treatment and the CD63 HumIn GAA KO mice treated with AAV-hGAA, which displayed high levels of PAS staining. This further indicates that the treatment with AAV-anti-hCD63 ScFv-hGAA can reduce polysaccharides accumulation in CD63 HumIn GAA KO mice, and can do so in a uniform manner across muscle fibers.

Quantification of Central Nuclei and Lysosomal Proliferation:

Unstained sections from Histosery were removed from the freezer and then fixed with 4% paraformaldehyde in PBS for 15 minutes in a staining chamber. The fixed slides were then washed twice for 5 minutes in PBS and subsequently incubated with blocking buffer (eBiosciences, 00-4953-54) for 1 hour at room temperature. Slides were then either stained with either a rat anti-Lamp-1 antibody (Abcam, #AB25245) at a dilution of 1:50 in blocking buffer, a rabbit anti-Laminin antibody (Sigma, #L9393) at a dilution of 1:1000 in blocking buffer, or blocking buffer with no added antibody while in a humidified staining chamber and then transferred to 4° C. for overnight incubation. The following day, slides were then washed twice for 5 minutes in PBS and subsequently stained with either goat anti-rabbit IgG (H+L) superclonal secondary antibody conjugated with Alexa Fluor 647 (Life Tech Thermo, #A27040) or goat anti-rat IgG (H+L) cross-adsorbed secondary antibody conjugated with Alexa Fluor 555 (Life Tech Thermo, #A21434) in a staining chamber then allowed to incubate for 1 hour at room temperature. Stained slides were then washed twice for 5 minutes in PBS before they were mounted with Fluoromount-G with DAPI (Life Tech Thermo, #00-4959-52) and imaged on a Zeiss LSM710 instrument (Carl Zeiss Microscopy GmbH). Number of centralized nuclei was quantified using Halo software (Indica Labs, NM) and is expressed as percentage of fibers showing central nuclei+/−standard deviation are shown in Table 8. Lysosomal proliferation is depicted in FIG. 8.

TABLE 8

Quantification of central nuclei

| | no treatment | | AAV-hGAA (1e11vg) | | AAV-anti-hCD63 ScFv-hGAA (1e11vg) | | CD63 HumIn GAA WT mice control | |
|---|---|---|---|---|---|---|---|---|
| | Mean | SD | Mean | SD | Mean | SD | Mean | SD |
| % of Fiber with central nuclei | 22.00 | 10.10 | 33.00 | 4.36 | 12.75 | 6.29 | 8.50 | 7.78 |

Quantification of LC3b Expression:

For quantification of LC3b expression, snap frozen samples were thawed, homogenized and then lysed in RIPA buffer at a 1 mg tissue to 254, RIPA buffer ratio (150 mM NaCl, 1.0% IGEPAL® CA-630, 0.5% sodium deoxycholate, 0.1% SDS, 50 mM Tris, pH 8.0, Sigma Aldrich, R0278) by bead impaction for 45 seconds (MP Biomedical). Lysates were cleared of insoluble material by centrifugation at 21,000×g and then 300 μg of lysate in RIPA buffer was loaded on a 4-20% Novex wedgewell pre-cast gel, transferred to a nitrocellulose membrane and analyzed by western blot using a similar protocol as previously described for the analysis of serum GAA levels, substituting the use of primary antibody that recognizes mouse LC3b-I and LC3b-II (Sigma, #L7543) in place of the primary antibody against GAA. The membrane was then imaged and quantified using a LiCor Odyssey instrument (LI-COR Biotechnology). LC3b-I and LC3b-II levels expressed as (mean+/−standard deviation) in arbitrary units are shown in Table 9.

As shown in Table 9, there was a significant increase in both mean LC3b-I and LC3b-II levels in mice lacking GAA as compared to CD63 HumIn GAA WT mice. Treatment with AAV-anti-hCD63 ScFv-hGAA decreased mean LC3b-I and LC3b-II levels in CD63 HumIn GAA KO to the WT- or near-WT levels. CD63 HumIn GAA KO treated with AAV-hGAA demonstrated slightly decreased mean LC3b-I and LC3b-II levels as compared to CD63 HumIn GAA KO mice, but this decrease was not as pronounced as with AAV-anti-hCD63 ScFv-hGAA treatment.

TABLE 9

LC3b-I and LC3b-II levels in the quadriceps of mice

| treatment | untreated | AAV-hGAA | AAV-anti-hCD63 ScFv-hGAA | CD63 HumIn GAA WT (control) |
|---|---|---|---|---|
| LC3b-I levels (arbitrary units) | | | | |
| average | 833 | 628 | 403 | 282 |
| SD | 109 | 139 | 33 | 49 |
| LC3b-II levels (arbitrary units) | | | | |
| average | 3308 | 2888 | 445 | 369 |
| SD | 582 | 1282 | 398 | 33 |

Example 6: AAV Anti-hCD63::GAA Treatment Leads to Significant Gains in Tests of Muscle Strength and Coordination Grip strength and Rotarod test performance of mice treated (see above) with either AAV-LSP hGAA or AAV-LSP anti-hCD63::hGAA. Accelerating Rotarod measurements (FIG. 9A) and forelimb grip strength measurements (FIG. 9B) of wild-type GAA mice, untreated control, AAV-LSP-hGAA (1e11 vg/mouse) or AAV-LSP-anti-hCD63:: hGAA treatment (1e11 vg/mouse) were taken at monthly intervals for 6 months. Error bars are +/−SD. N=8-10 for all groups.

Example 7: Other Membrane Proteins as "Guides" Directing GAA to Tissues

Other membrane proteins were tested, such as anti-ITGA7 (Integrin alpha-7) fusion proteins, to guide GAA to tissues to replace GAA in enzyme-deficient mice. C2C12 mouse myoblasts were incubated overnight with anti-mCD63-GAA or anti-ITGA7-GAA with or without the presence of 5 mM M6P. Active GAA enzyme was detected in myoblast lysates over time for both fusion proteins (FIG. 10A). In further experiments, GAA KO mice humanized for CD63 (GAA−/−; CD63hu/hu) were given plasmids encoding an scFv::GAA format of anti-hCD63::GAA or a full-length IgG4::GAA format of anti-integrin alpha-7 by hydrodynamic delivery (HDD), and mice were sacrificed 3 weeks post-HDD. Tissue glycogen levels were measured in heart, quadriceps, gastrocnemius and diaphragm. Untreated control mice, GAA$^{-/-}$×CD63hu/hu and untreated wild-type GAA control mice, GAA+/+; CD63hu/hu (4) were also tested under the same conditions. Glycogen levels were at very low levels in both anti-hCD63::GAA treated mice and anti-ITGA7::GAA treated mice groups, as in the wild-type mice. See FIG. 10B.

Example 8: At Comparable Serum Levels, AAV Anti-CD63::GAA Treatment is More Effective than AAV with Optimized GAA Construct CD63 HumIn GAA KO mice (GAA$^{-/-}$×CD63$^{hu/hu}$) infected with AAVs containing a liver specific enhancer (serpina 1; SEQ ID NO:9) and a liver specific promoter (LSP; TTR; SEQ ID NO:8) driving the expression of an anti-hCD63::GAA multidomain therapeutic (SEQ ID NO:10), which uses a chymotrypsinogen B2 signal peptide (SP7) and contains amino acids 36-952 of human GAA (Δ8GAA; SEQ ID NO:78) exhibited significant gains in tests of muscle strength and coordination. Three different doses were given for each virus: 5e11 vg/kg, 2e12 vg/kg, and 4e12 vg/kg. Serum was collected by submandibular bleeds on a regular basis. One month post-AAV infection, mice were sacrificed. Cardiac and skeletal muscle tissue samples were collected and snap frozen in liquid nitrogen and kept at −80° C. for storage. Glycogen in tissues were measured by homogenizing tissues by bead impaction in distilled water. Samples were boiled and centrifuged, and the supernatants were used in a commercial glycogen assay kit. Serum was quantified using western blot with an antibody against human GAA as described in previous examples. For each mouse, the glycogen level in each tissue was plotted against the serum level of the construct at 1 month. 4-parameter curve fits were used to determine the EC50 of the two treatments in each tissue.

Infection with AAVs containing a liver specific promoter (LSP) encoding either anti-hCD63::GAA or sp7-Δ8GAA provided comparable serum levels of GAA at each infection dose. FIG. 11. However, in every muscle tissue assayed, an ~2.2 fold reduction in EC50 was observed when using anti-hCD63::GAA vs. sp7-Δ8GAA, demonstrating that at equivalent serum levels, anti-CD63::GAA clears glycogen more efficiently than a modified GAA expression construct that is not fused to an antibody. See FIG. 12 and Table 10.

TABLE 10

EC$_{50}$ (95% Confidence Interval) of AAV anti-hCD63::GAA and AAV sp7-Δ8GAA in heart, diaphragm, quadricep, and tricep

| Tissue | Construct | EC$_{50}$ of glycogen clearance (arbitrary units) | 95% Confidence Interval for EC$_{50}$ |
|---|---|---|---|
| Heart | sp7-Δ8GAA | 0.038 | 0.00036-0.064 |
|  | anti-hCD63::GAA | 0.017 | 0.0061-0.029 |
| Diaphragm | sp7-Δ8GAA | 0.135 | wide |
|  | anti-hCD63::GAA | 0.057 | 0.034-0.080 |
| Quadriceps | sp7-Δ8GAA | 0.187 | 0.14-0.31 |
|  | anti-hCD63::GAA | 0.080 | wide |
| Triceps | sp7-Δ8GAA | 0.19 | 0.13-0.41 |
|  | anti-hCD63::GAA | 0.083 | 0.069 to 0.11 |

Example 9: Exemplary CD63 Antibodies

Generation of Anti-Human CD63 Antibodies

Anti-human CD63 antibodies were obtained by immunizing a mouse (e.g., an engineered mouse comprising DNA encoding human immunoglobulin heavy and human kappa light chain variable regions), with human CD63.

Following immunization, splenocytes were harvested from each mouse and either (1) fused with mouse myeloma cells to preserve their viability and form hybridoma cells and screened for human CD63 specificity, or (2) B-cell sorted (as described in US 2007/0280945A1) using a either a human CD63 fragment as the sorting reagent that binds and identifies reactive antibodies (antigen-positive B cells).

Chimeric antibodies to human CD63 were initially isolated having a human variable region and a mouse constant region using, e.g., VELOCIMMUNE technology as described in U.S. Pat. Nos. 7,105,348; 8,642,835; and U.S. Pat. No. 9,622,459, each of which is incorporated herein by reference.

In some antibodies, for testing purposes, mouse constant regions were replaced with a desired human constant region, for example wild-type human CH or modified human CH (e.g. IgG1, IgG2 or IgG4 isotypes), and light chain constant region (CL), to generate a fully human anti-hCD63, including a fully human bispecific antibody comprising an anti-hCD63antibody or antigen binding portion thereof. While the constant region selected may vary according to specific use, high affinity antigen-binding and target specificity characteristics reside in the variable region.

Certain biological properties of the exemplary bispecific antibodies comprising an anti-human CD63 binding arm generated in accordance with the methods of this Example are described in detail in the Examples set forth below.

Heavy and Light Chain Variable Region Amino Acid and Nucleic Acid Sequences of Anti-CD63 Antibodies Table 11 sets forth sequence identifiers of a nucleic acid (NA) sequence encoding, and in parentheses an amino acid (AA) sequence of, a heavy or light chain variable region (HCVR or LCVR, respectively), or a heavy or light chain CDR (HCDR and LCDR, respectively) of selected anti-CD63 antibodies used to generate the multidomain therapeutic anti-CD63::GAA proteins disclosed herein.

TABLE 11 anti-CD63 Sequence Identifiers

| Antibody Designation | SEQ ID NOs: | | | | | | | |
|---|---|---|---|---|---|---|---|---|
| | HCVR NA (AA) | HCDR1 NA (AA) | HCDR2 NA (AA) | HCDR3 NA (AA) | LCVR NA (AA) | LCDR1 NA (AA) | LCDR2 NA (AA) | LCDR3 NA (AA) |
| H1M12451N | 13 (14) | 15 (16) | 17 (18) | 19 (20) | 21 (22) | 23 (24) | 25 (26) | 27 (28) |
| H2M12395N | 29 (30) | 31 (32) | 33 (34) | 35 (36) | 37 (38) | 39 (40) | 41 (42) | 43 (44) |
| H4H12450N | 45 (46) | 47 (48) | 49 (50) | 51 (52) | 53 (54) | 55 (56) | 57 (58) | 59 (60) |
| H2M12450N | 61 (62) | 63 (64) | 65 (66) | 67 (68) | 69 (70) | 71 (72) | 73 (74) | 74 (76) |

Binding by Parental Anti-Human CD63 Antibodies

Relative cell surface binding of the anti-CD63 antibodies to human CD63 expressing cells was accessed via flow cytometry using CD63 positive HEK293 cells (ATCC, Cat # CRL-1573), which endogenously express human CD63, and CD63 negative HEK293/CD63 knock out cells. For the assay, cells were plated in PBS without calcium and magnesium (VWR, Cat#45000-446), containing 2% FBS (Saradigm Cat#1500-500) (Staining Buffer) in 96 well V-bottom plates (Axygen Scientific, Cat# P-96-450-V-C-S). Cells were then incubated with anti-CD63 antibodies or isotype control antibodies at concentrations ranging from 100 nM to 1.7 pM for 30 minutes on ice. Wells containing no antibody were used as controls. HEK293/CD63KO cells were stained with only the highest concentration (100 nM) of the antibodies. The cells were then washed once with staining buffer and were incubated with a PE conjugated anti-mouse Fc secondary antibody (Jackson ImmunoResearch, Cat#115-115-164) at 100 nM for 30 minutes at 4° C. Cells were then washed and fixed using a 50% solution of Cytofix (BD Biosciences, Cat#554655) diluted in PBS. Samples were run on the Intellicyte Hypercyt flow cytometer and results were analyzed in ForeCyt software (Intellicyte) to calculate the mean fluorescent intensity (MFI). Measured values were analyzed using a four parameter logistic equation over a 12-point response curve using GraphPad Prism and the resulting $EC_{50}$ values are reported (Table 12). The signal to noise ratio (S/N) was determined by calculating the ratio of the anti-CD63 antibodies or the control antibodies MFI to the wells containing no antibodies (Table 12).

As shown in Table 12, three of the anti-CD63 antibodies of the invention demonstrated binding to HEK293 cells with S/N values ranging from 21.0 to 31.6 and $EC_{50}$ values ranging from 0.5 nM to 1.9 nM. The non-binding controls did not demonstrate binding to HEK293 cells (S/N≤1.5). Both the anti-CD63 antibodies and the isotype control antibodies demonstrated weak to little binding to the HEK293/CD63KO cells (S/N≤4.4).

TABLE 12

Binding of anti-CD63 antibodies to HEK293 and HEK293/CD63 KO cells as measured by flow cytometry

| Antibody | HEK293 $EC_{50}$ (nM) | HEK293 (S/N) | HEK293/CD63 KO (S/N) |
|---|---|---|---|
| H2M12450N | 0.5 | 26.7 | 2.9 |
| H1M12451N | 1.8 | 31.6 | 4.1 |
| H2M12395N | 1.9 | 21.0 | 2.9 |
| Isotype Control 1 | ND | 1.4 | 4.4 |
| Isotype Control 2 | ND | 1.5 | 1.6 |

ND = Not determined

The ability of the anti-CD63 monoclonal antibodies of the invention to bind to human CD63 expressing cells was also determined using an electrochemiluminescence (ECL) based detection assay.

To generate overexpressing cells, mouse embryonic fibroblast NIH3T3 cells (ATCC, Cat# CRL-1658) were transfected to form a cell line "NIH3T3/hCD63" that stably expresses human CD63 (hCD63; amino acids M1-M238 of accession number NP_001771; SEQ ID NO:77). Expression levels of human CD63 in endogenously expressing cells, a human androgen-sensitive prostate adenocarcinoma cell line, LNCAP (ATCC, Cat# CRL-1740), and human primary glioblastoma cell line, U87MG (ATCC, Cat# HTB-14) were analyzed with a Quantum™ Alexa Fluor® 647 MESF (Bangs Laboratories, Cat#647B) and a Simply Cellular® anti-Mouse IgG (Bangs Laboratories Inc, Cat#815) following the manufacturer's instructions. LNCAP cells were determined to have a lower human CD63 copy number than U87MG cells. Non-transfected NIH3T3 cells, which have no detectable expression of human CD63 by fluorescence activated cell sorting (FACS), were included as a negative control.

Briefly, cell lines were rinsed once in PBS buffer without $Ca^{2+}/Mg^{2+}$ and incubated for 10 minutes at 37° C. with Enzyme Free Cell Dissociation Solution (Millipore, Cat# S-004-C) to detach the cells. Cells were then washed once with PBS with $Ca^{2+}/Mg^{2+}$ and counted with a Cellometer™ Auto T4 cell counter (Nexcelom Bioscience, LLC). Approximately $2.0 \times 10^4$ NIH3T3/hCD63, LNCAP, U87MG or NIH3T3 cells were seeded separately onto 96-well carbon electrode plates (Meso Scale Discovery, Cat# L15XB-6) and were then incubated for one hour at 37° C. Nonspecific binding sites were blocked with 2% BSA (w/v) in PBS with $Ca^{2+}/Mg^{2+}$ for one hour at room temperature (RT). Solutions containing anti-CD63 antibodies or isotype control antibodies at a range of concentrations (1.7 pM to 100 nM) in 0.5% BSA (w/v) in PBS with $Ca^{2+}/Mg^{2+}$, as well as control buffer alone, were then added in duplicate to the plate-bound NIH3T3/hCD63, LNCAP, U87MG or NIH3T3 cells and incubated for one hour at RT. Plates were subsequently washed to remove unbound antibodies using an AquaMax2000 plate washer with a cell washing head (MDS Analytical Technologies). The plate-bound antibodies were detected with 1 μg/mL of either a SULFO-TAG™-conjugated goat polyclonal anti-human IgG antibody specific for Fcγ fragment (Jackson Immunoresearch, Cat#109-005-098) or a SULFO-TAG™-conjugated goat polyclonal anti-mouse IgG antibody specific for Fcγ fragment (Jackson Immunoresearch, Cat# 115-005-164) for one hour at RT. Plates were washed and then incubated with Read Buffer (MSD, Cat# R92TD-2) according to the manufacturer's instructions. Luminescent signals were measured using a SECTOR Imager (MSD). Luminescence intensity, measured in relative light units (RLU), was recorded to indicate the binding intensity of each antibody at the range of concentrations tested. The ratio of signal detected with 3.7 nM antibody binding to human CD63 expressing cells compared to the same concentration of antibody binding to negative cells was reported as an indication of specificity of CD63 binding. Antibodies with the binding ratio of greater than 3 were classified as specific binders and antibodies with the binding ratio less than or equal to 3 were classified as non-binders and marked as NB in Table 13. In addition, the direct binding signals (in RLU) were analyzed as a function of the antibody concentration and the data were fitted with a sigmoidal (four-parameter logistic) dose-response model using GraphPad Prism™ software. The $EC_{50}$ value for binding to human CD63 expressing cells, defined as the concentration of antibody at which 50% of the maximal binding signal is detected, was determined to indicate potency of each antibody and reported in Table 13 only for specific binders.

As shown in Table 13, the four anti-CD63 antibodies generated as described in Example 9 and a Comparator Ab (Comparator 1) bound specifically to human CD63 expressed on engineered NIH3T3/hCD63 cells as well as that endogenously expressed on LNCAP and U87MG cell lines. The four anti-CD63 antibodies described in Example 9 bound to NIH3T3/hCD63 cells with $EC_{50}$ values ranging from 280 pM to 970 pM and binding ratios over the negative cell line ranging from 91 to 281-fold. The four anti-CD63 antibodies of the invention bound to U87MG cells with $EC_{50}$ values ranging from 500 pM to 1.4 nM and binding ratios over the negative cell line ranging from 52 to 272-fold. The four anti-CD63 antibodies generated as described in Example 9 bound to LNCAP cells with $EC_{50}$ values ranging from 210 pM to 1.7 nM and binding ratios over the negative cell line ranging from 7 to 20-fold. The lower binding ratios on LNCAP cells are in agreement with lower CD63 copy number on these cells compared to U87MG cells. The isotype control antibodies were non-binders, as expected, with cell binding ratios less than or equal to 3.

TABLE 13

Anti-CD63 Antibodies Binding to Human CD63 expressing cells as measured by Electrochemiluminescence based detection

| Antibody | Cell Binding Potency, $EC_{50}$ (M) | | | Ratio at 3.7 nM Ab concentration of Cell Binding Signal (RLU) to human CD63 cells relative to negative NIH3T3 | | |
|---|---|---|---|---|---|---|
| | NIH3T3/hCD63 | U87MG | LNCAP | NIH3T3/hCD63 | U87MG | LNCAP |
| H1M12451N | 5.7E−10 | 9.5E−10 | 1.7E−09 | 91 | 52 | 7 |
| H2M12395N | 2.9E−10 | 7.9E−10 | 3.5E−10 | 256 | 171 | 18 |
| H4H12450N | 9.7E−10 | 1.4E−09 | 1.4E−09 | 281 | 272 | 20 |
| H2M12450N | 2.8E−10 | 5.0E−10 | 2.1E−10 | 230 | 175 | 20 |
| CONTROLS | | | | | | |
| Comparator Ab 1 | 5.7E−10 | 6.7E−10 | 2.0E−09 | 253 | 271 | 16 |
| Human IgG4 isotype control | NB | NB | NB | 1 | 1 | 1 |
| Mouse IgG2 isotype control | NB | NB | NB | 3 | 2 | 2 |

NB—non-binder;
antibodies with a binding ratio of less than or equal to 3 were classified as non-binders.

Cytotoxicity Mediated by Parental Anti-Human CD63 Antibodies

In order to assess the ability of an anti-CD63 antibody described herein to internalize in CD63 expressing cells, an in vitro indirect cytotoxicity assay was performed. Human CD63 positive T47D cells (ATCC, Cat #HTB-133) and human CD63 negative NIH3T3 cells (ATCC, Cat #CRL-1658) were respectively seeded in PDL-coated 96-well plates (BD Biocoat, Cat #356461) at either 6,000 cells per well in RPMI (Irvine Scientific, Cat #9160) containing 10% FBS (ATCC, Cat#30-2020), pencillin/streptomycin/L-glutamine (Gibco, Cat #10378-016), 50 uM Beta-Mercaptoethanol (Sigma, Cat #M7522) (growth media), Sodium Pyruvate 100 mM (Millipore, Cat #TMS-005-C), HEPES 1M (Irvine Scientific, Cat #9319), and Insulin bovine 10 ug/mL (Gemini BioProducts, Cat #700-912P) or 2,000 cells per well in DME high glucose (Irvine Scientific, Cat #9033), 10% Bovine calf serum (Hyclone, Cat #SH30072.03), plus pencillin/streptomycin/L-glutamine (Gibco, Cat #10378-016) and grown overnight at 37° C. in 5% $CO_2$. For cell viability curves, cells were incubated for 5 minutes at 37° C. with a serially diluted anti-CD63 antibody (H2M12450N) or a non-binding isotype control antibody at concentrations ranging from 3.0 pM to 2.2 nM. A Fab anti-mFc secondary antibody conjugated to the cytotoxic payload MMAF (Moradec, Cat #AM-201AF-50) was then added at 20 nM to each well. Media alone served as a negative control, and 33 µM of digitonin (Promega, Cat #G9441) was used to determine the maximum cytotoxicity. Following a 72 hour incubation, cell viability was measured using Cell Counting Kit-8 (Dojindo, Cat #CK04) as per manufacturer's protocols with an incubation time range of 1-3 hours. The absorbance at 450 nm ($OD_{450}$) was measured on an Envision plate reader (PerkinElmer). Background $OD_{450}$ levels from digitonin treated cells were subtracted from all wells and viability was expressed as a percentage of the untreated controls (% viability). $IC_{50}$ values were determined from a four-parameter logistic equation over an 8-point response curve (GraphPad Prism). All $IC_{50}$ values are expressed in nM concentration and the minimum % viable cells remaining after treatment is reported.

As summarized in Table 14, the anti-CD63 antibody, H2M12450N, reduced T47D viability to 21% with an $IC_{50}$ value of 0.24 nM, whereas the isotype control reduced viability to only 64%. The antibodies had little to no impact on the viability of the NIH3T3 cell line.

TABLE 14

Anti-CD63 antibody internalization measured by an indirect cytotoxicity assay in T47D and NIH3T3 cells

| Antibody | T47D (nM) $IC_{50}$ | T47D % Viability | NIH3T3 (nM) $IC_{50}$ | NIH3T3 % Viability |
|---|---|---|---|---|
| H2M12450N | 0.24 | 21 | ND | 83 |
| Isotype Control | ND | 64 | ND | 91 |

ND = Not determined

Biacore Binding Kinetics of Anti-CD63 Monoclonal Antibodies Binding to CD63 (EC2) Loop Reagents Measured at 25° C. and 37° C.

Equilibrium dissociation constants ($K_D$) for different CD63loop reagents binding to purified anti-CD63 monoclonal antibodies were determined using a real-time surface plasmon resonance based Biacore T200 biosensor or Biacore 2000 biosensor. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore CM5 sensor chip surface was first derivatized by amine coupling with either a rabbit anti-mouse Fc specific polyclonal antibody (GE Healthcare, Cat# BR100838) or an anti-human Fab kit (GE Healthcare, Cat#28958325) to capture anti-CD63 monoclonal antibodies. Binding studies were performed on either recombinant human CD63 extracellular loop 2 expressed with a C-terminal Myc-Myc-hexahistidine (hCD63 EC loop 2-MMH; SEQ ID NO:80) or recombinant human CD63 extracellular loop 2 expressed with a C-terminal human Fc tag (hCD63 EC loop 2-hFc; SEQ ID NO:81). Different concentrations of hCD63 EC loop 2-MMH or hCD63 EC loop 2-hFc (either tested at 50 nM-12.5 nM in a 4-fold dilution or at 90 nM-0.37 nM in 3-fold serial dilutions) were first prepared in HBS-ET running buffer and were injected over the anti-mouse Fc captured anti-CD63 monoclonal antibody surface for 4 minutes at a flow rate of 35 µL/minute or 50 µL/minute, while the dissociation of monoclonal antibody bound CD63 reagent was monitored for 8 or 10 minutes in HBS-ET running buffer. The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\text{min}) = \frac{\ln(2)}{60 * kd}$$

Binding kinetics parameters for human CD63 EC loop 2 protein binding to different anti-CD63 monoclonal antibodies of the invention at 25° C. and 37° C. are shown in Tables 15 through 18.

At 25° C., all of the anti-CD63 monoclonal antibodies of the invention bound to hCD63 EC loop 2-MMH with $K_D$ values ranging from 530 pM to 11.0 nM, as shown in Table 15. At 37° C., all of the anti-CD63 monoclonal antibodies of the invention bound to hCD63 EC loop 2-MMH with $K_D$ values ranging from 1.15 nM to 56.4 nM, as shown in Table 16.

At 25° C., all of the anti-CD63 monoclonal antibodies of the invention bound to hCD63 EC loop 2-hFc with $K_D$ values ranging from 150 pM to 753 pM, as shown in Table 17. At 37° C., all of the anti-CD63 monoclonal antibodies of the invention bound to hCD63 EC loop 2-hFc with $K_D$ values ranging from 119 pM to 3.38 nM, as shown in Table 18.

TABLE 15

Binding kinetics parameters of human CD63 EC loop2-MMH binding to anti-CD63 monoclonal antibodies at 25° C.

| Antibody | mAb Capture Level (RU) | 50 nM or 90 nM Ag Bound (RU) | $k_a$ ($M^{-1}s^{-1}$) | $k_d$ (1/s) | $K_D$ (M) | t½ (min) |
|---|---|---|---|---|---|---|
| H2M12450N | 592 | 65 | 2.27E+05 | 2.79E−04 | 1.23E−09 | 41 |
| H2M12395N | 472 | 42 | 1.66E+05 | 1.82E−03 | 1.10E−08 | 6 |
| H1M12451N | 525 | 52 | 8.59E+04 | 4.30E−04 | 5.00E−09 | 27 |
| H4H12450N | 296 | 24 | 1.39E+05 | 7.37E−05 | 5.30E−10 | 156.7 |

TABLE 16

Binding kinetics parameters of human CD63 EC loop2-MMH binding to anti-CD63 monoclonal antibodies at 37° C.

| Antibody | mAb Capture Level (RU) | 50 nM Ag Bound (RU) | $k_a$ $(M^{-1}s^{-1})$ | $k_d$ (1/s) | $K_D$ (M) | $t^{1/2}$ (min) |
|---|---|---|---|---|---|---|
| H2M12450N | 617 | 58 | 1.75E+05 | 2.01E−04 | 1.15E−09 | 57 |
| H2M12395N | 535 | 31 | 1.65E+05 | 9.32E−03 | 5.64E−08 | 1 |
| H1M12451N | 597 | 44 | 8.89E+04 | 1.90E−03 | 2.14E−08 | 6 |

TABLE 17

Binding kinetics parameters of human CD63 EC loop2-hFC binding to anti-CD63 monoclonal antibodies at 25° C.

| Antibody | mAb Capture Level (RU) | 50 nM Ag Bound (RU) | $k_a$ $(M^{-1}s^{-1})$ | $k_d$ (1/s) | $K_D$ (M) | $t^{1/2}$ (min) |
|---|---|---|---|---|---|---|
| H2M12450N | 592 | 134 | 3.20E+05 | 4.66E−05 | 1.50E−10 | 248 |
| H2M12395N | 472 | 117 | 6.77E+05 | 5.10E−04 | 7.53E−10 | 23 |
| H1M12451N | 525 | 107 | 1.19E+05 | 8.40E−05 | 7.04E−10 | 138 |

TABLE 18

Binding kinetics parameters of human CD63 EC loop2-hFC binding to anti-CD63 monoclonal antibodies at 37° C.

| Antibody | mAb Capture Level (RU) | 50 nM Ag Bound (RU) | $k_a$ $(M^{-1}s^{-1})$ | $k_d$ (1/s) | $K_D$ (M) | $t^{1/2}$ (min) |
|---|---|---|---|---|---|---|
| H2M12450N | 617 | 138 | 4.11E+05 | 4.89E−05 | 1.19E−10 | 236 |
| H2M12395N | 535 | 123 | 5.29E+05 | 1.79E−03 | 3.38E−09 | 6 |
| H1M12451N | 597 | 118 | 6.51E+05 | 3.31E−04 | 5.09E−10 | 35 |

Generation of Bispecific Antibodies to Determine Internalization of Bispecific Complex Having an Anti-CD63 Binding Arm To assess the ability of anti-CD63 antibodies generated as described in this example to internalize as part of a bispecific antigen-binding molecule, the antibodies were reconstructed into bispecific formats where one binding arm was the anti-CD63 antibody VH/VL pair (see Table 11 parental antibodies) and the other was an irrelevant binding arm. Standard methods of making bispecific antibodies were used, and exemplary methods are described in, e.g., US Application Publication No. 2010/0331527, and U.S. Pat. No. 5,731,168, each of which is incorporated herein by reference. The bispecific antibodies were tested for their ability to internalize using human CD63 expressing cells. For the assay, HEK293 cells, which endogenously express human CD63, were plated at a density of 10,000 cells/well in DMEM containing 10% FBS and penicillin-streptomycin/L-glutamine (Gibco, Cat#10378016) in clear bottom black Poly-D-Lysine coated 96-well plates (Greiner, Cat#655946). Two days later, the media was replaced with fresh media containing anti-CD63 bispecific antibodies and a negative control antibody in a 2-fold dilution series beginning at 10 μg/mL to 0.157 μg/mL, along with a media only control. Cells were then incubated at 37° C. for 3 hours to allow for antibody internalization. Following the incubation, cells were washed with PBS, fixed in 4% paraformaldehyde (Thermo Scientific, Cat#28908) for 20 minutes at room temperature, and subsequently permeablized with 0.2% Triton X-100 (Spectrum Chemical, Cat# TR135) in 5% normal goat serum (NGS) (Gibco, Cat# PCN5000) for 20 minutes at room temperature. Cells were then incubated with either 2 μg/mL of donkey anti-mouse IgG Alexa Fluor-647 Fab (Manufacture, Cat#115-606-006) or 2 μg/mL of goat anti-human IgG Alexa Fluor-647 Fab (Jackson ImmunoResearch, Cat#115-606-006) in 5% NGS for 1 hour at room temperature. The secondary antibody solution was removed, then cell were washed with PBS, and subsequently fresh PBS containing 2 drops/mL of NucBlue (Invitrogen, CAT# R37605) was added to stain live cell nuclei. Antibody internalization and nuclei were imaged at 40x on the ImageXpress High-Content Imaging System (Molecular Devices) and antibody internalization was quantified using the MetaXpress Software Transfluor Application Module (Molecular Devices). Antibody internalization is reported as pit integrated intensity per cell±standard deviation (SD).

As shown in Table 19, all of the bispecific antibodies incorporating a single arm binding to human CD63 (derived from either H1M12451, H2M12450, or H2M12395) and an irrelevant non-binding arm demonstrated efficient internalization into HEK293 cells. The bispecific antibody incorporating one binding arm of H2M12450 demonstrated a higher amount of internalization than the other bispecific antibodies tested.

TABLE 19

Internalization of anti-CD63 bispecific antibodies by HEK293 cells

| Concentration of antibody (µg/mL) | Internalization of antibody (pit integrated intensity) ± SD | | | |
|---|---|---|---|---|
| | H2M12395N bispecific | H2M12450N bispecific | H1M12451N bispecific | Negative control Ab |
| 10 | 1.05E+06 ± 4.56E+05 | 4.34E+06 ± 8.77E+05 | 8.26E+05 ± 2.67E+05 | 4.58E+03 ± 6.50E+03 |
| 5 | 1.07E+06 ± 4.06E+05 | 4.31E+06 ± 5.48E+05 | 5.45E+05 ± 5.20E+04 | 1.23E+03 ± 8.85E+02 |
| 2.5 | 2.73E+05 ± 6.01E+04 | 3.92E+06 ± 5.80E+05 | 3.27E+05 ± 1.06E+05 | 7.70E+02 ± 6.09E+02 |
| 1.25 | 1.89E+05 ± 6.61E+04 | 2.72E+06 ± 2.63E+05 | 1.20E+05 ± 3.91E+04 | 1.43E+03 ± 1.19E+03 |
| 0.625 | 2.03E+05 ± 9.37E+04 | 1.75E+06 ± 1.39E+05 | 7.87E+04 ± 1.07E+04 | 3.37E+03 ± 5.22E+03 |
| 0.3125 | 3.95E+04 ± 8.23E+03 | 8.57E+05 ± 1.60E+05 | 3.77E+04 ± 1.22E+04 | 1.99E+03 ± 2.19E+03 |
| 0.15625 | 2.81E+04 ± 1.30E+04 | 2.42E+05 ± 2.54E+04 | 7.23E+03 ± 6.09E+03 | 1.87E+03 ± 1.16E+03 |
| 0 | 3.72E+03 ± 1.66E+03 | 8.21E+03 ± 3.47E+03 | 1.66E+04 ± 1.80E+04 | 1.10E+03 ± 1.56E+03 |

What is claimed is:

1. A polynucleotide encoding a multidomain therapeutic protein comprising a delivery domain and an enzyme domain, wherein the delivery domain binds to an internalization effector;
   wherein the internalization effector is CD63; and
   wherein the delivery domain comprises:
   an amino acid sequence of SEQ ID NO:2, or
   an amino acid sequence selected from the group consisting of an amino acid sequence of an HCVR set forth in Table 11; an amino acid sequence of a LCVR set forth in Table 11; an amino acid sequence of an HCDR1 set forth in Table 11; an amino acid sequence of an HCDR2 set forth in Table 11; an amino acid sequence of an HCDR3 set forth in Table 11; an amino acid sequence of a LCDR1 set forth in Table 11; an amino acid sequence of a LCDR2 set forth in Table 11; an amino acid sequence of a LCDR3 set forth in Table 11; and an HCVR/LCVR amino acid pair set forth as SEQ ID NOs:14/22, SEQ ID NOs:30/38, SEQ ID NOs:46/54, or SEQ ID NOs:62/70, wherein the HCVR/LCVR amino acid pair comprises from N-terminal to C-terminal: the HCVR, an optional linker, and the LCVR.

2. The polynucleotide of claim 1, wherein the enzyme domain comprises a hydrolase.

3. The polynucleotide of claim 1, wherein the enzyme domain comprises a glycosylase.

4. The polynucleotide of claim 1, wherein the enzyme domain comprises a glycosidase.

5. The polynucleotide of claim 1, wherein the enzyme domain comprises an alpha-glucosidase.

6. The polynucleotide of claim 1, wherein the enzyme domain comprises an amino acid sequence of SEQ ID NO:1 or a fragment thereof.

7. The polynucleotide of claim 1, further comprising a virus nucleic acid sequence and/or a locus-targeting nucleic acid sequence.

8. The polynucleotide of claim 1, further comprising a virus nucleic acid sequence and at least one of (i) a locus-targeting nucleic acid sequence, (ii) a tissue specific regulatory element, or (iii) a combination of (i) and (ii).
   wherein the virus nucleic acid sequence is an adeno-associated virus (AAV) nucleic acid internal terminal repeat sequence comprising a sequence set forth as SEQ ID NO:6, SEQ ID NO:7, or a combination thereof,
   wherein the locus-targeting nucleic acid sequence targets the polynucleotide to a locus selected from the group consisting of an EESYR locus, a SARS locus, position 188,083,272 of human chromosome 1 or its non-human mammalian orthologue, position 3,046,320 of human chromosome 10 or its non-human mammalian orthologue, position 67,328,980 of human chromosome 17 or its non-human mammalian orthologue, an adeno-associated virus site 1 (AAVS1) on human chromosome 19 or its non-human mammalian orthologue, a chemokine receptor 5 (CCR5) gene, a chemokine receptor gene encoding an HIV-1 coreceptor, a mouse Rosa26 locus or its non-murine mammalian orthologue, and a human albumin (alb) locus, and
   wherein the tissue specific regulatory element is a liver specific enhancer comprising the sequence set forth as SEQ ID NO: 9 and/or a liver specific promoter comprising the sequence set forth as SEQ ID NO:10.

9. A polynucleotide encoding a multidomain therapeutic protein comprising a delivery domain and an enzyme domain, wherein the delivery domain binds to an internalization effector, and wherein the polynucleotide comprises a nucleic acid sequence of SEQ ID NO:11 and/or encodes an amino acid sequence set forth as SEQ ID NO:10 or SEQ ID NO:79.

10. A composition comprising a gene therapy vector comprising the polynucleotide of claim 1,
    wherein the gene therapy vector is selected from the group consisting of (i) a viral vector comprising the polynucleotide, (ii) the polynucleotide by itself as a naked polynucleotide, (iii) a complex comprising the polynucleotide complexed with a metal, a cation, an anion, a lipid, a polymer, and any combination thereof, and (iv) any combination of (i)-(iii).

11. The composition of claim 10, wherein the gene therapy vector is a viral vector selected from the group consisting of a retrovirus, adenovirus, herpes simplex virus, pox virus, vaccinia virus, lentivirus, or an adeno-associated virus.

12. The composition of claim 11, wherein the gene therapy vector is an AAV2/8 chimera.

13. The composition of claim 10, further comprising a pharmaceutically acceptable carrier, wherein the composition is a pharmaceutically acceptable composition for administration into a subject, and wherein the composition comprises a therapeutically effective amount of the polynucleotide.

14. A recombinant multidomain therapeutic protein comprising a delivery domain and an enzyme domain, wherein the protein is encoded by the polynucleotide according to claim 1.

15. The recombinant multidomain therapeutic protein of claim 14, comprising a sequence set forth as SEQ ID NO:10 or SEQ ID NO:79.

16. A method of expressing in a cell a recombinant multidomain therapeutic protein comprising a delivery domain and an enzyme domain, the method comprising:
    a. contacting the cell with the composition of claim 10;
    b. allowing the polynucleotide to integrate into a genomic locus of the cell; and
    c. allowing the cell to produce the recombinant multidomain therapeutic protein.

17. The method of claim 16, wherein the genomic locus of the cell is a safe harbor locus selected from the group consisting of an EESYR locus, a SARS locus, position 188,083,272 of human chromosome 1 or its non-human mammalian orthologue, position 3,046,320 of human chromosome 10 or its non-human mammalian orthologue, position 67,328,980 of human chromosome 17 or its non-human mammalian orthologue, an adeno-associated virus site 1 (AAVS1) on human chromosome 19 or its non-human mammalian orthologue, a chemokine receptor 5 (CCR5) gene, a chemokine receptor gene encoding an HIV-1 coreceptor, a mouse Rosa26 locus or its non-murine mammalian orthologue, and a human albumin (alb) locus.

18. The method of claim 16, wherein the polynucleotide comprises a nucleic acid sequence of SEQ ID NO:11 and/or encodes an amino acid sequence set forth as SEQ ID NO:10 or SEQ ID NO:79.

19. The polynucleotide of claim 1, wherein the enzyme domain comprises an amino acid sequence of SEQ ID NO:13 or a fragment thereof.

20. The polynucleotide of claim 1, wherein the enzyme domain comprises an amino acid sequence of SEQ ID NO:78 or a fragment thereof.

* * * * *

UNITED STATES PATENT AND TRADEMARK OFFICE
CERTIFICATE OF CORRECTION

PATENT NO. : 11,208,458 B2
APPLICATION NO. : 16/001717
DATED : December 28, 2021
INVENTOR(S) : Andrew Baik et al.

It is certified that error appears in the above-identified patent and that said Letters Patent is hereby corrected as shown below:

In the Claims

Claim 8, Line 26, Column 126, Line 17:
the sequence set forth as SEQ ID NO:10.
Should be:
--the sequence set forth as SEQ ID NO:8.--

Signed and Sealed this
Second Day of August, 2022

Katherine Kelly Vidal
*Director of the United States Patent and Trademark Office*

SEQUENCE LISTING

<160> NUMBER OF SEQ ID NOS: 81

<210> SEQ ID NO 1
<211> LENGTH: 952
<212> TYPE: PRT
<213> ORGANISM: Homo sapiens

<400> SEQUENCE: 1

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255
```

```
Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
```

```
                    675                 680                 685
Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                    725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
                    755                 760                 765

Leu Gly Thr Trp Tyr Asp Leu Gln Thr Val Pro Val Glu Ala Leu Gly
770                 775                 780

Ser Leu Pro Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                    805                 810                 815

His Leu Arg Ala Gly Tyr Ile Ile Pro Leu Gln Gly Pro Gly Leu Thr
                820                 825                 830

Thr Thr Glu Ser Arg Gln Gln Pro Met Ala Leu Ala Val Ala Leu Thr
                    835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                    885                 890                 895

Ala Gly Leu Gln Leu Gln Lys Val Thr Val Leu Gly Val Ala Thr Ala
                900                 905                 910

Pro Gln Gln Val Leu Ser Asn Gly Val Pro Val Ser Asn Phe Thr Tyr
                    915                 920                 925

Ser Pro Asp Thr Lys Val Leu Asp Ile Cys Val Ser Leu Leu Met Gly
                930                 935                 940

Glu Gln Phe Leu Val Ser Trp Cys
945                 950

<210> SEQ ID NO 2
<211> LENGTH: 245
<212> TYPE: PRT
<213> ORGANISM: Artificial
<220> FEATURE:
<223> OTHER INFORMATION: synthetic

<400> SEQUENCE: 2

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
                20                  25                  30

Tyr Met Ser Trp Val Arg Gln Thr Pro Glu Lys Arg Leu Glu Trp Val
            35                  40                  45

Ala Tyr Ile Ser Ser Ser Gly Gly Ser Thr Tyr Tyr Ser Asp Thr Val
        50                  55                  60

Lys Gly Gln Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
```

```
            85                  90                  95
Ala Arg Arg Glu Asp Tyr Asp Gly Arg Leu Thr Tyr Trp Gly Gln Gly
                100                 105                 110

Thr Leu Val Thr Ile Ser Ala Gly Gly Ser Gly Gly Gly Gly Ser Gly
            115                 120                 125

Gly Gly Gly Ser Gly Gly Asp Ile Val Leu Thr Gln Ser Pro Ala Ser
        130                 135                 140

Leu Ala Val Ser Leu Gly Gln Arg Ala Thr Ile Ser Cys Arg Ala Ser
145                 150                 155                 160

Lys Ser Val Ser Thr Ser Gly Tyr Ser Tyr Met Asn Trp Tyr Gln Gln
                165                 170                 175

Lys Pro Gly Gln Pro Pro Lys Val Leu Ile Tyr Leu Ala Ser Lys Leu
            180                 185                 190

Glu Ser Gly Val Pro Ala Arg Phe Ser Gly Ser Gly Ser Gly Thr Asp
        195                 200                 205

Phe Thr Leu Asn Ile His Pro Val Glu Glu Glu Asp Ala Ala Thr Tyr
    210                 215                 220

Tyr Cys Gln His Ser Arg Glu Leu Pro Tyr Thr Phe Gly Gly Gly Thr
225                 230                 235                 240

Lys Leu Glu Ile Lys
            245

<210> SEQ ID NO 3
<211> LENGTH: 21
<212> TYPE: DNA
<213> ORGANISM: Artificial
<220> FEATURE:
<223> OTHER INFORMATION: synthetic

<400> SEQUENCE: 3
ggaaccccta gtgatggagt t                                        21

<210> SEQ ID NO 4
<211> LENGTH: 16
<212> TYPE: DNA
<213> ORGANISM: Artificial
<220> FEATURE:
<223> OTHER INFORMATION: synthetic

<400> SEQUENCE: 4
cggcctcagt gagcga                                              16

<210> SEQ ID NO 5
<211> LENGTH: 21
<212> TYPE: DNA
<213> ORGANISM: Artificial
<220> FEATURE:
<223> OTHER INFORMATION: synthetic

<400> SEQUENCE: 5
cactccctct ctgcgcgctc g                                        21

<210> SEQ ID NO 6
<211> LENGTH: 141
<212> TYPE: DNA
<213> ORGANISM: Artificial
<220> FEATURE:
<223> OTHER INFORMATION: synthetic

<400> SEQUENCE: 6
cctgcaggca gctgcgcgct cgctcgctca ctgaggccgc ccgggcaaag cccgggcgtc    60
```

```
gggcgacctt tggtcgcccg gcctcagtga gcgagcgagc gcgcagagag ggagtggcca      120
actccatcac tagggttcc t                                                 141

<210> SEQ ID NO 7
<211> LENGTH: 141
<212> TYPE: DNA
<213> ORGANISM: Artificial
<220> FEATURE:
<223> OTHER INFORMATION: synthetic

<400> SEQUENCE: 7
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc      120
gagcgcgcag ctgcctgcag g                                                141

<210> SEQ ID NO 8
<211> LENGTH: 224
<212> TYPE: DNA
<213> ORGANISM: Artificial
<220> FEATURE:
<223> OTHER INFORMATION: synthetic

<400> SEQUENCE: 8
gtctgtctgc acatttcgta gagcgagtgt tccgatactc taatctccct aggcaaggtt      60
catatttgtg taggttactt attctccttt tgttgactaa gtcaataatc agaatcagca      120
ggtttggagt cagcttggca ggatcagca gcctgggttg aaggaggggg gtataaaagc       180
cccttcacca ggagaagccg tcacacagat ccacaagctc ctga                       224

<210> SEQ ID NO 9
<211> LENGTH: 72
<212> TYPE: DNA
<213> ORGANISM: Artificial
<220> FEATURE:
<223> OTHER INFORMATION: synthetic

<400> SEQUENCE: 9
gggggaggct gctggtgaat attaaccaag gtcaccccag ttatcggagg agcaaacagg      60
ggctaagtcc ac                                                          72

<210> SEQ ID NO 10
<211> LENGTH: 1133
<212> TYPE: PRT
<213> ORGANISM: Artificial
<220> FEATURE:
<223> OTHER INFORMATION: synthetic

<400> SEQUENCE: 10
```

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Ser Trp Val Arg Gln Thr Pro Glu Lys Arg Leu Glu Trp Val
        35                  40                  45

Ala Tyr Ile Ser Ser Ser Gly Gly Ser Thr Tyr Tyr Ser Asp Thr Val
    50                  55                  60

Lys Gly Gln Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys

```
                    85                  90                  95
Ala Arg Arg Glu Asp Tyr Asp Gly Arg Leu Thr Tyr Trp Gly Gln Gly
                100                 105                 110

Thr Leu Val Thr Ile Ser Ala Gly Gly Ser Gly Gly Gly Gly Ser Gly
            115                 120                 125

Gly Gly Gly Ser Gly Gly Asp Ile Val Leu Thr Gln Ser Pro Ala Ser
        130                 135                 140

Leu Ala Val Ser Leu Gly Gln Arg Ala Thr Ile Ser Cys Arg Ala Ser
145                 150                 155                 160

Lys Ser Val Ser Thr Ser Gly Tyr Ser Tyr Met Asn Trp Tyr Gln Gln
                165                 170                 175

Lys Pro Gly Gln Pro Pro Lys Val Leu Ile Tyr Leu Ala Ser Lys Leu
                180                 185                 190

Glu Ser Gly Val Pro Ala Arg Phe Ser Gly Ser Gly Ser Gly Thr Asp
            195                 200                 205

Phe Thr Leu Asn Ile His Pro Val Glu Glu Asp Ala Ala Thr Tyr
        210                 215                 220

Tyr Cys Gln His Ser Arg Glu Leu Pro Tyr Thr Phe Gly Gly Gly Thr
225                 230                 235                 240

Lys Leu Glu Ile Lys Gly Gly Gly Gly Ser Ala His Pro Gly Arg Pro
                245                 250                 255

Arg Ala Val Pro Thr Gln Cys Asp Val Pro Pro Asn Ser Arg Phe Asp
                260                 265                 270

Cys Ala Pro Asp Lys Ala Ile Thr Gln Glu Gln Cys Glu Ala Arg Gly
            275                 280                 285

Cys Cys Tyr Ile Pro Ala Lys Gln Gly Leu Gln Gly Ala Gln Met Gly
        290                 295                 300

Gln Pro Trp Cys Phe Phe Pro Ser Tyr Pro Ser Tyr Lys Leu Glu
305                 310                 315                 320

Asn Leu Ser Ser Ser Glu Met Gly Tyr Thr Ala Thr Leu Thr Arg Thr
                325                 330                 335

Thr Pro Thr Phe Phe Pro Lys Asp Ile Leu Thr Leu Arg Leu Asp Val
                340                 345                 350

Met Met Glu Thr Glu Asn Arg Leu His Phe Thr Ile Lys Asp Pro Ala
            355                 360                 365

Asn Arg Arg Tyr Glu Val Pro Leu Glu Thr Pro His Val His Ser Arg
        370                 375                 380

Ala Pro Ser Pro Leu Tyr Ser Val Glu Phe Ser Glu Glu Pro Phe Gly
385                 390                 395                 400

Val Ile Val Arg Arg Gln Leu Asp Gly Arg Val Leu Leu Asn Thr Thr
                405                 410                 415

Val Ala Pro Leu Phe Phe Ala Asp Gln Phe Leu Gln Leu Ser Thr Ser
                420                 425                 430

Leu Pro Ser Gln Tyr Ile Thr Gly Leu Ala Glu His Leu Ser Pro Leu
            435                 440                 445

Met Leu Ser Thr Ser Trp Thr Arg Ile Thr Leu Trp Asn Arg Asp Leu
        450                 455                 460

Ala Pro Thr Pro Gly Ala Asn Leu Tyr Gly Ser His Pro Phe Tyr Leu
465                 470                 475                 480

Ala Leu Glu Asp Gly Gly Ser Ala His Gly Val Phe Leu Leu Asn Ser
                485                 490                 495

Asn Ala Met Asp Val Val Leu Gln Pro Ser Pro Ala Leu Ser Trp Arg
                500                 505                 510
```

```
Ser Thr Gly Gly Ile Leu Asp Val Tyr Ile Phe Leu Gly Pro Glu Pro
            515                 520                 525

Lys Ser Val Val Gln Gln Tyr Leu Asp Val Val Gly Tyr Pro Phe Met
        530                 535                 540

Pro Pro Tyr Trp Gly Leu Gly Phe His Leu Cys Arg Trp Gly Tyr Ser
545                 550                 555                 560

Ser Thr Ala Ile Thr Arg Gln Val Val Glu Asn Met Thr Arg Ala His
                565                 570                 575

Phe Pro Leu Asp Val Gln Trp Asn Asp Leu Asp Tyr Met Asp Ser Arg
            580                 585                 590

Arg Asp Phe Thr Phe Asn Lys Asp Gly Phe Arg Asp Phe Pro Ala Met
        595                 600                 605

Val Gln Glu Leu His Gln Gly Arg Arg Tyr Met Met Ile Val Asp
        610                 615                 620

Pro Ala Ile Ser Ser Ser Gly Pro Ala Gly Ser Tyr Arg Pro Tyr Asp
625                 630                 635                 640

Glu Gly Leu Arg Arg Gly Val Phe Ile Thr Asn Glu Thr Gly Gln Pro
                645                 650                 655

Leu Ile Gly Lys Val Trp Pro Gly Ser Thr Ala Phe Pro Asp Phe Thr
            660                 665                 670

Asn Pro Thr Ala Leu Ala Trp Trp Glu Asp Met Val Ala Glu Phe His
        675                 680                 685

Asp Gln Val Pro Phe Asp Gly Met Trp Ile Asp Met Asn Glu Pro Ser
    690                 695                 700

Asn Phe Ile Arg Gly Ser Glu Asp Gly Cys Pro Asn Asn Glu Leu Glu
705                 710                 715                 720

Asn Pro Pro Tyr Val Pro Gly Val Val Gly Gly Thr Leu Gln Ala Ala
                725                 730                 735

Thr Ile Cys Ala Ser Ser His Gln Phe Leu Ser Thr His Tyr Asn Leu
            740                 745                 750

His Asn Leu Tyr Gly Leu Thr Glu Ala Ile Ala Ser His Arg Ala Leu
        755                 760                 765

Val Lys Ala Arg Gly Thr Arg Pro Phe Val Ile Ser Arg Ser Thr Phe
    770                 775                 780

Ala Gly His Gly Arg Tyr Ala Gly His Trp Thr Gly Asp Val Trp Ser
785                 790                 795                 800

Ser Trp Glu Gln Leu Ala Ser Ser Val Pro Glu Ile Leu Gln Phe Asn
                805                 810                 815

Leu Leu Gly Val Pro Leu Val Gly Ala Asp Val Cys Gly Phe Leu Gly
            820                 825                 830

Asn Thr Ser Glu Glu Leu Cys Val Arg Trp Thr Gln Leu Gly Ala Phe
        835                 840                 845

Tyr Pro Phe Met Arg Asn His Asn Ser Leu Leu Ser Leu Pro Gln Glu
    850                 855                 860

Pro Tyr Ser Phe Ser Glu Pro Ala Gln Gln Ala Met Arg Lys Ala Leu
865                 870                 875                 880

Thr Leu Arg Tyr Ala Leu Leu Pro His Leu Tyr Thr Leu Phe His Gln
                885                 890                 895

Ala His Val Ala Gly Glu Thr Val Ala Arg Pro Leu Phe Leu Glu Phe
            900                 905                 910

Pro Lys Asp Ser Ser Thr Trp Thr Val Asp His Gln Leu Leu Trp Gly
        915                 920                 925
```

```
Glu Ala Leu Leu Ile Thr Pro Val Leu Gln Ala Gly Lys Ala Glu Val
            930                 935                 940

Thr Gly Tyr Phe Pro Leu Gly Thr Trp Tyr Asp Leu Gln Thr Val Pro
945                 950                 955                 960

Val Glu Ala Leu Gly Ser Leu Pro Pro Pro Ala Ala Pro Arg Glu
                965                 970                 975

Pro Ala Ile His Ser Glu Gly Gln Trp Val Thr Leu Pro Ala Pro Leu
                980                 985                 990

Asp Thr Ile Asn Val His Leu Arg Ala Gly Tyr Ile Ile Pro Leu Gln
            995                 1000                1005

Gly Pro Gly Leu Thr Thr Thr Glu Ser Arg Gln Gln Pro Met Ala
    1010                1015                1020

Leu Ala Val Ala Leu Thr Lys Gly Gly Glu Ala Arg Gly Glu Leu
    1025                1030                1035

Phe Trp Asp Asp Gly Glu Ser Leu Glu Val Leu Glu Arg Gly Ala
    1040                1045                1050

Tyr Thr Gln Val Ile Phe Leu Ala Arg Asn Asn Thr Ile Val Asn
    1055                1060                1065

Glu Leu Val Arg Val Thr Ser Glu Gly Ala Gly Leu Gln Leu Gln
    1070                1075                1080

Lys Val Thr Val Leu Gly Val Ala Thr Ala Pro Gln Gln Val Leu
    1085                1090                1095

Ser Asn Gly Val Pro Val Ser Asn Phe Thr Tyr Ser Pro Asp Thr
    1100                1105                1110

Lys Val Leu Asp Ile Cys Val Ser Leu Leu Met Gly Glu Gln Phe
    1115                1120                1125

Leu Val Ser Trp Cys
    1130

<210> SEQ ID NO 11
<211> LENGTH: 3489
<212> TYPE: DNA
<213> ORGANISM: Artificial
<220> FEATURE:
<223> OTHER INFORMATION: synthetic

<400> SEQUENCE: 11
atgcacagac ctagacgtcg tggaactcgt ccacctccac tggcactgct cgctgctctc      60
ctcctggctg cacgtggtgc tgatgcagaa gtgaagctgg tggagtctgg gggaggctta     120
gtgcagcctg agggtccct gaaactctcc tgtgcaacct ctggattcac tttcagtgac     180
tattacatgt cttgggttcg ccagactcca gagaagaggc tggagtgggt cgcatatatt     240
agtagtagtg gtggtagcac ctattattca gacactgtaa agggccaatt caccatctcc     300
agagacaatg ccaagaacac cctgtacctg caaatgagcc gtctgaagtc tgaggacaca     360
gccatgtatt actgtgcaag acgagaagat tacgacggaa gacttactta ctggggccaa     420
gggactctgg tcaccatctc tgcaggagga agtggtggag gcgggtcagg aggtggcggg     480
agcggcggtg acattgtgct gacacagtct cctgcttcct agctgtatc tctgggcag     540 agggccacca tctcctgcag ggccagcaaa agtgtcagta catctggtta tagttatatg     600
aactggtacc aacagaaacc aggacagcca cccaaagtcc tcatctatct tgcatccaaa     660
ctagaatctg ggtccctgc caggttcagt ggcagtgggt cagggacaga cttcaccctc     720
aacatccatc ctgtgagga ggaggatgct gcaacctatt actgtcagca cagtagggag     780
cttccgtaca cgttcggagg ggggaccaaa ctggaaataa aaggtggtgg cggttcagca     840
```

```
caccccggcc gtcccagagc agtgcccaca cagtgcgacg tcccccccaa cagccgcttc    900
gattgcgccc ctgacaaggc catcacccag gaacagtgcg aggcccgcgg ctgttgctac    960
atccctgcaa agcagggggct gcagggagcc cagatggggc agccctggtg cttcttccca   1020
cccagctacc ccagctacaa gctggagaac ctgagctcct ctgaaatggg ctacacggcc   1080
accctgaccc gtaccacccc caccttcttc cccaaggaca tcctgaccct gcggctggac   1140
gtgatgatgg agactgagaa ccgcctccac ttcacgatca agatccagc taacaggcgc    1200
tacgaggtgc ccttggagac cccgcatgtc cacagccggg caccgtcccc actctacagc   1260
gtggagttct ccgaggagcc cttcggggtg atcgtgcgcc ggcagctgga cggccgcgtg   1320
ctgctgaaca cgacggtggc gcccctgttc tttgcggacc agttccttca gctgtccacc   1380
tcgctgccct cgcagtatat cacaggcctc gccgagcacc tcagtcccct gatgctcagc   1440
accagctgga ccaggatcac cctgtggaac cgggaccttg cgccacgcc cggtgcgaac    1500
ctctacgggt ctcacccttt ctacctggcg ctggaggacg gcgggtcggc cacggggtg    1560
ttcctgctaa acagcaatgc catggatgtg gtcctgcagc cgagccctgc ccttagctgg   1620
aggtcgacag gtgggatcct ggatgtctac atcttcctgg gcccagagcc caagagcgtg   1680
gtgcagcagt acctggacgt tgtgggatac ccgttcatgc cgccatactg gggcctgggc   1740
ttccacctgt gccgctgggg ctactcctcc accgctatca cccgccaggt ggtggagaac   1800
atgaccaggg cccacttccc cctggacgtc cagtggaacg acctggacta catggactcc   1860
cggagggact tcacgttcaa caaggatggc ttccgggact cccgggccat ggtgcaggag   1920
ctgcaccagg gcggccggcg ctacatgatg atcgtggatc ctgccatcag cagctcgggc   1980
cctgccggga gctacaggcc ctacgacgag ggtctgcgga gggggttttt catcaccaac   2040
gagaccggcc agccgctgat tgggaaggta tggcccgggt ccactgcctt ccccgacttc   2100
accaaccccca cagccctggc ctggtgggag acatggtgg ctgagttcca tgaccaggtg    2160
cccttcgacg gcatgtggat tgacatgaac gagccttcca acttcatcag gggctctgag   2220
gacggctgcc ccaacaatga gctggagaac ccaccctacg tgcctggggt ggttggggg    2280
accctccagg cggccaccat ctgtgcctcc agcaccagt ttctctccac acactacaac    2340
ctgcacaacc tctacggcct gaccgaagcc atcgcctccc acagggcgct ggtgaaggct   2400
cgggggacac gcccatttgt gatctcccgc tcgacctttg ctggccacgg ccgatacgcc   2460
ggccactgga cggggggacgt gtggagctcc tgggagcagc tcgcctcctc cgtgccagaa   2520
atcctgcagt ttaacctgct gggggtgcct ctggtcgggg ccgacgtctg cggcttcctg   2580
ggcaacacct cagaggagct gtgtgtgcgc tggaccccagc tgggggcctt ctaccccttc   2640
atgcggaacaa acaacagcct gctcagtctg ccccaggagc cgtacagctt cagcgagccg   2700
gcccagcagg ccatgaggaa ggccctcacc ctgcgctacg cactcctccc ccacctctac   2760
acactgttcc accaggccca cgtcgcgggg gagaccgtgg cccggcccct cttcctggag   2820
ttccccaagg actctagcac ctggactgtg gaccaccagc tcctgtgggg ggaggccctg   2880
ctcatcaccc cagtgctcca ggccgggaag gccgaagtga ctggctactt ccccttgggc   2940
acatggtacg acctgcagac ggtgccagta gaggcccttg gcagcctccc accccacct   3000
gcagctcccc gtgagccagc catccacagc gaggggcagt gggtgacgct gccggccccc   3060
ctggacacca tcaacgtcca cctccggggct gggtacatca tcccccctgca gggccctggc   3120
ctcacaacca cagagtcccg ccagcagccc atggccctgg ctgtggccct gaccaagggt   3180
```

| | |
|---|---|
| ggggaggccc gaggggagct gttctgggac gatggagaga gcctggaagt gctggagcga | 3240 |
| ggggcctaca cacaggtcat cttcctggcc aggaataaca cgatcgtgaa tgagctggta | 3300 |
| cgtgtgacca gtgagggagc tggcctgcag ctgcagaagg tgactgtcct gggcgtggcc | 3360 |
| acggcgcccc agcaggtcct ctccaacggt gtccctgtct ccaacttcac ctacagcccc | 3420 |
| gacaccaagg tcctggacat ctgtgtctcg ctgttgatgg gagagcagtt tctcgtcagc | 3480 |
| tggtgttag | 3489 |

<210> SEQ ID NO 12
<211> LENGTH: 2859
<212> TYPE: DNA
<213> ORGANISM: Homo sapiens

<400> SEQUENCE: 12

| | |
|---|---|
| atgggagtga ggcacccgcc ctgctcccac cggctcctgg ccgtctgcgc cctcgtgtcc | 60 |
| ttggcaaccg ctgcactcct ggggcacatc ctactccatg atttcctgct ggttccccga | 120 |
| gagctgagtg gctcctcccc agtcctggag gagactcacc cagctcacca gcagggagcc | 180 |
| agcagaccag gcccccggga tgcccaggca caccccggcc gtcccagagc agtgcccaca | 240 |
| cagtgcgacg tccccccaa cagccgcttc gattgcgccc tgacaaggc catcacccag | 300 |
| gaacagtgcg aggcccgcgg ctgttgctac atccctgcaa gcaggggct gcaggagcc | 360 |
| cagatggggc agccctggtg cttcttccca cccagctacc ccagctacaa gctggagaac | 420 |
| ctgagctcct ctgaaatggg ctacacggcc accctgaccc gtaccacccc caccttcttc | 480 |
| cccaaggaca tcctgaccct gcggctggac gtgatgatgg agactgagaa ccgcctccac | 540 |
| ttcacgatca agatccagc taacaggcgc tacgaggtgc ccttggagac ccgcatgtc | 600 |
| cacagccggg caccgtcccc actctacagc gtggagttct ccgaggagcc cttcggggtg | 660 |
| atcgtgcgcc ggcagctgga cggccgcgtg ctgctgaaca cgacggtggc gcccctgttc | 720 |
| tttgcggacc agttccttca gctgtccacc tcgctgccct cgcagtatat cacaggcctc | 780 |
| gccgagcacc tcagtcccct gatgctcagc accagctgga ccaggatcac cctgtggaac | 840 |
| cgggaccttg cgcccacgcc cggtgcgaac ctctacgggt ctcaccccttt ctacctggcg | 900 |
| ctggaggacg gcgggtcggc acacggggtg ttcctgctaa acagcaatgc catggatgtg | 960 |
| gtcctgcagc cgagccctgc ccttagctgg aggtcgacag gtgggatcct ggatgtctac | 1020 |
| atcttcctgg gccagagcc caagagcgtg gtgcagcagt acctggacgt tgtgggatac | 1080 |
| ccgttcatgc cgccatactg gggcctgggc ttccacctgt gccgctgggg ctactcctcc | 1140 |
| accgctatca cccgccaggt ggtggagaac atgaccaggg cccacttccc cctggacgtc | 1200 |
| cagtggaacg acctggacta catggactcc cggagggact tcacgttcaa caaggatggc | 1260 |
| ttccgggact cccggccat ggtgcaggag ctgcaccagg gcggccggcg ctacatgatg | 1320 |
| atcgtggatc ctgccatcag cagctcgggc cctgccggga ctacaggcc ctacgacgag | 1380 |
| ggtctgcgga gggggttttt catcaccaac gagaccggcc agccgctgat tgggaaggta | 1440 |
| tggcccgggt ccactgcctt ccccgacttc accaacccca cagccctggc ctggtgggag | 1500 |
| gacatggtgg ctgagttcca tgaccagtg cccttgacg gcatgtggat tgacatgaac | 1560 |
| gagccttcca acttcatcag gggctctgag gacggctgcc ccaacaatga gctggagaac | 1620 |
| ccacctacg tgcctggggt ggttgggggg acctccagg cggccaccat ctgtgcctcc | 1680 |
| agccaccagt ttctctccac acactacaac ctgcacaacc tctacggcct gaccgaagcc | 1740 |
| atcgcctccc acagggcgct ggtgaaggct cggggacac gcccatttgt gatctcccgc | 1800 |

-continued

```
tcgacctttg ctggccacgg ccgatacgcc ggccactgga cggggacgt gtggagctcc    1860 tgggagcagc tcgcctcctc cgtgccagaa atcctgcagt ttaacctgct gggggtgcct    1920
ctggtcgggg ccgacgtctg cggcttcctg gcaacacct cagaggagct gtgtgtgcgc    1980
tggacccagc tgggggcctt ctaccccttc atgcggaacc acaacagcct gctcagtctg    2040
ccccaggagc cgtacagctt cagcgagccg gcccagcagg ccatgaggaa ggccctcacc    2100
ctgcgctacg cactcctccc ccacctctac acactgttcc accaggccca cgtcgcgggg    2160
gagaccgtgg cccggcccct cttcctggag ttccccaagg actctagcac ctggactgtg    2220
gaccaccagc tcctgtgggg ggaggccctg ctcatcaccc cagtgctcca ggccgggaag    2280
gccgaagtga ctggctactt cccccttggggc acatggtacg acctgcagac ggtgccagta    2340
gaggcccttg gcagcctccc accccccacct gcagctcccc gtgagccagc catccacagc    2400
gaggggcagt gggtgacgct gccggcccccc ctggacacca tcaacgtcca cctccgggct    2460
gggtacatca tcccccctgca gggccctggc ctcacaacca cagagtcccg ccagcagccc    2520
atggccctgg ctgtggccct gaccaagggt ggggaggccc gagggagct gttctgggac    2580 gatggagaga gcctggaagt gctggagcga ggggcctaca cacaggtcat cttcctggcc    2640
aggaataaca cgatcgtgaa tgagctggta cgtgtgacca gtgagggagc tggcctgcag    2700
ctgcagaagg tgactgtcct gggcgtggcc acggcgcccc agcaggtcct ctccaacggt    2760
gtccctgtct ccaacttcac ctacagcccc gacaccaagg tcctggacat ctgtgtctcg    2820
ctgttgatgg gagagcagtt tctcgtcagc tggtgttag                         2859
```

<210> SEQ ID NO 13
<211> LENGTH: 354
<212> TYPE: DNA
<213> ORGANISM: Homo sapiens

<400> SEQUENCE: 13

```
caggtgcagc tgcaggagtc gggccccgga ctgatgaagc cttcggagac cctgtccctc      60
acctgcactg tctctggtgg ctccttcagc agttactatt ggaactggat ccggcagtcc     120
ccagggaagg gactggagtg gattgggtat atccgttata gtggggacac caactacaag     180
ccctccctca agagtcgatt caccatatca attgacacgt ccaagaacct tttctccctg     240
aggctgaaat ctgtgaccgc tgcggacacg gccgtgtatt actgtgcgag gatgggactg     300
gggagtgatg cttttgatat ctggggccaa gggacaatgg tcaccgtctc ttca           354
```

<210> SEQ ID NO 14
<211> LENGTH: 118
<212> TYPE: PRT
<213> ORGANISM: Homo sapiens

<400> SEQUENCE: 14

Gln Val Gln Leu Gln Glu Ser Gly Pro Gly Leu Met Lys Pro Ser Glu
1               5                   10                  15

Thr Leu Ser Leu Thr Cys Thr Val Ser Gly Gly Ser Phe Ser Ser Tyr
            20                  25                  30

Tyr Trp Asn Trp Ile Arg Gln Ser Pro Gly Lys Gly Leu Glu Trp Ile
        35                  40                  45

Gly Tyr Ile Arg Tyr Ser Gly Asp Thr Asn Tyr Lys Pro Ser Leu Lys
    50                  55                  60

Ser Arg Phe Thr Ile Ser Ile Asp Thr Ser Lys Asn Leu Phe Ser Leu
65                  70                  75                  80

```
Arg Leu Lys Ser Val Thr Ala Ala Asp Thr Ala Val Tyr Tyr Cys Ala
                85                  90                  95
Arg Met Gly Leu Gly Ser Asp Ala Phe Asp Ile Trp Gly Gln Gly Thr
            100                 105                 110
Met Val Thr Val Ser Ser
        115

<210> SEQ ID NO 15
<211> LENGTH: 24
<212> TYPE: DNA
<213> ORGANISM: Homo sapiens

<400> SEQUENCE: 15
ggtggctcct tcagcagtta ctat                                       24

<210> SEQ ID NO 16
<211> LENGTH: 8
<212> TYPE: PRT
<213> ORGANISM: Homo sapiens

<400> SEQUENCE: 16

Gly Gly Ser Phe Ser Ser Tyr Tyr
1               5

<210> SEQ ID NO 17
<211> LENGTH: 21
<212> TYPE: DNA
<213> ORGANISM: Homo sapiens

<400> SEQUENCE: 17
atccgttata gtggggacac c                                          21

<210> SEQ ID NO 18
<211> LENGTH: 7
<212> TYPE: PRT
<213> ORGANISM: Homo sapiens

<400> SEQUENCE: 18

Ile Arg Tyr Ser Gly Asp Thr
1               5

<210> SEQ ID NO 19
<211> LENGTH: 36
<212> TYPE: DNA
<213> ORGANISM: Homo sapiens

<400> SEQUENCE: 19
gcgaggatgg gactggggag tgatgctttt gatatc                          36

<210> SEQ ID NO 20
<211> LENGTH: 12
<212> TYPE: PRT
<213> ORGANISM: Homo sapiens

<400> SEQUENCE: 20

Ala Arg Met Gly Leu Gly Ser Asp Ala Phe Asp Ile
1               5                   10

<210> SEQ ID NO 21
<211> LENGTH: 324
<212> TYPE: DNA
<213> ORGANISM: Homo sapiens
```

```
<400> SEQUENCE: 21
gaaattgtgt tgacgcagtc tccaggcacc ctgtctttgt ctccagggga aagagccacc    60
ctctcctgca gggccagtca gagtgttaac aacaattatt tagcctggta ccagcagaaa   120
cctggccagg ctcccaggct cctcatctat ggtgtattca acagggccac taacatccca   180
gacaggttca gtggcagtgg gtctgggaca gatttcactc tcaccatcag cagactggag   240
cctgaagatt ttgcagtgta ttactgtcag cagtatggta gttcaccttg gacgttcggc   300
caagggacca aggtggaaat caaa                                          324

<210> SEQ ID NO 22
<211> LENGTH: 108
<212> TYPE: PRT
<213> ORGANISM: Homo sapiens

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asn Asn Asn
            20                  25                  30

Tyr Leu Ala Trp Tyr Gln Gln Lys Pro Gly Gln Ala Pro Arg Leu Leu
        35                  40                  45

Ile Tyr Gly Val Phe Asn Arg Ala Thr Asn Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 23
<211> LENGTH: 21
<212> TYPE: DNA
<213> ORGANISM: Homo sapiens

<400> SEQUENCE: 23
cagagtgtta acaacaatta t                                              21

<210> SEQ ID NO 24
<211> LENGTH: 7
<212> TYPE: PRT
<213> ORGANISM: Homo sapiens

<400> SEQUENCE: 24

Gln Ser Val Asn Asn Asn Tyr
1               5

<210> SEQ ID NO 25
<211> LENGTH: 9
<212> TYPE: DNA
<213> ORGANISM: Homo sapiens

<400> SEQUENCE: 25 ggtgtattc                                                             9

<210> SEQ ID NO 26
<211> LENGTH: 3
<212> TYPE: PRT
<213> ORGANISM: Homo sapiens
```

<400> SEQUENCE: 26

Gly Val Phe
1

<210> SEQ ID NO 27
<211> LENGTH: 27
<212> TYPE: DNA
<213> ORGANISM: Homo sapiens

<400> SEQUENCE: 27
cagcagtatg gtagttcacc ttggacg                                27

<210> SEQ ID NO 28
<211> LENGTH: 9
<212> TYPE: PRT
<213> ORGANISM: Homo sapiens

<400> SEQUENCE: 28

Gln Gln Tyr Gly Ser Ser Pro Trp Thr
1               5

<210> SEQ ID NO 29
<211> LENGTH: 354
<212> TYPE: DNA
<213> ORGANISM: Homo sapiens

<400> SEQUENCE: 29
caggtgcagc tgcaggagtc gggcccaaga ctggtgaagc cttcggagac cctgtccctc      60
acctgcattg tctctggtgg ctccatcagt aatttctact ggaactggat ccggcagtcc     120
ccagggaagg gactggaatg gattggatat ttcttttaca ctgggactat cgactacaac     180
ccctccctca agagtcgagt caccatatca ctggacacgt ccaagaacca gttctccctg     240
aacctgcgtc tcctgaccgc cgcagacgcg gccgtttatt attgtgcgag gatggggctg     300
ggggctaatg cttttgacat ctggggccac gggacaatgg tcaccgtctc ttca          354

<210> SEQ ID NO 30
<211> LENGTH: 118
<212> TYPE: PRT
<213> ORGANISM: Homo sapiens

<400> SEQUENCE: 30

Gln Val Gln Leu Gln Glu Ser Gly Pro Arg Leu Val Lys Pro Ser Glu
1               5                   10                  15

Thr Leu Ser Leu Thr Cys Ile Val Ser Gly Gly Ser Ile Ser Asn Phe
            20                  25                  30

Tyr Trp Asn Trp Ile Arg Gln Ser Pro Gly Lys Gly Leu Glu Trp Ile
        35                  40                  45

Gly Tyr Phe Phe Tyr Thr Gly Thr Ile Asp Tyr Asn Pro Ser Leu Lys
    50                  55                  60

Ser Arg Val Thr Ile Ser Leu Asp Thr Ser Lys Asn Gln Phe Ser Leu
65                  70                  75                  80

Asn Leu Arg Leu Leu Thr Ala Ala Asp Ala Ala Val Tyr Tyr Cys Ala
                85                  90                  95

Arg Met Gly Leu Gly Ala Asn Ala Phe Asp Ile Trp Gly His Gly Thr
            100                 105                 110

Met Val Thr Val Ser Ser
        115

<210> SEQ ID NO 31
<211> LENGTH: 24
<212> TYPE: DNA
<213> ORGANISM: Homo sapiens

<400> SEQUENCE: 31
ggtggctcca tcagtaattt ctac                                              24

<210> SEQ ID NO 32
<211> LENGTH: 8
<212> TYPE: PRT
<213> ORGANISM: Homo sapiens

<400> SEQUENCE: 32

Gly Gly Ser Ile Ser Asn Phe Tyr
1               5

<210> SEQ ID NO 33
<211> LENGTH: 21
<212> TYPE: DNA
<213> ORGANISM: Homo sapiens

<400> SEQUENCE: 33
ttcttttaca ctgggactat c                                                 21

<210> SEQ ID NO 34
<211> LENGTH: 7
<212> TYPE: PRT
<213> ORGANISM: Homo sapiens

<400> SEQUENCE: 34

Phe Phe Tyr Thr Gly Thr Ile
1               5

<210> SEQ ID NO 35
<211> LENGTH: 36
<212> TYPE: DNA
<213> ORGANISM: Homo sapiens

<400> SEQUENCE: 35
gcgaggatgg ggctgggggc taatgctttt gacatc                                 36

<210> SEQ ID NO 36
<211> LENGTH: 12
<212> TYPE: PRT
<213> ORGANISM: Homo sapiens

<400> SEQUENCE: 36

Ala Arg Met Gly Leu Gly Ala Asn Ala Phe Asp Ile
1               5                   10

<210> SEQ ID NO 37
<211> LENGTH: 324
<212> TYPE: DNA
<213> ORGANISM: Homo sapiens

<400> SEQUENCE: 37
gaaattgtgt tgacgcagtc tccaggcacc ctgtctttgt ctcctggaga aagagccacc       60
ctctcctgca gggccagtca gcatgttagc agcaactact tagcctggta ccagcagaaa      120
cctggccagg ctcccaggct cctcatctat ggtggatcca gcagggccac tggcatccca      180
gacaggttca gtggcagtgg gtctgggaca gacttcactc tcaccatcag cagactggag      240

```
cctgcagatt ttgcagtgtt ttactgtcag cagtatggta actcaccttg gacgttcggc    300
caagggacca aggtggaaat gaaa                                            324
```

<210> SEQ ID NO 38
<211> LENGTH: 108
<212> TYPE: PRT
<213> ORGANISM: Homo sapiens

<400> SEQUENCE: 38

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln His Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Gly Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Ala Asp Phe Ala Val Phe Tyr Cys Gln Gln Tyr Gly Asn Ser Pro
                85                  90                  95

Trp Thr Phe Gly Gln Gly Thr Lys Val Glu Met Lys
            100                 105
```

<210> SEQ ID NO 39
<211> LENGTH: 21
<212> TYPE: DNA
<213> ORGANISM: Homo sapiens

<400> SEQUENCE: 39

```
cagcatgtta gcagcaacta c                                               21
```

<210> SEQ ID NO 40
<211> LENGTH: 7
<212> TYPE: PRT
<213> ORGANISM: Homo sapiens

<400> SEQUENCE: 40

```
Gln His Val Ser Ser Asn Tyr
1               5
```

<210> SEQ ID NO 41
<211> LENGTH: 9
<212> TYPE: DNA
<213> ORGANISM: Homo sapiens

<400> SEQUENCE: 41

```
ggtggatcc                                                              9
```

<210> SEQ ID NO 42
<211> LENGTH: 3
<212> TYPE: PRT
<213> ORGANISM: Homo sapiens

<400> SEQUENCE: 42

```
Gly Gly Ser
1
```

<210> SEQ ID NO 43
<211> LENGTH: 27
<212> TYPE: DNA

<213> ORGANISM: Homo sapiens

<400> SEQUENCE: 43
cagcagtatg gtaactcacc ttggacg                                                27

<210> SEQ ID NO 44
<211> LENGTH: 9
<212> TYPE: PRT
<213> ORGANISM: Homo sapiens

<400> SEQUENCE: 44

Gln Gln Tyr Gly Asn Ser Pro Trp Thr
1               5

<210> SEQ ID NO 45
<211> LENGTH: 351
<212> TYPE: DNA
<213> ORGANISM: Homo sapiens

<400> SEQUENCE: 45
caggtgcaac tacaggagtc gggcccaaag gtggtgaagc cttcggagac cctgtccctc      60
acctgcactg tctctggtgg ctccatcagt agttactact ggaattggat ccgccagtcc     120
ccagggaagg gactggagtg gattggatat accaaaagag gtataccga ctacaacccc      180 tccctcagga gtcgcgtcac tatatcagaa gacacgtcca agaaccagtt ctccctgagg     240
atcagctctg tgaccgccgc agacacggcc gtatattact gtgcacaaat ggggtgggga    300
tcccatgctt ttgacatgtg gggccaaggg acaatggtcg ccgtctcttc a             351

<210> SEQ ID NO 46
<211> LENGTH: 117
<212> TYPE: PRT
<213> ORGANISM: Homo sapiens

<400> SEQUENCE: 46

Gln Val Gln Leu Gln Glu Ser Gly Pro Lys Val Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Asn Trp Ile Arg Gln Ser Pro Gly Lys Gly Leu Glu Trp Ile
        35                  40                  45

Gly Tyr Thr Lys Arg Gly Tyr Thr Asp Tyr Asn Pro Ser Leu Arg Ser
    50                  55                  60

Arg Val Thr Ile Ser Glu Asp Thr Ser Lys Asn Gln Phe Ser Leu Arg
65                  70                  75                  80

Ile Ser Ser Val Thr Ala Ala Asp Thr Ala Val Tyr Tyr Cys Ala Gln
                85                  90                  95

Met Gly Trp Gly Ser His Ala Phe Asp Met Trp Gly Gln Gly Thr Met
            100                 105                 110

Val Ala Val Ser Ser
        115

<210> SEQ ID NO 47
<211> LENGTH: 24
<212> TYPE: DNA
<213> ORGANISM: Homo sapiens

<400> SEQUENCE: 47
ggtggctcca tcagtagtta ctac                                              24

<210> SEQ ID NO 48
<211> LENGTH: 8
<212> TYPE: PRT
<213> ORGANISM: Homo sapiens

<400> SEQUENCE: 48

Gly Gly Ser Ile Ser Ser Tyr Tyr
1               5

<210> SEQ ID NO 49
<211> LENGTH: 18
<212> TYPE: DNA
<213> ORGANISM: Homo sapiens

<400> SEQUENCE: 49
accaaaagag ggtatacc                                                    18

<210> SEQ ID NO 50
<211> LENGTH: 6
<212> TYPE: PRT
<213> ORGANISM: Homo sapiens

<400> SEQUENCE: 50

Thr Lys Arg Gly Tyr Thr
1               5

<210> SEQ ID NO 51
<211> LENGTH: 36
<212> TYPE: DNA
<213> ORGANISM: Homo sapiens

<400> SEQUENCE: 51
gcacaaatgg ggtggggatc ccatgctttt gacatg                                36

<210> SEQ ID NO 52
<211> LENGTH: 12
<212> TYPE: PRT
<213> ORGANISM: Homo sapiens

<400> SEQUENCE: 52

Ala Gln Met Gly Trp Gly Ser His Ala Phe Asp Met
1               5                   10

<210> SEQ ID NO 53
<211> LENGTH: 324
<212> TYPE: DNA
<213> ORGANISM: Homo sapiens

<400> SEQUENCE: 53
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccttg gacgttcggc     300
caagggacca aggtggaaat caaa                                            324

<210> SEQ ID NO 54
<211> LENGTH: 108
<212> TYPE: PRT
<213> ORGANISM: Homo sapiens

<400> SEQUENCE: 54

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Pro
                85                  90                  95

Trp Thr Phe Gly Gln Gly Thr Lys Val Glu Ile Lys
            100                 105

<210> SEQ ID NO 55
<211> LENGTH: 21
<212> TYPE: DNA
<213> ORGANISM: Homo sapiens

<400> SEQUENCE: 55
cagagtgtta gcagcagcta c                                           21

<210> SEQ ID NO 56
<211> LENGTH: 7
<212> TYPE: PRT
<213> ORGANISM: Homo sapiens

<400> SEQUENCE: 56

Gln Ser Val Ser Ser Ser Tyr
1               5

<210> SEQ ID NO 57
<211> LENGTH: 9
<212> TYPE: DNA
<213> ORGANISM: Homo sapiens

<400> SEQUENCE: 57 ggtgcatcc                                                          9

<210> SEQ ID NO 58
<211> LENGTH: 3
<212> TYPE: PRT
<213> ORGANISM: Homo sapiens

<400> SEQUENCE: 58

Gly Ala Ser
1

<210> SEQ ID NO 59
<211> LENGTH: 27
<212> TYPE: DNA
<213> ORGANISM: Homo sapiens

<400> SEQUENCE: 59
cagcagtatg gtagctcacc ttggacg                                     27

<210> SEQ ID NO 60
<211> LENGTH: 9
<212> TYPE: PRT

<213> ORGANISM: Homo sapiens

<400> SEQUENCE: 60

Gln Gln Tyr Gly Ser Ser Pro Trp Thr
1               5

<210> SEQ ID NO 61
<211> LENGTH: 351
<212> TYPE: DNA
<213> ORGANISM: Homo sapiens

<400> SEQUENCE: 61
caggtgcaac tacaggagtc gggcccaaag gtggtgaagc cttcggagac cctgtccctc     60
acctgcactg tctctggtgg ctccatcagt agttactact ggaattggat ccgccagtcc    120
ccagggaagg gactggagtg gattggatat accaaaagag gtataccga ctacaacccc    180
tccctcagga gtcgcgtcac tatatcagaa gacacgtcca agaaccagtt ctccctgagg    240
atcagctctg tgaccgccgc agacacggcc gtatattact gtgcacaaat ggggtgggga    300
tcccatgctt ttgacatgtg gggccaaggg acaatggtcg ccgtctcttc a             351

<210> SEQ ID NO 62
<211> LENGTH: 117
<212> TYPE: PRT
<213> ORGANISM: Homo sapiens

<400> SEQUENCE: 62

Gln Val Gln Leu Gln Glu Ser Gly Pro Lys Val Val Lys Pro Ser Glu
1               5                   10                  15
Thr Leu Ser Leu Thr Cys Thr Val Ser Gly Gly Ser Ile Ser Ser Tyr
                20                  25                  30
Tyr Trp Asn Trp Ile Arg Gln Ser Pro Gly Lys Gly Leu Glu Trp Ile
            35                  40                  45
Gly Tyr Thr Lys Arg Gly Tyr Thr Asp Tyr Asn Pro Ser Leu Arg Ser
        50                  55                  60
Arg Val Thr Ile Ser Glu Asp Thr Ser Lys Asn Gln Phe Ser Leu Arg
65                  70                  75                  80
Ile Ser Ser Val Thr Ala Ala Asp Thr Ala Val Tyr Tyr Cys Ala Gln
                85                  90                  95
Met Gly Trp Gly Ser His Ala Phe Asp Met Trp Gly Gln Gly Thr Met
            100                 105                 110
Val Ala Val Ser Ser
        115

<210> SEQ ID NO 63
<211> LENGTH: 24
<212> TYPE: DNA
<213> ORGANISM: Homo sapiens

<400> SEQUENCE: 63
ggtggctcca tcagtagtta ctac                                            24

<210> SEQ ID NO 64
<211> LENGTH: 8
<212> TYPE: PRT
<213> ORGANISM: Homo sapiens

<400> SEQUENCE: 64

Gly Gly Ser Ile Ser Ser Tyr Tyr
1               5

```
<210> SEQ ID NO 65
<211> LENGTH: 18
<212> TYPE: DNA
<213> ORGANISM: Homo sapiens

<400> SEQUENCE: 65
accaaaagag ggtatacc                                                   18

<210> SEQ ID NO 66
<211> LENGTH: 6
<212> TYPE: PRT
<213> ORGANISM: Homo sapiens

<400> SEQUENCE: 66

Thr Lys Arg Gly Tyr Thr
1               5

<210> SEQ ID NO 67
<211> LENGTH: 36
<212> TYPE: DNA
<213> ORGANISM: Homo sapiens

<400> SEQUENCE: 67
gcacaaatgg ggtggggatc ccatgctttt gacatg                               36

<210> SEQ ID NO 68
<211> LENGTH: 12
<212> TYPE: PRT
<213> ORGANISM: Homo sapiens

<400> SEQUENCE: 68

Ala Gln Met Gly Trp Gly Ser His Ala Phe Asp Met
1               5                   10

<210> SEQ ID NO 69
<211> LENGTH: 324
<212> TYPE: DNA
<213> ORGANISM: Homo sapiens

<400> SEQUENCE: 69
gaaattgtgt tgacgcagtc tccaggcacc ctgtctttgt ctccagggga aagagccacc     60
ctctcctgca gggccagtca gagtgttaat agtaggtact tagcctggta ccagcagaaa    120
cctggccagg ctcccaggct cctcatctat ggtgcatcca gcagggccac tggcatccca    180
gacaggtgca gtggcagtgg gtccgggaca gacttcactc tcaccatcag cagactggag    240
cctgaagatt ttgcagtgta ttactgtcag cagtatggta gctcaccttg gacgttcggc    300
caggggacca aggtggaaat caaa                                           324

<210> SEQ ID NO 70
<211> LENGTH: 108
<212> TYPE: PRT
<213> ORGANISM: Homo sapiens

<400> SEQUENCE: 70

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asn Ser Arg
            20                  25                  30

Tyr Leu Ala Trp Tyr Gln Gln Lys Pro Gly Gln Ala Pro Arg Leu Leu
        35                  40                  45
```

Ile Tyr Gly Ala Ser Ser Arg Ala Thr Gly Ile Pro Asp Arg Cys Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
            100                 105

<210> SEQ ID NO 71
<211> LENGTH: 21
<212> TYPE: DNA
<213> ORGANISM: Homo sapiens

<400> SEQUENCE: 71
cagagtgtta atagtaggta c                                              21

<210> SEQ ID NO 72
<211> LENGTH: 7
<212> TYPE: PRT
<213> ORGANISM: Homo sapiens

<400> SEQUENCE: 72

Gln Ser Val Asn Ser Arg Tyr
1               5

<210> SEQ ID NO 73
<211> LENGTH: 9
<212> TYPE: DNA
<213> ORGANISM: Homo sapiens

<400> SEQUENCE: 73 ggtgcatcc                                                             9

<210> SEQ ID NO 74
<211> LENGTH: 3
<212> TYPE: PRT
<213> ORGANISM: Homo sapiens

<400> SEQUENCE: 74

Gly Ala Ser
1

<210> SEQ ID NO 75
<211> LENGTH: 27
<212> TYPE: DNA
<213> ORGANISM: Homo sapiens

<400> SEQUENCE: 75
cagcagtatg gtagctcacc ttggacg                                        27

<210> SEQ ID NO 76
<211> LENGTH: 9
<212> TYPE: PRT
<213> ORGANISM: Homo sapiens

<400> SEQUENCE: 76

Gln Gln Tyr Gly Ser Ser Pro Trp Thr
1               5

<210> SEQ ID NO 77
<211> LENGTH: 238

<212> TYPE: PRT
<213> ORGANISM: Homo sapiens

<400> SEQUENCE: 77

```
Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Ile Asn Val Thr Val Gly
                165                 170                 175

Cys Gly Ile Asn Phe Asn Glu Lys Ala Ile His Lys Glu Gly Cys Val
            180                 185                 190

Glu Lys Ile Gly Gly Trp Leu Arg Lys Asn Val Leu Val Val Ala Ala
        195                 200                 205

Ala Ala Leu Gly Ile Ala Phe Val Glu Val Leu Gly Ile Val Phe Ala
    210                 215                 220

Cys Cys Leu Val Lys Ser Ile Arg Ser Gly Tyr Glu Val Met
225                 230                 235
```

<210> SEQ ID NO 78
<211> LENGTH: 917
<212> TYPE: PRT
<213> ORGANISM: Homo sapiens

<400> SEQUENCE: 78

```
Leu Leu Val Pro Arg Glu Leu Ser Gly Ser Pro Val Leu Glu Glu
1               5                   10                  15

Thr His Pro Ala His Gln Gln Gly Ala Ser Arg Pro Gly Pro Arg Asp
            20                  25                  30

Ala Gln Ala His Pro Gly Arg Pro Arg Ala Val Pro Thr Gln Cys Asp
        35                  40                  45

Val Pro Pro Asn Ser Arg Phe Asp Cys Ala Pro Asp Lys Ala Ile Thr
    50                  55                  60

Gln Glu Gln Cys Glu Ala Arg Gly Cys Cys Tyr Ile Pro Ala Lys Gln
65                  70                  75                  80

Gly Leu Gln Gly Ala Gln Met Gly Gln Pro Trp Cys Phe Phe Pro Pro
                85                  90                  95

Ser Tyr Pro Ser Tyr Lys Leu Glu Asn Leu Ser Ser Ser Glu Met Gly
            100                 105                 110
```

```
Tyr Thr Ala Thr Leu Thr Arg Thr Pro Thr Phe Phe Pro Lys Asp
        115                 120                 125

Ile Leu Thr Leu Arg Leu Asp Val Met Met Glu Thr Glu Asn Arg Leu
    130                 135                 140

His Phe Thr Ile Lys Asp Pro Ala Asn Arg Arg Tyr Glu Val Pro Leu
145                 150                 155                 160

Glu Thr Pro His Val His Ser Arg Ala Pro Ser Pro Leu Tyr Ser Val
                165                 170                 175

Glu Phe Ser Glu Pro Phe Gly Val Ile Val Arg Arg Gln Leu Asp
            180                 185                 190

Gly Arg Val Leu Leu Asn Thr Thr Val Ala Pro Leu Phe Phe Ala Asp
        195                 200                 205

Gln Phe Leu Gln Leu Ser Thr Ser Leu Pro Ser Gln Tyr Ile Thr Gly
    210                 215                 220

Leu Ala Glu His Leu Ser Pro Leu Met Leu Ser Thr Ser Trp Thr Arg
225                 230                 235                 240

Ile Thr Leu Trp Asn Arg Asp Leu Ala Pro Thr Pro Gly Ala Asn Leu
                245                 250                 255

Tyr Gly Ser His Pro Phe Tyr Leu Ala Leu Glu Asp Gly Gly Ser Ala
            260                 265                 270

His Gly Val Phe Leu Leu Asn Ser Asn Ala Met Asp Val Val Leu Gln
        275                 280                 285

Pro Ser Pro Ala Leu Ser Trp Arg Ser Thr Gly Gly Ile Leu Asp Val
    290                 295                 300

Tyr Ile Phe Leu Gly Pro Glu Pro Lys Ser Val Val Gln Gln Tyr Leu
305                 310                 315                 320

Asp Val Val Gly Tyr Pro Phe Met Pro Pro Tyr Trp Gly Leu Gly Phe
                325                 330                 335

His Leu Cys Arg Trp Gly Tyr Ser Ser Thr Ala Ile Thr Arg Gln Val
            340                 345                 350

Val Glu Asn Met Thr Arg Ala His Phe Pro Leu Asp Val Gln Trp Asn
        355                 360                 365

Asp Leu Asp Tyr Met Asp Ser Arg Arg Asp Phe Thr Phe Asn Lys Asp
    370                 375                 380

Gly Phe Arg Asp Phe Pro Ala Met Val Gln Glu Leu His Gln Gly Gly
385                 390                 395                 400

Arg Arg Tyr Met Met Ile Val Asp Pro Ala Ile Ser Ser Ser Gly Pro
                405                 410                 415

Ala Gly Ser Tyr Arg Pro Tyr Asp Glu Gly Leu Arg Arg Gly Val Phe
            420                 425                 430

Ile Thr Asn Glu Thr Gly Gln Pro Leu Ile Gly Lys Val Trp Pro Gly
        435                 440                 445

Ser Thr Ala Phe Pro Asp Phe Thr Asn Pro Thr Ala Leu Ala Trp Trp
    450                 455                 460

Glu Asp Met Val Ala Glu Phe His Asp Gln Val Pro Phe Asp Gly Met
465                 470                 475                 480

Trp Ile Asp Met Asn Glu Pro Ser Asn Phe Ile Arg Gly Ser Glu Asp
                485                 490                 495

Gly Cys Pro Asn Asn Glu Leu Glu Asn Pro Pro Tyr Val Pro Gly Val
            500                 505                 510

Val Gly Gly Thr Leu Gln Ala Ala Thr Ile Cys Ala Ser Ser His Gln
        515                 520                 525

Phe Leu Ser Thr His Tyr Asn Leu His Asn Leu Tyr Gly Leu Thr Glu
```

```
            530                 535                 540
Ala Ile Ala Ser His Arg Ala Leu Val Lys Ala Arg Gly Thr Arg Pro
545                 550                 555                 560

Phe Val Ile Ser Arg Ser Thr Phe Ala Gly His Gly Arg Tyr Ala Gly
                565                 570                 575

His Trp Thr Gly Asp Val Trp Ser Ser Trp Glu Gln Leu Ala Ser Ser
            580                 585                 590

Val Pro Glu Ile Leu Gln Phe Asn Leu Leu Gly Val Pro Leu Val Gly
        595                 600                 605

Ala Asp Val Cys Gly Phe Leu Gly Asn Thr Ser Glu Glu Leu Cys Val
    610                 615                 620

Arg Trp Thr Gln Leu Gly Ala Phe Tyr Pro Phe Met Arg Asn His Asn
625                 630                 635                 640

Ser Leu Leu Ser Leu Pro Gln Glu Pro Tyr Ser Phe Ser Glu Pro Ala
                645                 650                 655

Gln Gln Ala Met Arg Lys Ala Leu Thr Leu Arg Tyr Ala Leu Leu Pro
            660                 665                 670

His Leu Tyr Thr Leu Phe His Gln Ala His Val Ala Gly Glu Thr Val
        675                 680                 685

Ala Arg Pro Leu Phe Leu Glu Phe Pro Lys Asp Ser Ser Thr Trp Thr
    690                 695                 700

Val Asp His Gln Leu Leu Trp Gly Glu Ala Leu Leu Ile Thr Pro Val
705                 710                 715                 720

Leu Gln Ala Gly Lys Ala Glu Val Thr Gly Tyr Phe Pro Leu Gly Thr
                725                 730                 735

Trp Tyr Asp Leu Gln Thr Val Pro Val Glu Ala Leu Gly Ser Leu Pro
            740                 745                 750

Pro Pro Pro Ala Ala Pro Arg Glu Pro Ala Ile His Ser Glu Gly Gln
        755                 760                 765

Trp Val Thr Leu Pro Ala Pro Leu Asp Thr Ile Asn Val His Leu Arg
    770                 775                 780

Ala Gly Tyr Ile Ile Pro Leu Gln Gly Pro Gly Leu Thr Thr Thr Glu
785                 790                 795                 800

Ser Arg Gln Gln Pro Met Ala Leu Ala Val Ala Leu Thr Lys Gly Gly
                805                 810                 815

Glu Ala Arg Gly Glu Leu Phe Trp Asp Asp Gly Glu Ser Leu Glu Val
            820                 825                 830

Leu Glu Arg Gly Ala Tyr Thr Gln Val Ile Phe Leu Ala Arg Asn Asn
        835                 840                 845

Thr Ile Val Asn Glu Leu Val Arg Val Thr Ser Glu Gly Ala Gly Leu
    850                 855                 860

Gln Leu Gln Lys Val Thr Val Leu Gly Val Ala Thr Ala Pro Gln Gln
865                 870                 875                 880

Val Leu Ser Asn Gly Val Pro Val Ser Asn Phe Thr Tyr Ser Pro Asp
                885                 890                 895

Thr Lys Val Leu Asp Ile Cys Val Ser Leu Leu Met Gly Glu Gln Phe
            900                 905                 910

Leu Val Ser Trp Cys
            915

<210> SEQ ID NO 79
<211> LENGTH: 1128
<212> TYPE: PRT
<213> ORGANISM: Artificial Sequence
```

<220> FEATURE:
<223> OTHER INFORMATION: scFv_H4H123450(VH-linker-VL)_linker_GAA

<400> SEQUENCE: 79

| Gln | Val | Gln | Leu | Gln | Glu | Ser | Gly | Pro | Lys | Val | Val | Lys | Pro | Ser | Glu |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Thr | Val | Ser | Gly | Gly | Ser | Ile | Ser | Ser | Tyr |
|---|---|---|---|---|---|---|---|---|---|---|---|---|---|---|---|
| | | | 20 | | | | | 25 | | | | | 30 | | |

| Tyr | Trp | Asn | Trp | Ile | Arg | Gln | Ser | Pro | Gly | Lys | Gly | Leu | Glu | Trp | Ile |
|---|---|---|---|---|---|---|---|---|---|---|---|---|---|---|---|
| | | 35 | | | | | 40 | | | | | 45 | | | |

| Gly | Tyr | Thr | Lys | Arg | Gly | Tyr | Thr | Asp | Tyr | Asn | Pro | Ser | Leu | Arg | Ser |
|---|---|---|---|---|---|---|---|---|---|---|---|---|---|---|---|
| | 50 | | | | | 55 | | | | | 60 | | | | |

| Arg | Val | Thr | Ile | Ser | Glu | Asp | Thr | Ser | Lys | Asn | Gln | Phe | Ser | Leu | Arg |
|---|---|---|---|---|---|---|---|---|---|---|---|---|---|---|---|
| 65 | | | | | 70 | | | | | 75 | | | | | 80 |

| Ile | Ser | Ser | Val | Thr | Ala | Ala | Asp | Thr | Ala | Val | Tyr | Tyr | Cys | Ala | Gln |
|---|---|---|---|---|---|---|---|---|---|---|---|---|---|---|---|
| | | | | 85 | | | | | 90 | | | | | 95 | |

| Met | Gly | Trp | Gly | Ser | His | Ala | Phe | Asp | Met | Trp | Gly | Gln | Gly | Thr | Met |
|---|---|---|---|---|---|---|---|---|---|---|---|---|---|---|---|
| | | | 100 | | | | | 105 | | | | | 110 | | |

| Val | Ala | Val | Ser | Ser | Gly | Gly | Ser | Gly | Gly | Gly | Ser | Gly | Gly | Gly |
|---|---|---|---|---|---|---|---|---|---|---|---|---|---|---|
| | | 115 | | | | | 120 | | | | | 125 | | |

| Gly | Ser | Gly | Gly | Glu | Ile | Val | Leu | Thr | Gln | Ser | Pro | Gly | Thr | Leu | Ser |
|---|---|---|---|---|---|---|---|---|---|---|---|---|---|---|---|
| | 130 | | | | | 135 | | | | | 140 | | | | |

| Leu | Ser | Pro | Gly | Glu | Arg | Ala | Thr | Leu | Ser | Cys | Arg | Ala | Ser | Gln | Ser |
|---|---|---|---|---|---|---|---|---|---|---|---|---|---|---|---|
| 145 | | | | | 150 | | | | | 155 | | | | | 160 |

| Val | Ser | Ser | Ser | Tyr | Leu | Ala | Trp | Tyr | Gln | Gln | Lys | Pro | Gly | Gln | Ala |
|---|---|---|---|---|---|---|---|---|---|---|---|---|---|---|---|
| | | | | 165 | | | | | 170 | | | | | 175 | |

| Pro | Arg | Leu | Leu | Ile | Tyr | Gly | Ala | Ser | Ser | Arg | Ala | Thr | Gly | Ile | Pro |
|---|---|---|---|---|---|---|---|---|---|---|---|---|---|---|---|
| | | | 180 | | | | | 185 | | | | | 190 | | |

| Asp | Arg | Phe | Ser | Gly | Ser | Gly | Ser | Gly | Thr | Asp | Phe | Thr | Leu | Thr | Ile |
|---|---|---|---|---|---|---|---|---|---|---|---|---|---|---|---|
| | | | 195 | | | | | 200 | | | | | 205 | | |

| Ser | Arg | Leu | Glu | Pro | Glu | Asp | Phe | Ala | Val | Tyr | Tyr | Cys | Gln | Gln | Tyr |
|---|---|---|---|---|---|---|---|---|---|---|---|---|---|---|---|
| | 210 | | | | | 215 | | | | | 220 | | | | |

| Gly | Ser | Ser | Pro | Trp | Thr | Phe | Gly | Gln | Gly | Thr | Lys | Val | Glu | Ile | Lys |
|---|---|---|---|---|---|---|---|---|---|---|---|---|---|---|---|
| 225 | | | | | 230 | | | | | 235 | | | | | 240 |

| Gly | Gly | Gly | Gly | Ser | Ala | His | Pro | Gly | Arg | Pro | Arg | Ala | Val | Pro | Thr |
|---|---|---|---|---|---|---|---|---|---|---|---|---|---|---|---|
| | | | | 245 | | | | | 250 | | | | | 255 | |

| Gln | Cys | Asp | Val | Pro | Pro | Asn | Ser | Arg | Phe | Asp | Cys | Ala | Pro | Asp | Lys |
|---|---|---|---|---|---|---|---|---|---|---|---|---|---|---|---|
| | | | 260 | | | | | 265 | | | | | 270 | | |

| Ala | Ile | Thr | Gln | Glu | Gln | Cys | Glu | Ala | Arg | Gly | Cys | Cys | Tyr | Ile | Pro |
|---|---|---|---|---|---|---|---|---|---|---|---|---|---|---|---|
| | | 275 | | | | | 280 | | | | | 285 | | | |

| Ala | Lys | Gln | Gly | Leu | Gln | Gly | Ala | Gln | Met | Gly | Gln | Pro | Trp | Cys | Phe |
|---|---|---|---|---|---|---|---|---|---|---|---|---|---|---|---|
| | 290 | | | | | 295 | | | | | 300 | | | | |

| Phe | Pro | Pro | Ser | Tyr | Pro | Ser | Tyr | Lys | Leu | Glu | Asn | Leu | Ser | Ser | Ser |
|---|---|---|---|---|---|---|---|---|---|---|---|---|---|---|---|
| 305 | | | | | 310 | | | | | 315 | | | | | 320 |

| Glu | Met | Gly | Tyr | Thr | Ala | Thr | Leu | Thr | Arg | Thr | Thr | Pro | Thr | Phe | Phe |
|---|---|---|---|---|---|---|---|---|---|---|---|---|---|---|---|
| | | | | 325 | | | | | 330 | | | | | 335 | |

| Pro | Lys | Asp | Ile | Leu | Thr | Leu | Arg | Leu | Asp | Val | Met | Met | Glu | Thr | Glu |
|---|---|---|---|---|---|---|---|---|---|---|---|---|---|---|---|
| | | | 340 | | | | | 345 | | | | | 350 | | |

| Asn | Arg | Leu | His | Phe | Thr | Ile | Lys | Asp | Pro | Ala | Asn | Arg | Arg | Tyr | Glu |
|---|---|---|---|---|---|---|---|---|---|---|---|---|---|---|---|
| | | | 355 | | | | | 360 | | | | | 365 | | |

| Val | Pro | Leu | Glu | Thr | Pro | His | Val | His | Ser | Arg | Ala | Pro | Ser | Pro | Leu |
|---|---|---|---|---|---|---|---|---|---|---|---|---|---|---|---|
| | 370 | | | | | 375 | | | | | 380 | | | | |

| Tyr | Ser | Val | Glu | Phe | Ser | Glu | Glu | Pro | Phe | Gly | Val | Ile | Val | Arg | Arg |
|---|---|---|---|---|---|---|---|---|---|---|---|---|---|---|---|
| 385 | | | | | 390 | | | | | 395 | | | | | 400 |

```
Gln Leu Asp Gly Arg Val Leu Leu Asn Thr Thr Val Ala Pro Leu Phe
                405                 410                 415

Phe Ala Asp Gln Phe Leu Gln Leu Ser Thr Ser Leu Pro Ser Gln Tyr
                420                 425                 430

Ile Thr Gly Leu Ala Glu His Leu Ser Pro Leu Met Leu Ser Thr Ser
                435                 440                 445

Trp Thr Arg Ile Thr Leu Trp Asn Arg Asp Leu Ala Pro Thr Pro Gly
            450                 455                 460

Ala Asn Leu Tyr Gly Ser His Pro Phe Tyr Leu Ala Leu Glu Asp Gly
465                 470                 475                 480

Gly Ser Ala His Gly Val Phe Leu Leu Asn Ser Asn Ala Met Asp Val
                    485                 490                 495

Val Leu Gln Pro Ser Pro Ala Leu Ser Trp Arg Ser Thr Gly Gly Ile
                500                 505                 510

Leu Asp Val Tyr Ile Phe Leu Gly Pro Glu Pro Lys Ser Val Val Gln
                515                 520                 525

Gln Tyr Leu Asp Val Val Gly Tyr Pro Phe Met Pro Pro Tyr Trp Gly
                530                 535                 540

Leu Gly Phe His Leu Cys Arg Trp Gly Tyr Ser Ser Thr Ala Ile Thr
545                 550                 555                 560

Arg Gln Val Val Glu Asn Met Thr Arg Ala His Phe Pro Leu Asp Val
                565                 570                 575

Gln Trp Asn Asp Leu Asp Tyr Met Asp Ser Arg Arg Asp Phe Thr Phe
                580                 585                 590

Asn Lys Asp Gly Phe Arg Asp Phe Pro Ala Met Val Gln Glu Leu His
                595                 600                 605

Gln Gly Gly Arg Arg Tyr Met Met Ile Val Asp Pro Ala Ile Ser Ser
            610                 615                 620

Ser Gly Pro Ala Gly Ser Tyr Arg Pro Tyr Asp Glu Gly Leu Arg Arg
625                 630                 635                 640

Gly Val Phe Ile Thr Asn Glu Thr Gly Gln Pro Leu Ile Gly Lys Val
                    645                 650                 655

Trp Pro Gly Ser Thr Ala Phe Pro Asp Phe Thr Asn Pro Thr Ala Leu
                660                 665                 670

Ala Trp Trp Glu Asp Met Val Ala Glu Phe His Asp Gln Val Pro Phe
                675                 680                 685

Asp Gly Met Trp Ile Asp Met Asn Glu Pro Ser Asn Phe Ile Arg Gly
            690                 695                 700

Ser Glu Asp Gly Cys Pro Asn Asn Glu Leu Glu Asn Pro Pro Tyr Val
705                 710                 715                 720

Pro Gly Val Val Gly Gly Thr Leu Gln Ala Ala Thr Ile Cys Ala Ser
                    725                 730                 735

Ser His Gln Phe Leu Ser Thr His Tyr Asn Leu His Asn Leu Tyr Gly
                740                 745                 750

Leu Thr Glu Ala Ile Ala Ser His Arg Ala Leu Val Lys Ala Arg Gly
                755                 760                 765

Thr Arg Pro Phe Val Ile Ser Arg Ser Thr Phe Ala Gly His Gly Arg
            770                 775                 780

Tyr Ala Gly His Trp Thr Gly Asp Val Trp Ser Ser Trp Glu Gln Leu
785                 790                 795                 800

Ala Ser Ser Val Pro Glu Ile Leu Gln Phe Asn Leu Leu Gly Val Pro
                    805                 810                 815
```

```
Leu Val Gly Ala Asp Val Cys Gly Phe Leu Gly Asn Thr Ser Glu
            820                 825                 830

Leu Cys Val Arg Trp Thr Gln Leu Gly Ala Phe Tyr Pro Phe Met Arg
        835                 840                 845

Asn His Asn Ser Leu Leu Ser Leu Pro Gln Glu Pro Tyr Ser Phe Ser
    850                 855                 860

Glu Pro Ala Gln Gln Ala Met Arg Lys Ala Leu Thr Leu Arg Tyr Ala
865                 870                 875                 880

Leu Leu Pro His Leu Tyr Thr Leu Phe His Gln Ala His Val Ala Gly
                885                 890                 895

Glu Thr Val Ala Arg Pro Leu Phe Leu Glu Phe Pro Lys Asp Ser Ser
            900                 905                 910

Thr Trp Thr Val Asp His Gln Leu Leu Trp Gly Glu Ala Leu Leu Ile
        915                 920                 925

Thr Pro Val Leu Gln Ala Gly Lys Ala Glu Val Thr Gly Tyr Phe Pro
    930                 935                 940

Leu Gly Thr Trp Tyr Asp Leu Gln Thr Val Pro Val Glu Ala Leu Gly
945                 950                 955                 960

Ser Leu Pro Pro Pro Ala Ala Pro Arg Glu Pro Ala Ile His Ser
                965                 970                 975

Glu Gly Gln Trp Val Thr Leu Pro Ala Pro Leu Asp Thr Ile Asn Val
            980                 985                 990

His Leu Arg Ala Gly Tyr Ile Ile Pro Leu Gln Gly Pro Gly Leu Thr
                995                1000                1005

Thr Thr Glu Ser Arg Gln Gln Pro Met Ala Leu Ala Val Ala Leu
            1010                1015                1020

Thr Lys Gly Gly Glu Ala Arg Gly Glu Leu Phe Trp Asp Asp Gly
            1025                1030                1035

Glu Ser Leu Glu Val Leu Glu Arg Gly Ala Tyr Thr Gln Val Ile
            1040                1045                1050

Phe Leu Ala Arg Asn Asn Thr Ile Val Asn Glu Leu Val Arg Val
            1055                1060                1065

Thr Ser Glu Gly Ala Gly Leu Gln Leu Gln Lys Val Thr Val Leu
            1070                1075                1080

Gly Val Ala Thr Ala Pro Gln Val Leu Ser Asn Gly Val Pro
            1085                1090                1095

Val Ser Asn Phe Thr Tyr Ser Pro Asp Thr Lys Val Leu Asp Ile
            1100                1105                1110

Cys Val Ser Leu Leu Met Gly Glu Gln Phe Leu Val Ser Trp Cys
            1115                1120                1125

<210> SEQ ID NO 80
<211> LENGTH: 125
<212> TYPE: PRT
<213> ORGANISM: Artificial Sequence
<220> FEATURE:
<223> OTHER INFORMATION: CD63 EC loop 2 MMH

<400> SEQUENCE: 80

Arg Asp Lys Val Met Ser Glu Phe Asn Asn Phe Arg Gln Gln Met
1               5                   10                  15

Glu Asn Tyr Pro Lys Asn Asn His Thr Ala Ser Ile Leu Asp Arg Met
            20                  25                  30

Gln Ala Asp Phe Lys Cys Cys Gly Ala Ala Asn Tyr Thr Asp Trp Glu
        35                  40                  45
```

```
Lys Ile Pro Ser Met Ser Lys Asn Arg Val Pro Asp Ser Cys Cys Ile
        50                  55                  60

Asn Val Thr Val Gly Cys Gly Ile Asn Phe Asn Glu Lys Ala Ile His
 65                  70                  75                  80

Lys Glu Gly Cys Val Glu Lys Ile Gly Gly Trp Leu Arg Lys Asn Val
                85                  90                  95

Leu Glu Gln Lys Leu Ile Ser Glu Glu Asp Leu Gly Gly Glu Gln Lys
                100                 105                 110

Leu Ile Ser Glu Glu Asp Leu His His His His His
                115                 120                 125
```

<210> SEQ ID NO 81
<211> LENGTH: 324
<212> TYPE: PRT
<213> ORGANISM: Artificial Sequence
<220> FEATURE:
<223> OTHER INFORMATION: CD63 EC loop 2 hFC

<400> SEQUENCE: 81

```
Arg Asp Lys Val Met Ser Glu Phe Asn Asn Asn Phe Arg Gln Gln Met
 1               5                  10                  15

Glu Asn Tyr Pro Lys Asn Asn His Thr Ala Ser Ile Leu Asp Arg Met
                20                  25                  30

Gln Ala Asp Phe Lys Cys Cys Gly Ala Ala Asn Tyr Thr Asp Trp Glu
            35                  40                  45

Lys Ile Pro Ser Met Ser Lys Asn Arg Val Pro Asp Ser Cys Cys Ile
        50                  55                  60

Asn Val Thr Val Gly Cys Gly Ile Asn Phe Asn Glu Lys Ala Ile His
 65                  70                  75                  80

Lys Glu Gly Cys Val Glu Lys Ile Gly Gly Trp Leu Arg Lys Asn Val
                85                  90                  95

Leu Asp Lys Thr His Thr Cys Pro Pro Cys Pro Ala Pro Glu Leu Leu
                100                 105                 110

Gly Gly Pro Ser Val Phe Leu Phe Pro Pro Lys Pro Lys Asp Thr Leu
            115                 120                 125

Met Ile Ser Arg Thr Pro Glu Val Thr Cys Val Val Val Asp Val Ser
        130                 135                 140

His Glu Asp Pro Glu Val Lys Phe Asn Trp Tyr Val Asp Gly Val Glu
145                 150                 155                 160

Val His Asn Ala Lys Thr Lys Pro Arg Glu Glu Gln Tyr Asn Ser Thr
                165                 170                 175

Tyr Arg Val Val Ser Val Leu Thr Val Leu His Gln Asp Trp Leu Asn
                180                 185                 190

Gly Lys Glu Tyr Lys Cys Lys Val Ser Asn Lys Ala Leu Pro Ala Pro
            195                 200                 205

Ile Glu Lys Thr Ile Ser Lys Ala Lys Gly Gln Pro Arg Glu Pro Gln
        210                 215                 220

Val Tyr Thr Leu Pro Pro Ser Arg Asp Glu Leu Thr Lys Asn Gln Val
225                 230                 235                 240

Ser Leu Thr Cys Leu Val Lys Gly Phe Tyr Pro Ser Asp Ile Ala Val
                245                 250                 255

Glu Trp Glu Ser Asn Gly Gln Pro Glu Asn Asn Tyr Lys Thr Thr Pro
                260                 265                 270

Pro Val Leu Asp Ser Asp Gly Ser Phe Phe Leu Tyr Ser Lys Leu Thr
            275                 280                 285
```

```
Val Asp Lys Ser Arg Trp Gln Gln Gly Asn Val Phe Ser Cys Ser Val
    290                 295                 300

Met His Glu Ala Leu His Asn His Tyr Thr Gln Lys Ser Leu Ser Leu
305                 310                 315                 320

Ser Pro Gly Lys
```